(12) United States Patent
Sidransky

(10) Patent No.: US 12,233,072 B2
(45) Date of Patent: Feb. 25, 2025

(54) COMPOSITIONS COMPRISING BISFLUOROALKYL-1,4-BENZODIAZEPINONE COMPOUNDS FOR TREATING ADENOID CYSTIC CARCINOMA

(71) Applicant: Immunome, Inc., Bothell, WA (US)

(72) Inventor: David Sidransky, Pikesville, MD (US)

(73) Assignee: Immunome, Inc., Bothell, WA (US)

(*) Notice: Subject to any disclaimer, the term of this patent is extended or adjusted under 35 U.S.C. 154(b) by 0 days.

(21) Appl. No.: 16/586,890

(22) Filed: Sep. 27, 2019

(65) Prior Publication Data

US 2020/0022990 A1 Jan. 23, 2020

Related U.S. Application Data

(63) Continuation-in-part of application No. PCT/US2019/032239, filed on May 14, 2019.

(60) Provisional application No. 62/827,892, filed on Apr. 2, 2019, provisional application No. 62/804,781, filed on Feb. 13, 2019, provisional application No. 62/671,748, filed on May 15, 2018.

(51) Int. Cl.
*A61K 31/5513* (2006.01)
*A61P 35/04* (2006.01)

(52) U.S. Cl.
CPC .......... *A61K 31/5513* (2013.01); *A61P 35/04* (2018.01)

(58) Field of Classification Search
CPC ....... A61K 31/5513; A61P 35/00; A61P 35/04
See application file for complete search history.

(56) References Cited

U.S. PATENT DOCUMENTS

| | | |
|---|---|---|
| 8,629,136 B2 | 1/2014 | Gavai et al. |
| 9,273,014 B2 | 3/2016 | Gavai et al. |
| 9,273,075 B2 | 3/2016 | Gavai et al. |

FOREIGN PATENT DOCUMENTS

| | | |
|---|---|---|
| WO | WO-2000038618 A2 | 7/2000 |
| WO | WO-2012129353 A1 | 9/2012 |
| WO | WO-2014047372 A1 | 3/2014 |
| WO | WO-2014047391 A1 | 3/2014 |
| WO | WO-2014165718 A1 | 10/2014 |
| WO | WO-2015134627 A1 | 9/2015 |
| WO | WO-2019215585 A1 | 11/2019 |
| WO | WO-2019217250 A1 | 11/2019 |
| WO | WO-2019222298 A1 | 11/2019 |
| WO | WO-2019226329 A1 | 11/2019 |

OTHER PUBLICATIONS

Oakley et al., Abstract 1133: Prevalence of activated NOTCH receptor in solid tumors and chronic lymphocytic leukemia. Proceedings of the 107th annual meeting of the American Association for Cancer Research, Apr. 16-20, 76(14 Suppl) (Year: 2016).*
Ding et al., Notch-4 contributes to the metastasis of salivary adenoid cystic carcinoma. Oncology Reports, vol. 24, pp. 363-368 ( Year: 2010).*
Qu et al., Notch2 signaling contributes to cell growth, invasion, and migration in salivary adenoid cystic carcinoma. Mo. Cell Biochem., vol. 411, pp. 135-141 (Year: 2016).*
Kamdje et al., Signaling pathways in breast cancer: Therapeutic targeting of the microenvironment. Cellular Signaling, vol. 26, pp. 2843-2856 (Year: 2014).*
Ferrarotto et al., Activating NOTCH1 mutations define a distinct subgroup of patients with adenoid cystic carcinoma who have poor prognosis, propensity to bone and liveer metastasis and potential responsiveness to Notch1 inhibitors. J. of Clin. Oncology, vol. 35( 3), pp. 352-360 (Year: 2017).*
Xie et al., Alterations of Notch pathway among patients with adenoid cystic carcinoma of the trachea and its impact on survival. Mini Oral Abstracts, vol. 12(11S2) (Year: 2017).*
Andersson, E. R., et al. (2014). Therapeutic modulation of Notch signaling—are we there yet? Nature Reviews Drug Discovery, 13(5), 357.
Anonymous. Ayala Pharmaceuticals Presents Phase 1b Data at the 2018 American Society of Clinical Oncology (ASCO) Annual Meeting for AL101, a Pan-Notch Inhibitor, in Patients with Locally Advanced or Metastatic Solid Tumors. (Jun. 2018). Retrieved on-line at: https://www.businesswire.com/news/home/20180604005719/en/Ayala-Pharmaceuticals-Presents-Phase-1b-Data-2018.
Aung, K. L. et al. (2018). A multi-arm phase I dose escalating study of an oral NOTCH inhibitor BMS-986115 in patients with advanced solid tumours. Investigational new drugs, 36(6), 1026-1036.
clinicaltrials.gov Identifier: NCT01292655; Phase 1 Ascending Multiple-Dose Study to Evaluate the Safety, Pharmacokinetics (PK) and Pharmacodynamics (PD) of BMS-906024 in Subjects with Advanced Solid Tumors. (Feb. 2011). Retrieved on-line at: https://clinicaltrials.gov/ct2/show/study/NCT01292655.
clinicaltrials.gov Identifier: NCT03691207; A Phase 2, Open-Label, Single-Arm, Multi-Center Study of AL101 (BMS-906024) in Patients with Adenoid Cystic Carcinoma (ACC) Bearing Activating Notch Mutations. (Oct. 2018) Retrieved on-line at: https://clinicaltrials.gov/ct2/show/NCT03691207.

(Continued)

*Primary Examiner* — Barbara P Badio
(74) *Attorney, Agent, or Firm* — Goodwin Procter LLP

(57) ABSTRACT

The present invention provides methods of treating or suppressing Adenoid Cystic Carcinoma (ACC) or inhibiting ACC tumor growth in subjects by administering compositions comprising bisfluoroalkyl-1,4-benzodiazepinone compounds, including compounds of Formula (III) or prodrugs thereof.

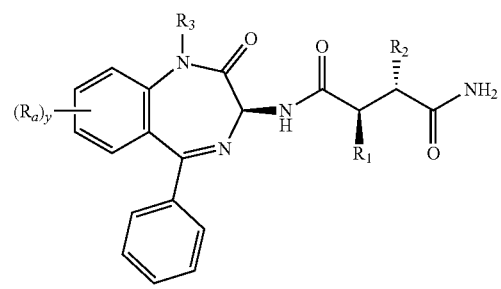

13 Claims, 18 Drawing Sheets

(56) References Cited

OTHER PUBLICATIONS

Ferrarotto, R., et al. (2017). Taking it up a NOTCH: a novel subgroup of ACC is identified. Oncotarget, 8(47), 81725.
Fung, E. N., et al. (2015). Utilizing internal standard responses to assess risk on reporting bioanalytical results from hemolyzed samples. The AAPS journal, 17(5), 1168-1176.
Gavai, A. V., et al. (2015). Discovery of clinical candidate BMS-906024: a potent pan-notch inhibitor for the treatment of leukemia and solid tumors. ACS medicinal chemistry letters, 6(5), 523-527.
International Search Report and Written Opinion of International Search Authority dated Aug. 25, 2019, issued for PCT International Application No. PCT/US2019/032239, filed May 14, 2019.
Stoeck, A., et al. (2014). Discovery of biomarkers predictive of GSI response in triple-negative breast cancer and adenoid cystic carcinoma. Cancer discovery, 4(10), 1154-1167.
Taylor, P. (Apr. 2018). Ayala notches up $17M in financing to push BMS drug into phase 2. Retrieved on-line at: https://www.fiercebiotech.com/biotech/ayala-notches-up-17m-financing-to-push-bms-drug-into-phase-2.
Adenoid Cystic Carcinoma Research Foundation (2014). Selected Phase I Clinical Trials of NOTCH Inhibitors. Updated May 2014. p. 1. Retrieved on-line on Dec. 25, 2015 at: http://www.accrf.org/wp-content/uploads/Clinical-Trials-Phase-I-2014-May.pdf.
El-Khoueiry, A. B. et al. (2018). A phase I study of AL101, a pan-NOTCH inhibitor, in patients (pts) with locally advanced or metastatic solid tumors. Journal of Clinical Oncology, vol. 36(15-suppl). Abstract. Published online Jun. 1, 2018.
Ferrarotto, R. et al. (2017). Activating NOTCH1 mutations define a distinct subgroup of patients with adenoid cystic carcinoma who have poor prognosis, propensity to bone and liver metastasis, and potential responsiveness to Notch1 inhibitors. Journal of Clinical Oncology, 35(3), 352-360.
International Preliminary Report on Patentability (Chapter I of the Patent Cooperation Treaty) dated Nov. 26, 2020, issued for the corresponding PCT International Application No. PCT/US2019/032239, dated May 14, 2019.
Taylor P. (2018). Ayala notches up $17M in financing to push BMS drug into phase 2. *Fierce Biotech*, 2 Pages. Retrieved on-line on Jul. 29, 2021 at: https://www.fiercebiotech.com/biotech/ayala-notches-up-17m-financing-to-push-bms-drug-into-phase-2.
Weber D. (2017). Aberrant NOTCH Signalling in Breast Cancer: an attractive target for pan-NOTCH inhibition. *Cellestia Basel Breast Consortium presentation*, Basel, 03—Oct. 3, 2017, 26 pages. Retrieved on-line on Jul. 29, 2021 at:cellestia.com/wp-content/uploads/2019/12/Cellestia_BBC-presentation_Breast-Cancer-NOTCH_v2_20171003.pdf.
Weng, A. P. et al.(2004). Activating mutations of NOTCH1 in human T cell acute lymphoblastic leukemia. *Science*, 306(5694), 269-271.
Yarbrough, W. G. et al. (2016). Clinical and molecular insights into adenoid cystic carcinoma: neural crest-like stemness as a target. *Laryngoscope Investigative Otolaryngology*, 1(4), 60-77.
Chen, W. et al. (2015). Notch-1 knockdown suppresses proliferation, migration and metastasis of salivary adenoid cystic carcinoma cells. *Journal of Translational Medicine*, 13(1), 1-10.
Bell, D. et al. (2014). Expression and significance of notch signaling pathway in salivary adenoid cystic carcinoma. *Annals of Diagnostic Pathology*, 18(1), 10-13.
Xie, M. et al. (2018). Alterations of Notch pathway in patients with adenoid cystic carcinoma of the trachea and its impact on survival. *Lung Cancer*, 121, 41-47.
Andersson, E. R. et al. (2014). Therapeutic modulation of Notch signalling—are we there yet ?. *Nature Reviews Drug Discovery*, 13(5), 357-378.
clinical trials.gov, Identifier: NCT01653470 (2018). Study to Evaluate Safety & Tolerability of BMS-906024 in Combination with Chemotherapy & to Define DLTs & MTD of BMS Combination with One of the Following Chemotherapy Regimens; Weekly Paclitaxel, 5FU+Irinotecan or Carboplatin+Pac Subjects with Advanced / Metastatic Solid Tumors. Retrieved online at URL: https://clinicaltrials.gov/study/NCT01653470.

\* cited by examiner

COMPOSITIONS COMPRISING BISFLUOROALKYL-1,4-BENZODIAZEPINONE COMPOUNDS FOR TREATING ADENOID CYSTIC CARCINOMA

CROSS-REFERENCE TO RELATED APPLICATIONS

This application is a Continuation-in-part of PCT International Application Number PCT/US2019/032239 filed on May 14, 2019, and which claims the benefit of U.S. Provisional Application Ser. No. 62/671,748 filed May 15, 2018, U.S. Provisional Application Ser. No. 62/804,781 filed Feb. 13, 2019, and U.S. Provisional Application Ser. No. 62/827,892 filed Apr. 2, 2019, which are hereby incorporated by reference in their entirety herein.

FIELD OF THE INVENTION

The present invention provides methods of treating or suppressing Adenoid Cystic Carcinoma (ACC) or inhibiting ACC tumor growth in subjects by administering compositions comprising bisfluoroalkyl-1,4-benzodiazepinone compounds, including compounds of Formula (III) or prodrugs thereof.

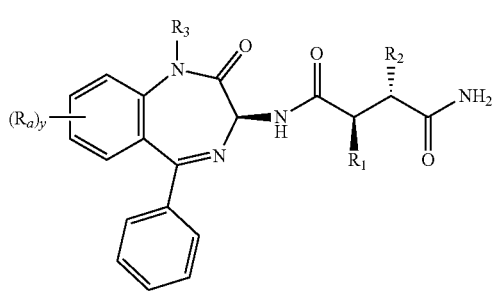

(III)

BACKGROUND OF THE INVENTION

Many human solid tumors and hematologic malignancies show a characteristic deregulation of Notch pathway signaling. An important step in activation of Notch receptors is cleavage by gamma secretase, freeing the intracellular signaling domain. Notch inhibition by gamma secretase inhibitors (GSIs) such as benzodiazepinone compounds has potential for having potent antineoplastic effects.

Patients with advanced solid tumors refractory to standard therapies, patients who relapsed after standard therapies or patients with tumors for which there is no known effective treatment require new strategies for treating solid tumors.

SUMMARY OF THE INVENTION

The present invention provides a method of treating or suppressing an Adenoid Cystic Carcinoma (ACC) tumor in a subject comprising the step of administering to said subject a composition comprising one or more compounds represented by the structure of Formula (III):

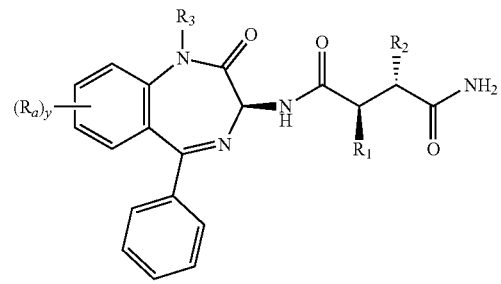

or prodrugs or salts thereof; wherein:
$R_1$ is —$CH_2CF_3$ or —$CH_2CH_2CF_3$;
$R_2$ is —$CH_2CF_3$, —$CH_2CH_2CF_3$, or —$CH_2CH_2CH_2CF_3$;
$R_3$ is H or —$CH_3$;
each $R_a$ is independently F, Cl, —CN, —$OCH_3$, and/or —$NHCH_2CH_2OCH_3$; and
y is zero, 1, or 2.

The present invention also provides a method of inhibiting tumor growth in a subject with an Adenoid Cystic Carcinoma (ACC) tumor comprising the step of administering to said subject a composition comprising one or more compounds represented by the structure of Formula (III):

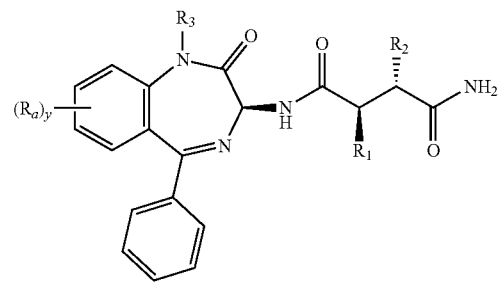

or prodrugs or salts thereof; wherein:
$R_1$ is —$CH_2CF_3$ or —$CH_2CH_2CF_3$;
$R_2$ is —$CH_2CF_3$, —$CH_2CH_2CF_3$, or —$CH_2CH_2CH_2CF_3$;
$R_3$ is H or —$CH_3$;
each $R_a$ is independently F, Cl, —CN, —$OCH_3$, and/or —$NHCH_2CH_2OCH_3$; and
y is zero, 1, or 2.

DETAILED DESCRIPTION OF THE PRESENT INVENTION

Figure 1:
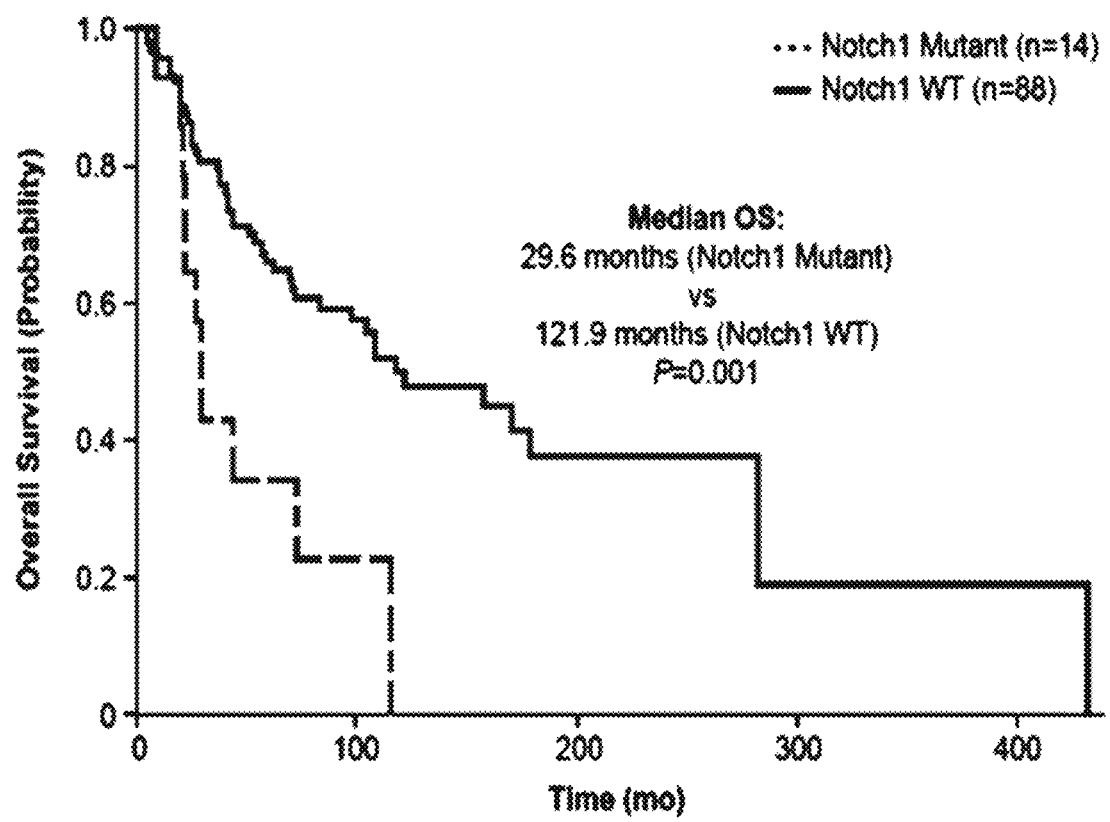
FIG. 1. Overall survival of patients with Adenoid Cystic Carcinoma (ACC). Survival of ACC patients having Notch1 mutation (n=14) and of ACC patients having wild-type Notch1 (n=88) is shown (adapted from Ferrarotto R, et al. J Clin Oncol. 2017; 35:352-360, incorporated herein by reference). P=0.001; OS-Overall Survival; WT-wild-type.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, compositions of the present invention or for use in the methods of the present invention comprise one or more gamma secretase inhibitors, one or more Notch inhibitors, or a combination thereof. In one embodiment, the gamma secretase inhibitor comprises a bisfluoroalkyl-1,4-benzodiazepinone compound.

Bisfluoroalkyl-1,4-benzodiazepinone Compounds

In one embodiment, the present invention provides compositions comprising compounds represented by the structure of Formula (I):

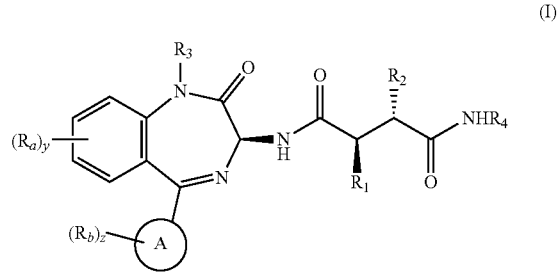

and/or at least one salt thereof, wherein:
$R_1$ is —$CH_2CF_3$ or —$CH_2CH_2CF_3$;
$R_2$ is —$CH_2CF_3$, —$CH_2CH_2CF_3$, or —$CH_2CH_2CH_2CF_3$;
$R_3$ is H, —$CH_3$ or Rx;
$R_4$ is H or $R_y$;

$R_x$ is: —CH$_2$OC(O)CH(CH$_3$)NH$_2$, —CH$_2$OC(O)CH(NH$_2$)CH(CH$_3$)$_2$, —CH$_2$OC(O)CH((CH(CH$_3$)$_2$)NHC(O)CH(NH$_2$)CH(CH$_3$)$_2$,

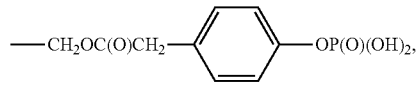

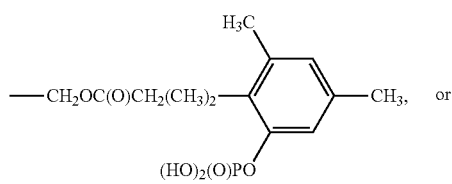

or

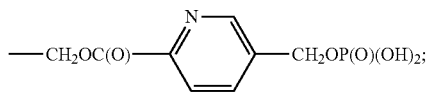

$R_y$ is: —SCH$_2$CH(NH$_2$)C(O)OH, —SCH$_2$CH(NH$_2$)C(O)OCH$_3$, or —SCH$_2$CH(NH$_2$)C(O)OC(CH$_3$)$_3$;

Ring A is phenyl or pyridinyl;

each $R_a$ is independently F, Cl, —CN, —OCH$_3$, C$_{1-3}$ alkyl, —CH$_2$OH, —CF$_3$, cyclopropyl, —OCH$_3$, —O(cyclopropyl) and/or —NHCH$_2$CH$_2$OCH$_3$;

each $R_b$ is independently F, Cl, —CH$_3$, —CH$_2$OH, —CF$_3$, cyclopropyl, and/or —OCH$_3$;

y is zero, 1 or 2; and z is zero, 1, or 2.

In one embodiment, the present invention provides compositions comprising compounds as described herein formulated at a dose of 4 mg. In one embodiment, the present invention provides compositions comprising compounds as described herein formulated for intravenous administration.

In one embodiment, the present invention provides compositions comprising compounds represented by the structure of Formula (II):

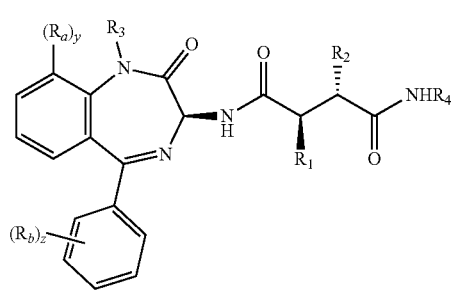

wherein $R_3$ is H or —CH$_3$; and y is zero or 1.

In one embodiment, the present invention provides compositions comprising compounds of Formula (III):

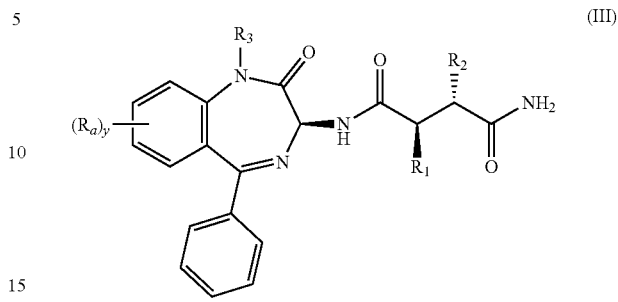

or prodrugs or salts thereof; wherein:
$R_1$ is —CH$_2$CF$_3$ or —CH$_2$CH$_2$CF$_3$;
$R_2$ is —CH$_2$CF$_3$, —CH$_2$CH$_2$CF$_3$, or —CH$_2$CH$_2$CH$_2$CF$_3$;
$R_3$ is H or —CH$_3$;
each $R_a$ is independently F, Cl, —CN, —OCH$_3$, and/or —NHCH$_2$CH$_2$OCH$_3$; and
y is zero, 1, or 2.

In one embodiment, $R_1$ is —CH$_2$CF$_3$ or —CH$_2$CH$_2$CF$_3$ and $R_2$ is —CH$_2$CF$_3$ or —CH$_2$CH$_2$CF$_3$. In another embodiment, $R_1$ is —CH$_2$CH$_2$CF$_3$ and $R_2$ is —CH$_2$CH$_2$CF$_3$. In one embodiment, y is 1 or 2. In another embodiment, y is zero or 1. In one embodiment, y is zero.

In one embodiment, the compound of Formula (III) comprises: (2R,3S)—N-((3S)-1-methyl-2-oxo-5-phenyl-2,3-dihydro-1H-1,4-benzodiazepin-3-yl)-2,3-bis(3,3,3-trifluoropropyl)succinamide (1)

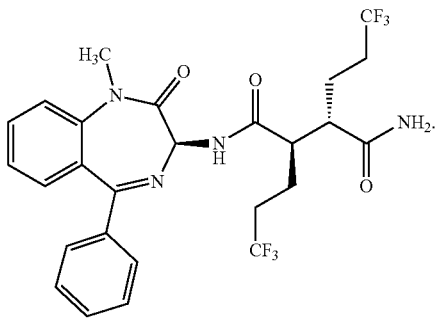 [SMILES: CN1C(=O)[C@@H](NC(=O)[C@H](CCC(F)(F)F)[C@H](CCC(F)(F)F)C(N)=O)N=C(c2ccccc2)c2ccccc21]

In another embodiment, the compound of Formula (III) comprises: (2R,3S)—N-((3S)-2-oxo-5-phenyl-2,3-dihydro-1H-1,4-benzodiazepin-3-yl)-2,3-bis(3,3,3-trifluoropropyl)succinamide (2)

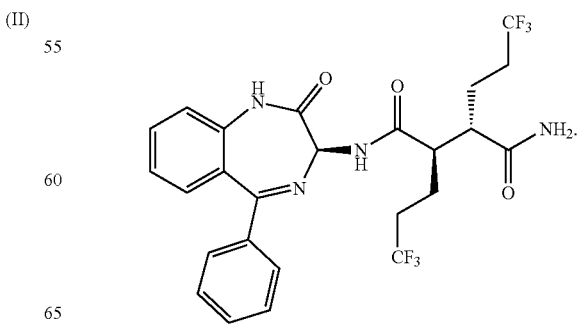

In another embodiment, the compound of Formula (III) comprises: (2R,3S)—N-((3S)-1-methyl-2-oxo-5-phenyl-2,3-dihydro-1H-1,4-benzodiazepin-3-yl)-2-(2,2,2-trifluoroethyl)-3-(3,3,3-trifluoropropyl)succinamide (3);

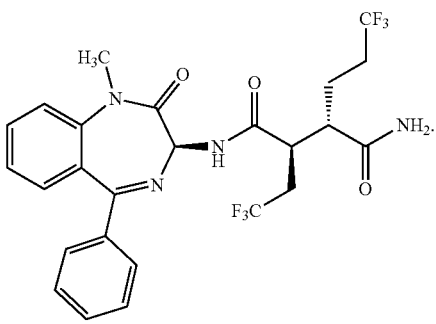

(3)

In another embodiment, the compound of Formula (III) comprises: (2R,3S)—N-((3S)-1-methyl-2-oxo-5-phenyl-2,3-dihydro-1H-1,4-benzodiazepin-3-yl)-3-(2,2,2-trifluoroethyl)-2-(3,3,3-trifluoropropyl)succinamide (4);

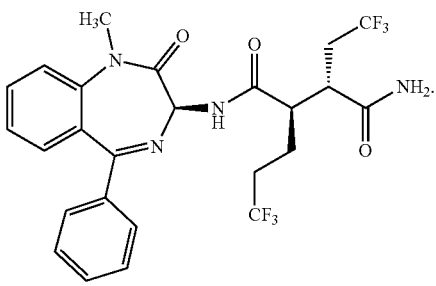

(4)

In another embodiment, the compound of Formula (III) comprises: (2R,3S)—N-((3S)-1-($^2$H$_3$)methyl-2-oxo-5-phenyl-2,3-dihydro-1H-1,4-benzodiazepin-3-yl)-2,3-bis(3,3,3-trifluoropropyl)succinamide (5);

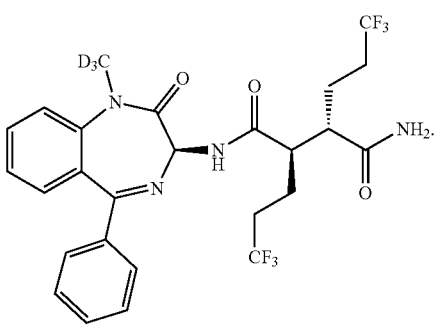

(5)

In another embodiment, the compound of Formula (III) comprises a compound of Formula (VI):

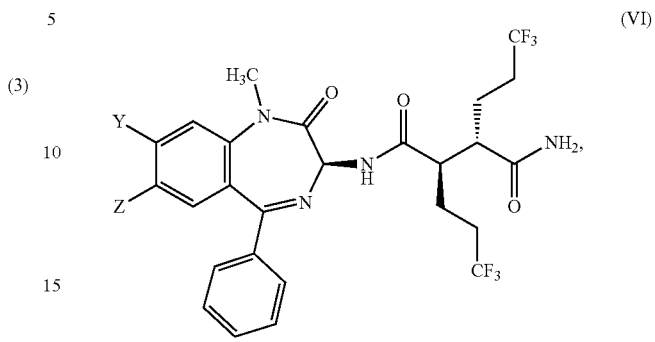

(VI)

which in one embodiment, comprises (2R,3S)—N-((3S)-7-chloro-1-methyl-2-oxo-5-phenyl-2,3-dihydro-1H-1,4-benzodiazepin-3-yl)-2,3-bis(3,3,3-trifluoropropyl)succinamide (6), i.e. Y=H and Z=Cl; (2R,3S)—N-((3S)-8-methoxy-1-methyl-2-oxo-5-phenyl-2,3-dihydro-1H-1,4-benzodiazepin-3-yl)-2,3-bis(3,3,3-trifluoropropyl)succinamide (7), i.e. Y=OCH$_3$ and Z=H; (2R,3S)—N-((3S)-8-fluoro-1-methyl-2-oxo-5-phenyl-2,3-dihydro-1H-1,4-benzodiazepin-3-yl)-2,3-bis(3,3,3-trifluoropropyl)succinamide (8), i.e. Y=F and Z=H; (2R,3S)—N-((3S)-7-methoxy-1-methyl-2-oxo-5-phenyl-2,3-dihydro-1H-1,4-benzodiazepin-3-yl)-2,3-bis(3,3,3-trifluoropropyl)succinamide (9), Y=H and Z=OCH$_3$; (2R,3S)—N-((3S)-7-fluoro-1-methyl-2-oxo-5-phenyl-2,3-dihydro-1H-1,4-benzodiazepin-3-yl)-2,3-bis(3,3,3-trifluoropropyl)succinamide (10), i.e. Y=H and Z=F; or (2R,3S)—N-((3S)-8-chloro-1-methyl-2-oxo-5-phenyl-2,3-dihydro-1H-1,4-benzodiazepin-3-yl)-2,3-bis(3,3,3-trifluoropropyl)succinamide (11), i.e. Y=Cl and Z=H.

In another embodiment, the compound of Formula (III) comprises a compound of Formula (VII):

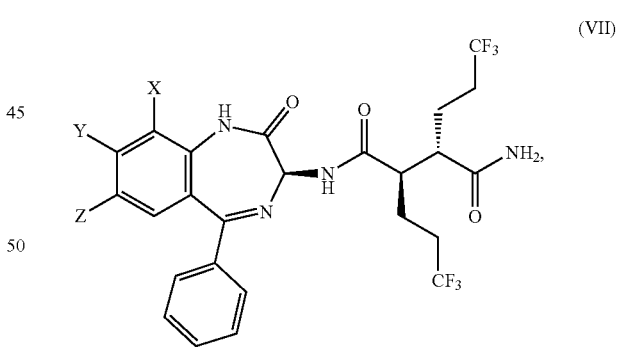

(VII)

which in one embodiment, comprises (2R,3S)—N-((3S)-9-methoxy-2-oxo-5-phenyl-2,3-dihydro-1H-1,4-benzodiazepin-3-yl)-2,3-bis(3,3,3-trifluoropropyl)succinamide (12), i.e. X=OCH$_3$, Y=H and Z=H; (2R,3S)—N-((3S)-8-methoxy-2-oxo-5-phenyl-2,3-dihydro-1H-1,4-benzodiazepin-3-yl)-2,3-bis(3,3,3-trifluoropropyl)succinamide (13), i.e. X=H, Y=OCH$_3$ and Z=H; (2R,3S)—N-((3S)-7-methoxy-2-oxo-5-phenyl-2,3-dihydro-1H-1,4-benzodiazepin-3-yl)-2,3-bis(3,3,3-trifluoropropyl)succinamide (14), i.e. X=H, Y=H and Z=OCH$_3$; (2R,3S)—N-((3S)-8-cyano-9-methoxy-2-oxo-5-phenyl-2,3-dihydro-1H-1,4-benzodiazepin-3-yl)-2,3-bis(3,3,3-trifluoropropyl)succinamide (15), i.e. X=OCH₃, Y=CN and Z=H; (2R,3S)—N-((3S)-8,9-dichloro-2-oxo-5-phenyl-2,3-dihydro-1H-1,4-benzodiazepin-3-yl)-2,3-bis(3,3,3-trifluoropropyl)succinamide (16), i.e. X=Cl, Y=Cl and Z=H; (2R,3S)—N-((3S)-9-fluoro-2-oxo-5-phenyl-2,3-dihydro-1H-1,4-benzodiazepin-3-yl)-2,3-bis(3,3,3-trifluoropropyl)succinamide (17), i.e. X=F, Y=H and Z=H; or (2R,3S)—N-((3S)-9-chloro-2-oxo-5-phenyl-2,3-dihydro-1H-1,4-benzodiazepin-3-yl)-2,3-bis(3,3,3-trifluoropropyl)succinamide (18), i.e. X=Cl, Y=H and Z=H.

In another embodiment, the compound of Formula (III) comprises: (2R,3S)—N-((3S)-2-oxo-5-phenyl-2,3-dihydro-1H-1,4-benzodiazepin-3-yl)-3-(4,4,4-trifluorobutyl)-2-(3,3,3-trifluoropropyl)succinamide (19);

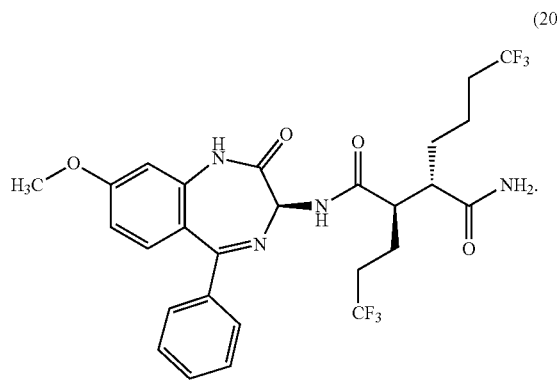

(19)

In another embodiment, the compound of Formula (III) comprises: (2R,3S)—N-((3S)-8-methoxy-2-oxo-5-phenyl-2,3-dihydro-1H-1,4-benzodiazepin-3-yl)-3-(4,4,4-trifluorobutyl)-2-(3,3,3-trifluoropropyl)succinamide (20)

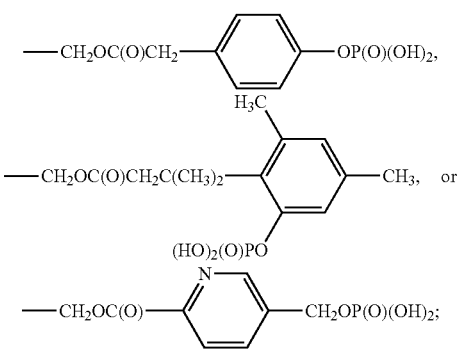

(20)

In another embodiment, the compound of Formula (III) comprises: (2R,3S)—N-((3S)-9-((2-methoxyethyl)amino)-2-oxo-5-phenyl-2,3-dihydro-1H-1,4-benzodiazepin-3-yl)-2,3-bis(3,3,3-trifluoropropyl)succinamide (21)

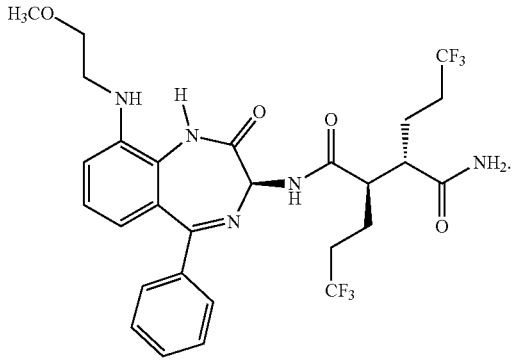

(21)

In another embodiment, the present invention provides compositions comprising compounds represented by the structure of Formula (I):

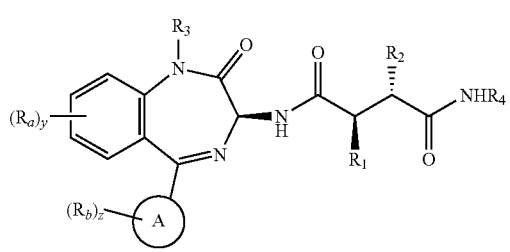

(I)

and/or at least one salt thereof, wherein:
R₁ is —CH₂CF₃;
R₂ is —CH₂CH₂CF₃, or —CH₂CH₂CH₂CF₃;
R₃ is H, —CH₃ or R$_x$;
R₄ is H or R$_y$;
R$_x$ is: —CH₂OC(O)CH(CH₃)NH₂, —CH₂OC(O)CH(NH₂)CH(CH₃)₂, —CH₂OC(O)CH((CH(CH₃)₂)NHC(O)CH(NH₂)CH(CH₃)₂, —CH₂OC(O)CH₂—⟨phenyl⟩—OP(O)(OH)₂, —CH₂OC(O)CH₂C(CH₃)₂—⟨substituted phenyl with H₃C, CH₃, (HO)₂(O)P⟩, or —CH₂OC(O)—⟨pyridine⟩—CH₂OP(O)(OH)₂;

R$_y$ is: —SCH₂CH(NH₂)C(O)OH, —SCH₂CH(NH₂)C(O)OCH₃, or —SCH₂CH(NH₂)C(O)OC(CH₃)₃;
Ring A is phenyl or pyridinyl;
each R$_a$ is independently Cl, C₁₋₃ alkyl, —CH₂OH, —CF₃, cyclopropyl, —OCH₃, and/or —O(cyclopropyl);
each R$_b$ is independently F, Cl, —CH₃, —CH₂OH, —CF₃, cyclopropyl, and/or —OCH₃;

y is zero, 1 or 2; and z is 1 or 2.

In another embodiment, Ring A is phenyl; and $R_3$ is H. In another embodiment, $R_2$ is —$CH_2CH_2CF_3$; and Ring A is phenyl. In another embodiment, $R_2$ is —$CH_2CH_2CF_3$; Ring A is phenyl; $R_a$ is $C_{1-3}$ alkyl or —$CH_2OH$; each $R_b$ is independently F and/or Cl; and y is 1.

In another embodiment, the present invention provides compositions comprising compounds represented by the structure of Formula (IV):

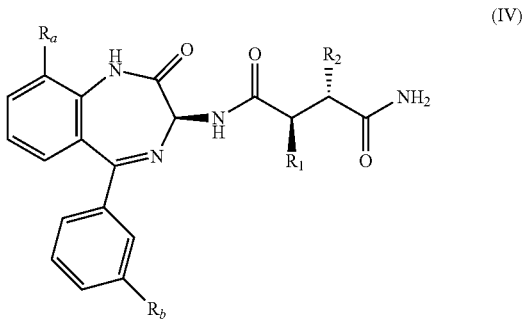

(IV)

In another embodiment, the present invention provides compositions comprising compounds represented by the structure of Formula (V):

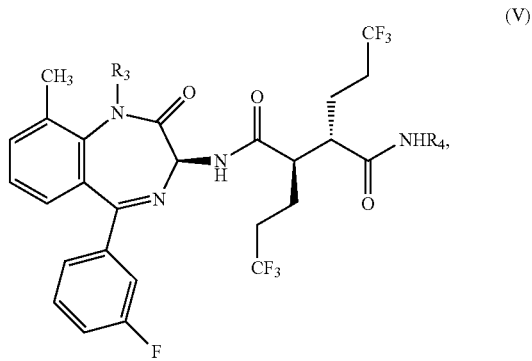

(V)

wherein $R_3$ is H or $R_x$.

In another embodiment, the present invention provides compositions comprising (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinamide (22); (2R,3S)—N-((3S)-5-(3-chlorophenyl)-9-ethyl-2-oxo-2,3-dihydro-1H-1,4-benzodiazepin-3-yl)-2,3-bis(3,3,3-trifluoropropyl)succinamide (23); (2R,3S)—N-((3S)-5-(3-chlorophenyl)-9-isopropyl-2-oxo-2,3-dihydro-1H-1,4-benzodiazepin-3-yl)-2,3-bis(3,3,3-trifluoropropyl)succinamide (24); (2R,3S)—N-(9-chloro-5-(3,4-dimethylphenyl)-2-oxo-2,3-dihydro-1H-1,4-benzodiazepin-3-yl)-3-(4,4,4-trifluorobutyl)-2-(3,3,3-trifluoropropyl)succinamide (25); (2R,3S)—N-(9-chloro-5-(3,5-dimethylphenyl)-2-oxo-2,3-dihydro-1H-1,4-benzodiazepin-3-yl)-3-(4,4,4-trifluorobutyl)-2-(3,3,3-trifluoropropyl)succinamide (26); (2R,3S)—N-((3S)-9-ethyl-5-(3-methylphenyl)-2-oxo-2,3-dihydro-1H-1,4-benzodiazepin-3-yl)-2,3-bis(3,3,3-trifluoropropyl)succinamide (27); (2R,3S)—N-((3S)-5-(3-chlorophenyl)-9-methyl-2-oxo-2,3-dihydro-1H-1,4-benzodiazepin-3-yl)-2,3-bis(3,3,3-trifluoropropyl)succinamide (28); (2R,3S)—N-((3S)-5-(3-chlorophenyl)-9-methyl-2-oxo-2,3-dihydro-1H-1,4-benzodiazepin-3-yl)-3-(4,4,4-trifluorobutyl)-2-(3,3,3-trifluoropropyl)succinamide (29); (2R,3S)—N-((3S)-5-(3-methylphenyl)-2-oxo-9-(trifluoromethyl)-2,3-dihydro-1H-1,4-benzodiazepin-3-yl)-2,3-bis(3,3,3-trifluoropropyl)succinamide (30); (2R,3S)—N-((3S)-9-chloro-5-(3,5-dimethylphenyl)-2-oxo-2,3-dihydro-1H-1,4-benzodiazepin-3-yl)-2,3-bis(3,3,3-trifluoropropyl)succinamide (31); (2R,3S)—N-((3S)-5-(3-methylphenyl)-2-oxo-9-(trifluoromethyl)-2,3-dihydro-1H-1,4-benzodiazepin-3-yl)-3-(4,4,4-trifluorobutyl)-2-(3,3,3-trifluoropropyl)succinamide (32); (2R,3S)—N-((3S)-9-isopropyl-5-(3-methylphenyl)-2-oxo-2,3-dihydro-1H-1,4-benzodiazepin-3-yl)-2,3-bis(3,3,3-trifluoropropyl)succinamide (33); (2R,3S)—N-((3S)-9-(cyclopropyloxy)-5-(3-methylphenyl)-2-oxo-2,3-dihydro-1H-1,4-benzodiazepin-3-yl)-3-(4,4,4-trifluorobutyl)-2-(3,3,3-trifluoropropyl)succinamide (34); (2R,3S)—N-((3S)-9-(cyclopropyloxy)-5-(3-methylphenyl)-2-oxo-2,3-dihydro-1H-1,4-benzodiazepin-3-yl)-2,3-bis(3,3,3-trifluoropropyl)succinamide (35); (2R,3S)—N-((3S)-9-chloro-5-(3-methylphenyl)-2-oxo-2,3-dihydro-1H-1,4-benzodiazepin-3-yl)-3-(4,4,4-trifluorobutyl)-2-(3,3,3-trifluoropropyl) succinamide (36); (2R,3S)—N-((3S)-9-methyl-2-oxo-5-(3-(trifluoromethyl)phenyl)-2,3-dihydro-1H-1,4-benzodiazepin-3-yl)-3-(4,4,4-trifluorobutyl)-2-(3,3,3-trifluoropropyl) succinamide (37); (2R,3S)—N-((3S)-9-methyl-2-oxo-5-(3-(trifluoromethyl)phenyl)-2,3-dihydro-1H-1,4-benzodiazepin-3-yl)-2,3-bis(3,3,3-trifluoropropyl)succinamide (38); (2R,3S)—N-((3S)-9-chloro-5-(2-methylphenyl)-2-oxo-2,3-dihydro-1H-1,4-benzodiazepin-3-yl)-2,3-bis(3,3,3-trifluoropropyl)succinamide (39); (2R,3S)—N-((3S)-5-(4-fluorophenyl)-9-methyl-2-oxo-2,3-dihydro-1H-1,4-benzodiazepin-3-yl)-2,3-bis(3,3,3-trifluoropropyl)succinamide (40); (2R,3S)—N-((3S)-9-chloro-5-(3-cyclopropylphenyl)-2-oxo-2,3-dihydro-1H-1,4-benzodiazepin-3-yl)-2,3-bis(3,3,3-trifluoropropyl)succinamide (41); (2R,3S)—N-((3S)-5-(3-chlorophenyl)-9-methoxy-2-oxo-2,3-dihydro-1H-1,4-benzodiazepin-3-yl)-2,3-bis(3,3,3-trifluoropropyl)succinamide (42); (2R,3S)—N-((3S)-5-(4-chlorophenyl)-9-methoxy-2-oxo-2,3-dihydro-1H-1,4-benzodiazepin-3-yl)-2,3-bis(3,3,3-trifluoropropyl)succinamide (43); (2R,3S)—N-((3S)-9-chloro-5-(3-methylphenyl)-2-oxo-2,3-dihydro-1H-1,4-benzodiazepin-3-yl)-2,3-bis(3,3,3-trifluoropropyl)succinamide (44); (2R,3S)—N-((3S)-5-(3-methylphenyl)-9-methoxy-2-oxo-2,3-dihydro-1H-1,4-benzodiazepin-3-yl)-2,3-bis(3,3,3-trifluoropropyl)succinamide (45); (2R,3S)—N-((3S)-5-(4-(hydroxymethyl)phenyl)-2-oxo-2,3-dihydro-1H-1,4-benzodiazepin-3-yl)-2,3-bis(3,3,3-trifluoropropyl)succinamide (46); (2R,3S)—N-((3S)-5-(2-methylphenyl)-2-oxo-2,3-dihydro-1H-1,4-benzodiazepin-3-yl)-2,3-bis(3,3,3-trifluoropropyl)succinamide (47); (2R,3S)—N-((3S)-5-(3-methylphenyl)-2-oxo-2,3-dihydro-1H-1,4-benzodiazepin-3-yl)-2,3-bis(3,3,3-trifluoropropyl)succinamide (48); (2R,3S)—N-((3S)-9-methoxy-2-oxo-5-(5-(trifluoromethyl)-2-pyridinyl)-2,3-dihydro-1H-1,4-benzodiazepin-3-yl)-2,3-bis(3,3,3-trifluoropropyl)succinamide (49); (2R,3S)—N-((3S)-5-(5-chloro-2-pyridinyl)-9-methoxy-2-oxo-2,3-dihydro-1H-1,4-benzodiazepin-3-yl)-2,3-bis(3,3,3-trifluoropropyl)succinamide (50); (2R,3S)—N-((3S)-5-(4-methoxyphenyl)-2-oxo-2,3-dihydro-1H-1,4-benzodiazepin-3-yl)-2,3-bis(3,3,3-trifluoropropyl)succinamide (51); (2R,3S)—N-((3S)-5-(4-methylphenyl)-2-oxo-2,3-dihydro-1H-1,4-benzodiazepin-3-yl)-2,3-bis(3,3,3-trifluoropropyl)succinamide (52); (2R,3S)—N-((3S)-5-(3-fluorophenyl)-9-(hydroxymethyl)-2-oxo-2,3-dihydro-1H-1,4-benzodiazepin-3-yl)-2,3-bis(3,3,3- trifluoropropyl)succinamide (53); ((3S)-3-(((2R,3S)-3-carbamoyl-6,6,6-trifluoro-2-(3,3,3-trifluoropropyl)hexanoyl)amino)-5-(3-fluorophenyl)-9-methyl-2-oxo-2,3-dihydro-1H-1,4-benzodiazepin-1-yl)methyl L-valinate (54); ((3S)-3-(((2R,3S)-3-carbamoyl-6,6,6-trifluoro-2-(3,3,3-trifluoropropyl)hexanoyl)amino)-5-(3-fluorophenyl)-9-methyl-2-oxo-2,3-dihydro-1H-1,4-benzodiazepin-1-yl)methyl L-alaninate (55); S-(((2S,3R)-6,6,6-trifluoro-3-(((3S)-5-(3-fluorophenyl)-9-methyl-2-oxo-2,3-dihydro-1H-1,4-benzodiazepin-3-yl)carbamoyl)-2-(3,3,3-trifluoropropyl)hexanoyl)amino)-L-cysteine (56); tert-butyl S-(((2S,3R)-6,6,6-trifluoro-3-(((3S)-5-(3-fluorophenyl)-9-methyl-2-oxo-2,3-dihydro-1H-1,4-benzodiazepin-3-yl)carbamoyl)-2-(3,3,3-trifluoropropyl)hexanoyl)amino)-L-cysteinate (57); methyl S-(((2S,3R)-6,6,6-trifluoro-3-(((3S)-5-(3-fluorophenyl)-9-methyl-2-oxo-2,3-dihydro-1H-1,4-benzodiazepin-3-yl)carbamoyl)-2-(3,3,3-trifluoropropyl) hexanoyl)amino)-L-cysteinate (58); ((3S)-3-(((2R,3S)-3-carbamoyl-6,6,6-trifluoro-2-(3,3,3-trifluoropropyl)hexanoyl)amino)-5-(3-fluorophenyl)-9-methyl-2-oxo-2,3-dihydro-1H-1,4-benzodiazepin-1-yl)methyl (4-(phosphonooxy)phenyl)acetate (59); and ((3S)-3-(((2R,3S)-3-carbamoyl-6,6,6-trifluoro-2-(3,3,3-trifluoropropyl)hexanoyl)amino)-5-(3-fluorophenyl)-9-methyl-2-oxo-2,3-dihydro-1H-1,4-benzodiazepin-1-yl)methyl L-valyl-L-valinate (60); and salts thereof.

In another embodiment, the present invention provides compositions comprising compounds represented by the structure of Formula (I):

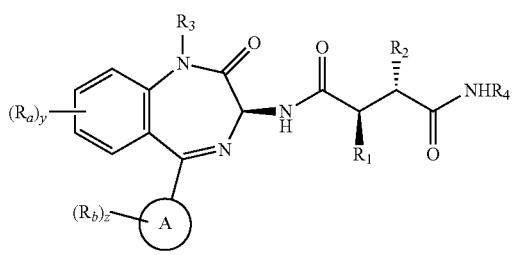

and/or at least one salt thereof, wherein:
$R_1$ is —$CH_2CF_3$ or —$CH_2CH_2CF_3$;
$R_2$ is —$CH_2CF_3$, —$CH_2CH_2CF_3$, or —$CH_2CH_2CH_2CF_3$;
$R_3$ is H, —$CH_3$ or $R_x$;
$R_4$ is H or $R_y$;
$R_x$ is: —$CH_2OC(O)CH(CH_3)NH_2$, —$CH_2OC(O)CH(NH_2)CH(CH_3)_2$, —$CH_2OC(O)CH((CH(CH_3)_2)NHC(O)CH(NH_2)CH(CH_3)_2$,

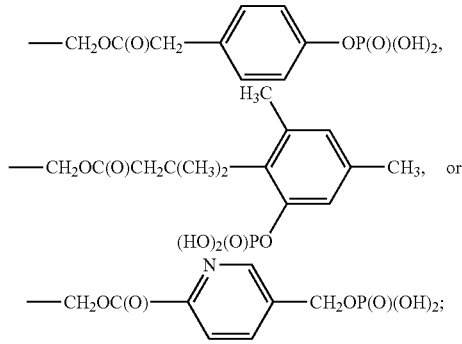

$R_y$ is: —$SCH_2CH(NH_2)C(O)OH$, —$SCH_2CH(NH_2)C(O)OCH_3$, or —$SCH_2CH(NH_2)C(O)OC(CH_3)_3$;

Ring A is phenyl or pyridinyl;
each $R_a$ is independently F, Cl, —CN, —$OCH_3$, $C_{1-3}$ alkyl, —$CH_2OH$, —$CF_3$, cyclopropyl, —$OCH_3$, —O(cyclopropyl) and/or —$NHCH_2CH_2OCH_3$;
each $R_b$ is independently F, Cl, —$CH_3$, —$CH_2OH$, —$CF_3$, cyclopropyl, and/or —$OCH_3$;
y is zero, 1 or 2; and
z is zero, 1, or 2
provided that if Ring A is phenyl, z is zero, and y is 1 or 2 then at least one $R_a$ is $C_{1-3}$ alkyl, —$CH_2OH$, —$CF_3$, cyclopropyl, or —O(cyclopropyl);
provided that if $R_3$ is $R_x$ then $R_4$ is H; and
provided that if $R_4$ is $R_y$ then $R_3$ is H or —$CH_3$.

In another embodiment, the structure as described hereinabove comprises one or more of the following provisos: provided that if Ring A is phenyl, z is zero, and y is 1 or 2 then at least one $R_a$ is $C_{1-3}$ alkyl, —$CH_2OH$, —$CF_3$, cyclopropyl, or —O(cyclopropyl); provided that if $R_3$ is $R_x$ then $R_4$ is H; and provided that if $R_4$ is $R_y$ then $R_3$ is H or —$CH_3$.

In another embodiment, the present invention provides compositions comprising compounds represented by the following structure:

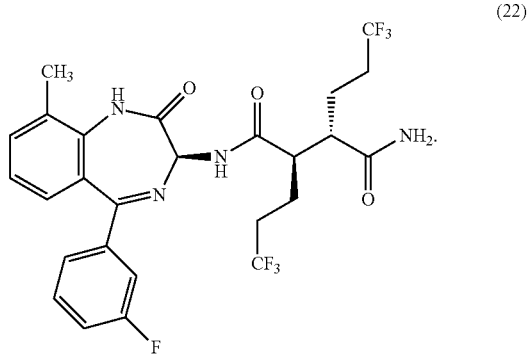 [SMILES: Cc1cccc2c1NC(=O)[C@@H](NC(=O)[C@H](CCC(F)(F)F)[C@H](CCC(F)(F)F)C(N)=O)N=C2c1cccc(F)c1]

In another embodiment, the compounds as described herein comprise prodrugs of one or more of the compounds.

U.S. Pat. No. 9,273,014, which is incorporated by reference herein in its entirety, discloses various compounds of Formula (I):

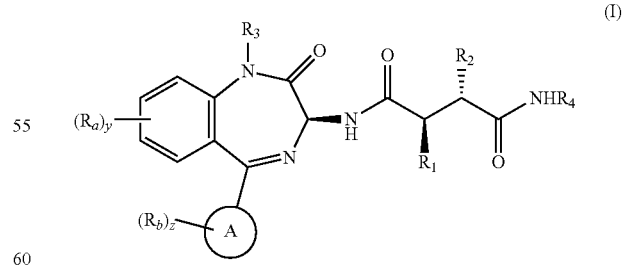

and/or at least one salt thereof, wherein:
$R_1$ is —$CH_2CH_2CF_3$;
$R_2$ is —$CH_2CH_2CF_3$ or —$CH_2CH_2CH_2CF_3$;
$R_3$ is H, —$CH_3$, or $R_x$;
$R_4$ is H or $R_y$;

$R_x$ is: —CH$_2$OC(O)CH(CH$_3$)NH$_2$, —CH$_2$OC(O)CH(NH$_2$)CH(CH$_3$)$_2$, —CH$_2$OC(O)CH((CH(CH$_3$)$_2$)NHC (O)CH(NH$_2$)CH(CH$_3$)$_2$,

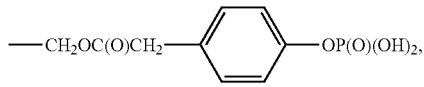

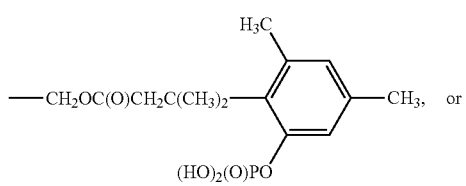

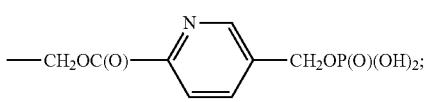

$R_y$ is: —SCH$_2$CH(NH$_2$)C(O)OH, —SCH$_2$CH(NH$_2$)C(O)OCH$_3$, or —SCH$_2$CH(NH$_2$)C(O)OC(CH$_3$)$_3$;

Ring A is phenyl or pyridinyl;

each $R_a$ is independently Cl, C$_{1-3}$ alkyl, —CH$_2$OH, —CF$_3$, cyclopropyl, —OCH$_3$, and/or —O(cyclopropyl);

each $R_b$ is independently F, Cl, —CH$_3$, —CH$_2$OH, —CF$_3$, cyclopropyl, and/or —OCH$_3$;

y is zero, 1, or 2; and z is 1 or 2.

U.S. Pat. No. 9,273,014 also discloses the compound of Formula (22):

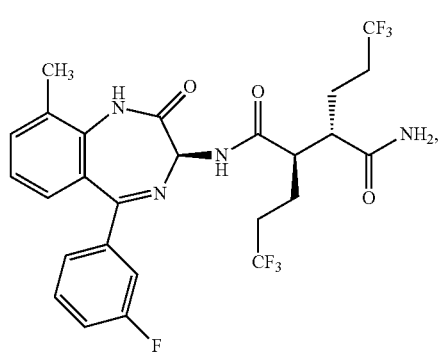

which, in one embodiment, has the chemical name (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinamide. U.S. Pat. No. 9,273,014 also discloses a process for synthesizing the compounds as well as other compounds of Formula (I), which are to be considered as part of the present invention.

U.S. Pat. No. 8,629,136, which is incorporated by reference herein in its entirety, discloses compounds of Formula (III):

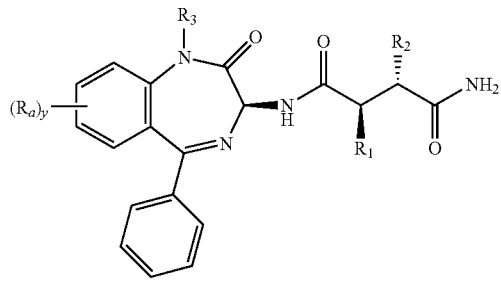

and/or at least one salt thereof, wherein:

$R_3$ is H or —CH$_3$; and each $R_a$ is independently F, Cl, —CN, —OCH$_3$ and/or —NHCH$_2$CH$_2$OCH$_3$.

U.S. Pat. No. 8,629,136 also discloses the compound of Formula (1):

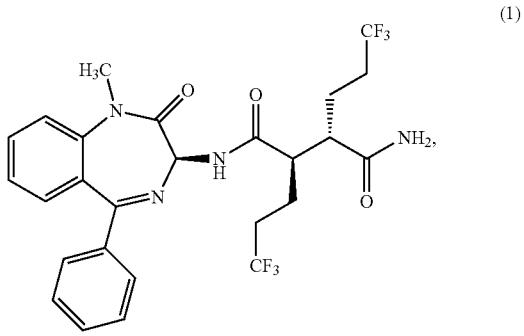 [SMILES: CN1C(=O)[C@@H](NC(=O)[C@H](CCC(F)(F)F)[C@H](CCC(F)(F)F)C(N)=O)N=C(c2ccccc2)c2ccccc21]

which, in one embodiment, has the chemical name (2R,3S)—N-((3S)-1-methyl-2-oxo-5-phenyl-2,3-dihydro-1H-1,4-benzodiazepin-3-yl)-2,3-bis(3,3,3-trifluoropropyl)succinamide. In one embodiment, the compounds are Notch inhibitors. U.S. Pat. No. 8,629,136 discloses a process for synthesizing the compounds as well as other compounds of Formula (I), which are to be considered as part of the present invention.

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe addition more embodiments. It is also to be understood that each individual element of the embodiments is meant to be combined with any and all other elements from any embodiment to describe an additional embodiment.

Combined Treatments

In one embodiment, the present invention provides compositions comprising compounds represented by the structure of Formula (I) as described herein as monotherapy or in a combination therapy with one or more anti-cancer agents.

In another embodiment, the present invention provides compositions comprising compounds represented by the structure of Formula (I) as described herein as monotherapy or in a combination therapy with one or more chemotherapeutic agents.

In one embodiment, the present invention provides a composition comprising one or more compounds represented by the structure of Formula (III) as monotherapy or in a combination therapy with one or more anti-cancer agents:

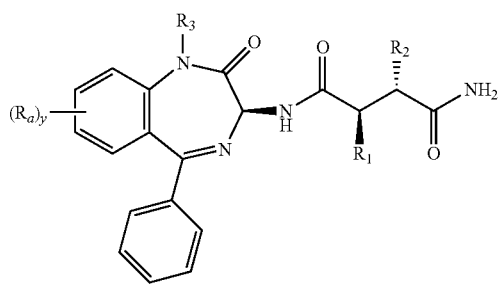

or prodrugs or salts thereof; wherein:
$R_1$ is —$CH_2CF_3$ or —$CH_2CH_2CF_3$;
$R_2$ is —$CH_2CF_3$, —$CH_2CH_2CF_3$, or —$CH_2CH_2CH_2CF_3$;
$R_3$ is H or —$CH_3$;
each $R_a$ is independently F, Cl, —CN, —$OCH_3$, and/or —$NHCH_2CH_2OCH_3$; and
y is zero, 1, or 2.

In one embodiment, the present invention provides a composition comprising one or more compounds represented by the structure of Formula (III) as monotherapy or in a combination therapy with one or more chemotherapeutic agents:

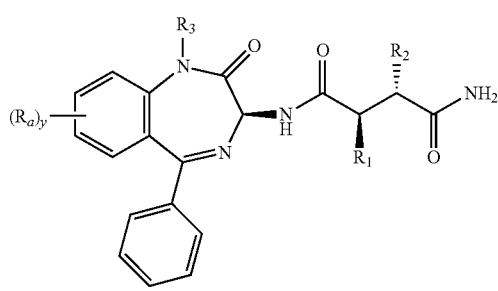

or prodrugs or salts thereof; wherein:
$R_1$ is —$CH_2CF_3$ or —$CH_2CH_2CF_3$;
$R_2$ is —$CH_2CF_3$, —$CH_2CH_2CF_3$, or —$CH_2CH_2CH_2CF_3$;
$R_3$ is H or —$CH_3$;
each $R_a$ is independently F, Cl, —CN, —$OCH_3$, and/or —$NHCH_2CH_2OCH_3$; and
y is zero, 1, or 2.

In one embodiment, compositions of the present invention or for use in the methods of the present invention comprise one or more cancer therapeutic agents in a combination therapy with one or more bisfluoroalkyl-1,4-benzodiazepinone compounds described hereinabove.

In treating cancer, a combination of chemotherapeutic agents and/or other treatments (e.g., radiation therapy) is often advantageous. An additional agent may have the same or different mechanism of action than the primary therapeutic agents. For example, drug combinations may be employed wherein the two or more drugs being administered act in different manners or in different phases of the cell cycle, and/or where the two or more drugs have nonoverlapping toxicities or side effects, and/or where the drugs being combined each has a demonstrated efficacy in treating the particular disease state manifested by the patient.

In another embodiment, the present invention provides a composition comprising one or more compounds represented by the structure of Formula (I) as described herein in combination with Eribulin.

In another embodiment, the present invention provides a composition comprising one or more compounds represented by the structure of Formula (I) as described herein in combination with vinorelbine.

In another embodiment, the present invention provides a composition comprising one or more compounds represented by the structure of Formula (I) as described herein in combination with FOLFIRI. In one embodiment, FOLFIRI comprises folinic acid (leucovorin), fluorouracil (5-FU) and irinotecan (CAMPTOSAR®). In another embodiment, the present invention provides a composition comprising one or more compounds represented by the structure of Formula (I) as described herein and folinic acid (leucovorin), fluorouracil (5-FU), irinotecan (CAMPTOSAR®), or a combination thereof.

In one embodiment, a composition of the present invention comprises one or more compounds represented by the structure of Formula (I) as described herein and one or more targeted therapeutics. In one embodiment, said targeted therapeutic comprises an inhibitor of mammalian target of rapamycin (mTOR). In one embodiment, the mTOR inhibitor comprises Everolimus. In another embodiment, the mTOR inhibitor comprises sirolimus (rapamycin). In another embodiment, the mTOR inhibitor comprises temsirolimus.

In another embodiment, the mTOR inhibitor comprises a dual mammalian target of rapamycin/phosphoinositide 3-kinase inhibitor, which in one embodiment, comprises NVP-BEZ235 (dactolisib), GSK2126458, XL765, or a combination thereof.

In another embodiment, the mTOR inhibitor comprises a second generation mTOR inhibitor, which, in one embodiment, comprises AZD8055, INK128/MLN0128, OSI027, or a combination thereof.

In another embodiment, the mTOR inhibitor comprises a third generation mTOR inhibitor, which, in one embodiment, comprises RapaLinks.

In one embodiment, a composition of the present invention comprises one or more compounds represented by the structure of Formula (I) as described herein in combination with an mTOR inhibitor and a chemotherapeutic drug. In one embodiment, the mTOR inhibitor comprises everolimus. In one embodiment, the chemotherapeutic drug comprises cisplatin.

In one embodiment, a composition of the present invention comprises one or more compounds represented by the structure of Formula (I) as described herein in combination with a PARP (poly ADP-ribose polymerase) inhibitor.

In another embodiment, a composition of the present invention comprises one or more compounds represented by the structure of Formula (I) as described herein and a polyfunctional alkylating agent. In one embodiment, the polyfunctional alkylating agent comprises a Nitrosourea, Mustard, Nitrogen Mustard, Methanesulphonate, Busulphan, Ethylenimine, or a combination thereof.

In another embodiment, a composition of the present invention comprises one or more compounds represented by the structure of Formula (I) as described herein in combination with steroids.

In another embodiment, a composition of the present invention comprises one or more compounds represented by the structure of Formula (I) as described herein in combination with bisphosphonates.

In another embodiment, a composition of the present invention comprises one or more compounds represented by the structure of Formula (I) as described herein in combination with cancer growth blockers.

In another embodiment, a composition of the present invention comprises one or more compounds represented by the structure of Formula (I) as described herein in combination with proteasome inhibitors.

In another embodiment, a composition of the present invention comprises one or more compounds represented by the structure of Formula (I) as described herein in combination with one or more interferons.

In another embodiment, a composition of the present invention comprises one or more compounds represented by the structure of Formula (I) as described herein in combination with one or more interleukins.

In another embodiment, the present invention provides a composition comprising one or more compounds represented by the structure of Formula (I) as described herein and an alkylating drug. In one embodiment, the alkylating drug comprises Procarbazine (MATULANE®), Dacarbazine (DTIC), Altretamine (HEXALEN®), or a combination thereof.

In another embodiment, the present invention provides a composition comprising one or more compounds represented by the structure of Formula (I) as described herein and an alkylating-like drug. In one embodiment, the alkylating-like drug comprises Cisplatin (PLATINOL®).

In another embodiment, the present invention provides a composition comprising one or more compounds represented by the structure of Formula (I) as described herein and an antimetabolite. In one embodiment, the antimetabolite comprises an antifolic acid compound (Methotrexate), an amino acid antagonists (Azaserine), or a combination thereof.

In another embodiment, the present invention provides a composition comprising one or more compounds represented by the structure of Formula (I) as described herein and a purine antagonist. In one embodiment, the purine antagonist comprises Mercaptopurine (6-MP), Thioguanine (6-TG), Fludarabine Phosphate, Cladribine (LEUSTATIN®), Pentostatin (NIPENT™), or a combination thereof.

In another embodiment, the present invention provides a composition comprising one or more compounds represented by the structure of Formula (I) as described herein and a pyrimidine antagonist. In one embodiment, the pyrimidine antagonist comprises Fluorouracil (5-FU), Cytarabine (ARA-C), Azacitidine, or a combination thereof.

In another embodiment, the present invention provides a composition comprising one or more compounds represented by the structure of Formula (I) as described herein and a plant alkaloid. In one embodiment, the plant alkaloid comprises Vinblastine (VELBAN®), Vincristine (ONCOVIN®), Etoposide (VP-16, VEPE-SID®), Teniposide (VUMON®), Topotecan (HYCAMTIN®), Irinotecan (CAMPTOSAR®), Paclitaxel (TAXOL®), Docetaxel (TAXOTERE®), or a combination thereof.

In another embodiment, the present invention provides a composition comprising one or more compounds represented by the structure of Formula (I) as described herein and an antibiotic. In one embodiment, the antibiotic comprises Anthracyclines, Doxorubicin (ADRIAMYCIN®, RUBEX®, DOXIL®), Daunorubicin (DAUNOXOME®), Dactinomycin (COSMEGEN®), Idarubincin (IDAMYCIN®), Plicamycin (MITHRAMYCIN®), Mitomycin (MUTAMYCIN®), Bleomycin (BLENOXANE®), or a combination thereof.

In another embodiment, the present invention provides a composition comprising one or more compounds represented by the structure of Formula (I) as described herein in combination with a cancer vaccine. In another embodiment, the present invention provides a composition comprising one or more compounds represented by the structure of Formula (I) as described herein and an immunotherapeutic. In one embodiment, the immunotherapeutic comprises a monoclonal antibody. In one embodiment, the monoclonal antibody comprises an anti-PD-1 antibody, which in one embodiment comprises nivolumab.

In another embodiment, the monoclonal antibody comprises alemtuzumab (CAMPATH©), trastuzumab (HERCEPTIN®), Bevacizumab (AVASTIN®), Cetuximab (ERBITUX®), or a combination thereof. In another embodiment, the monocolonal antibody comprises a radiolabeled antibody, which, in one embodiment, comprises britumomab, tiuxetan (ZEVALIN®), or a combination thereof. In another embodiment, the monocolonal antibody comprises a chemolabeled antibody, which in one embodiment comprises Brentuximab vedotin (ADCETRIS©), Ado-trastuzumab emtansine (KADCYLA©, also called TDM-1), denileukin diftitox (ONTAK©), or a combination thereof. In another embodiment, the monocolonal antibody comprises a bispecific antibody, which in one embodiment, comprises blinatumomab (BLINCYTO©).

In another embodiment, the present invention provides a composition comprising one or more compounds represented by the structure of Formula (I) as described herein in combination with a hormonal therapy. In another embodiment, the present invention provides a composition comprising one or more compounds represented by the structure of Formula (I) as described herein and a hormonal agent. In one embodiment, the hormonal agent comprises Tamoxifen (NOLVADEX©), Flutamide (EULEXIN©), Gonadotropin-Releasing Hormone Agonists, (Leuprolide and Goserelin (ZOLADEX©)), Aromatase Inhibitors, Aminoglutethimide, Anastrozole (ARIMIDEX©), or a combination thereof.

In another embodiment, the present invention provides a composition comprising one or more compounds represented by the structure of Formula (I) as described herein and Amsacrine, Hydroxyurea (Hydrea), Asparaginase (ELSPAR©), Mitoxantrone (NOVANTRONE©), Mitotane, Retinoic Acid Derivatives, Bone Marrow Growth Factors, Amifostine, or a combination thereof.

In another embodiment, the present invention provides a composition comprising one or more compounds represented by the structure of Formula (I) as described herein in combination with an agent that inhibits one or more cancer stem cell pathways. In one embodiment, such agent comprises an inhibitor of Hedgehog, WNT, BMP, or a combination thereof.

In one embodiment, said anti-cancer agent comprises a BCMA-targeted chimeric antigen receptor T-cell immunotherapeutic, p53-HDM2 inhibitor, c-MET inhibitor, BCR-ABL inhibitor, Anti-interleukin-1 beta monoclonal antibody, EGFR mutation modulator, PI3K-alpha inhibitor, JAK1/2 inhibitor, Cortisol synthesis inhibitor, Thrombopoietin, P-selectin inhibitor receptor agonist, Anti-CD20 monoclonal antibody, Anti-PD-1 monoclonal antibody, Signal transduction inhibitor, CDK4/6 inhibitor, BRAF inhibitor+MEK inhibitor, CD19-targeted chimeric antigen receptor T-cell immunotherapeutic, Somatostatin analogue, or a combination thereof. In one embodiment, said anti-cancer agent comprises capmatinib, asciminib, canakinumab, alpelisib, ruxolitinib, osilodrostat, eltrombopag, crizanlizumab, ofatumumab, spartalizumab, midostaurin, ribociclib, dabrafenib+trametinib, tisagenlecleucel, everolimus, pasireotide, or a combination thereof.

In another embodiment, the present invention provides a composition comprising one or more compounds represented by the structure of Formula (I) as described herein in combination with a hematopoietic stem cell transplant approach.

In another embodiment, the present invention provides a composition comprising one or more compounds represented by the structure of Formula (I) as described herein in combination with isolated infusion approaches. In one embodiment, the isolated infusion approach comprises infusion of chemotherapy into a specific tissue in order to deliver a very high dose of chemotherapy to tumor sites without causing overwhelming systemic damage.

In another embodiment, the present invention provides a composition comprising one or more compounds represented by the structure of Formula (I) as described herein in combination with targeted delivery mechanisms. In one embodiment, the targeted delivery mechanism increases effective levels of chemotherapy for tumor cells while reducing effective levels for other cells for increased tumor specificity and/or reduced toxicity. In one embodiment, targeted delivery mechanisms comprise a traditional chemotherapeutic agent, or a radioisotope or an immune stimulating factor.

In another embodiment, the present invention provides a composition comprising one or more compounds represented by the structure of Formula (I) as described herein in combination with nanoparticles. In one embodiment, nanoparticles are used as a vehicle for poorly-soluble agents such as paclitaxel. In one embodiment, nanoparticles made of magnetic material can also be used to concentrate agents at tumour sites using an externally applied magnetic field.

In another embodiment, the present invention provides a composition comprising one or more compounds represented by the structure of Formula (I) as described herein in combination with an agent for treating Adenoid Cystic Carcinoma (ACC). In one embodiment, said agent for treating ACC comprises Axitinib, Bortezomib (VELCADE®), Bortezomib+doxorubicin, Cetuximab, Cetuximab+Intensity modulated radiation therapy (IMRT), Cetuximab+RT+cisplatin, Cetuximab+cisplatin+5-FU, Chidamide (CS055/HBI-8000), Cetuximab & Carbon Ion, Cisplatin, cisplatin & 5-FU, Cisplatin & Doxorubicin & Bleomycin, Cisplatin & Doxorubicin & Cyclophosphamide, Dasatinib, Dovitinib, Epirubicin, Gefitinib, Gemcitabine, Gemcitabine & Cisplatin, Imatinib, Imatinib+cisplatin, Lapatinib, Mitoxanthrone, MK 2206, Nelfinavir, Paclitaxel, Paclitaxel & Carboplatin, Panitumumab & Radiotherapy, PF-00562271, PF-00299804 & Figitumumab PX-478, PX-866, Regorafenib, Sonepcizumab, Sorafenib, Sunitinib, Vinorelbine, Vinorelbine & Cisplatin, Vorinostat, XL147 & Erlotinib, XL647, or combinations thereof.

In another embodiment, the present invention provides a composition comprising one or more compounds represented by the structure of Formula (I) as described herein in combination with pembrolizumab, docetaxel, nivolumab and ipilimumab, PSMA-PET Imaging, chidamide, APG-115, HDM201, DS-3032b, LY3039478, or a combination thereof.

In another embodiment, the present invention provides a composition comprising one or more compounds represented by the structure of Formula (I) as described herein in combination with an agent for treating triple negative breast cancer. In one embodiment, said agent for treating triple-negative breast cancer comprises PARP (poly ADP-ribose polymerase) inhibitors such as olaparib, VEGF (vascular endothelial growth factor) inhibitors such as bevacizumab, EGFR (epidermal growth factor receptor)-targeted therapies such as cetuximab, or a combination thereof.

In one embodiment, a method is provided for treating cancer comprising administering to a mammal in need thereof a composition as described herein and administering one or more anti-cancer agents.

In one embodiment, the phrase "anti-cancer agent" refers to a drug selected from any one or more of the following: alkylating agents (including mustard, nitrogen mustards, methanesulphonate, busulphan, alkyl sulfonates, nitrosoureas, ethylenimine derivatives, and triazenes or combinations thereof); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/ab1, cyclin dependent kinase [CDK] inhibitors, panHer, Her-1 and Her-2 antibodies, VEGF inhibitors, including anti-VEGF antibodies, EGFR inhibitors, PARP (poly ADP-ribose polymerase) inhibitors, mitogen-activated protein [MAP]inhibitors, MET inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, Platinum-based antineoplastic drugs (platins) such as cisplatin, carboplatin, oxaliplatin, nedaplatin, triplatin tetranitrate, phenanthriplatin, picoplatin and satraplatin and the naturally-occurring epothilones and their synthetic and semi-synthetic analogs; microtubule-binding, destabilizing agents (including *vinca* alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

In another embodiment, the present invention provides a composition comprising one or more compounds represented by the structure of Formula (I) as described herein in combination with any one or more of the following: REVLIMID®, AVASTIN®, HERCEPTIN®, RITUXAN®, OPDIVO®, GLEEVEC®, IMBRUVICA®, VELCADE®, ZYTIGA®, XTANDI®, ALIMTA®, GARDASIL®, IBRANCE®, PERJETA®, TASIGNA®, XGEVA®, AFINITOR®, JAKAFI®, TARCEVA®, KEYTRUDA®, SUTENT®, YERVOY®, NEXAVAR®, ZOLADEX®, ERBITUX®, DARZALEX®, XELODA®, GAZYVA®, VENCLEXTA®, and TECENTRIQ®.

In another embodiment, the present invention provides a composition comprising one or more compounds represented by the structure of Formula (1) as described herein in combination with any one or more of the following: abemaciclib, epacadostat, apalutamide, Carfilzomib, Crizotinib (PF-02341066), GDC-0449 (vismodegib), ONCO-VEX$^{GM-CSF}$ (talimogene laherparepvec), PLX4032 (RG7204), Ponatinib, SGN-35 (brentuximab vedotin), Tivozanib (AV-951), T-DM1 (Trastuzumab-DM1), and XL184 (cabozantinib).

Accordingly, the compositions of the present invention may be administered in combination with other anti-cancer treatments useful in the treatment of cancer or other proliferative diseases. The invention herein further comprises use of the compositions of the present invention in preparing medicaments for the treatment of cancer, and/or it comprises the packaging of the compositions of the present invention together with instructions that the compositions be used in combination with other anti-cancer or cytotoxic agents and treatments for the treatment of cancer.

In one embodiment, any of the methods as described herein comprises the step of administering to a subject a composition comprising compounds represented by the structure of Formula (I) as described herein as monotherapy or in a combination therapy with one or more anti-cancer agents. In another embodiment, any of the methods as described herein comprises the step of administering to a subject a composition comprising compounds represented by the structure of Formula (I) as described herein as monotherapy or in a combination therapy with one or more chemotherapeutic agents.

In another embodiment, any of the methods as described herein comprises the step of administering to a subject a composition comprising compounds represented by the structure of Formula (III) as described herein as monotherapy or in a combination therapy with one or more anti-cancer agents. In another embodiment, any of the methods as described herein comprises the step of administering to a subject a composition comprising compounds represented by the structure of Formula (III) as described herein as monotherapy or in a combination therapy with one or more chemotherapeutic agents.

In one embodiment, the anti-cancer or chemotherapeutic agent(s) in the methods of the present invention are administered to the subject in a single composition with a compound represented by the structure of Formula (I) or a compound represented by the structure of Formula (III). In another embodiment, the anti-cancer or chemotherapeutic agent(s) are administered to the subject in separate compositions from the composition comprising a compound represented by the structure of Formula (I) or a compound represented by the structure of Formula (III). In one embodiment, the separate compositions are administered to the subject at the same time. In another embodiment, the separate compositions are administered to the subject at separate times, at separate sites of administration, or a combination thereof.

In one embodiment, a method is provided for treating cancer comprising administering to a mammal in need thereof a compound of Formula (I); administering cisplatin; and optionally, administering one or more additional anti-cancer agents.

In one embodiment, a method is provided for treating cancer comprising administering to a mammal in need thereof a compound of Formula (I); administering dasatinib; and optionally, administering one or more additional anti-cancer agents.

In one embodiment, a method is provided for treating cancer comprising administering to a mammal in need thereof a compound of Formula (I); administering paclitaxel; and optionally, administering one or more additional anti-cancer agents.

In one embodiment, a method is provided for treating cancer comprising administering to a mammal in need thereof a compound of Formula (I); administering tamoxifen; and optionally, administering one or more additional anti-cancer agents.

In one embodiment, a method is provided for treating cancer comprising administering to a mammal in need thereof a compound of Formula (I), administering a glucocorticoid; and optionally, administering one or more additional anti-cancer agents. An example of a suitable glucocorticoid is dexamethasone.

In one embodiment, a method is provided for treating cancer comprising administering to a mammal in need thereof a compound of Formula (I), administering carboplatin; and optionally, administering one or more additional anti-cancer agents.

The compounds of the present invention can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

In one embodiment, pharmaceutical compositions are provided comprising a compound of Formula (I) or prodrug thereof; one or more additional agents selected from a kinase inhibitory agent (small molecule, polypeptide, and antibody), an immunosuppressant, an anti-cancer agent, an anti-viral agent, anti-inflammatory agent, antifungal agent, antibiotic, or an anti-vascular hyperproliferation compound; and any pharmaceutically acceptable carrier, adjuvant or vehicle.

The above other therapeutic agents, when employed in combination with the compounds of the present invention, may be used, for example, in those amounts indicated in the Physicians' Desk Reference (PDR) or as otherwise determined by one of ordinary skill in the art.

Pharmaceutical Compositions
Formulations

Also embraced within this invention is a class of pharmaceutical compositions comprising the compound of Formula (I) and one or more non-toxic, pharmaceutically acceptable carriers and/or diluents and/or adjuvants (collectively referred to herein as "carrier" materials) and, if desired, other active ingredients.

The compounds of Formula (I) may be administered by any suitable route, preferably in the form of a pharmaceutical composition adapted to such a route, and in a dose effective for the treatment intended. The compounds and compositions of the present invention may, for example, be administered in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 1 to 2000 mg, preferably from about 1 to 500 mg, and more preferably from about 5 to 150 mg. A suitable daily dose for a human or other mammal may vary widely depending on the condition of the patient and other factors, but can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

In another embodiment, the compounds of Formula (I) can be formulated as a nanoparticle, lipid nanoparticle, microparticle or liposome.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions. For example, the composition may be provided for intravenous administration comprising an amount of active ingredient in the range of from about 0.2 to 150 mg. In another embodiment, the active ingredient is present in the range of from about 0.3 to 10 mg. In another embodiment, the active ingredient is present in the range of from about 4 to 8.4 mg. In one embodiment, the active ingredient is administered at a dose of about 4 mg. In another embodiment, the active ingredient is administered at a dose of about 6 mg. In another embodiment, the active ingredient is administered at a dose of about 8.4 mg.

In another embodiment, the active ingredient is administered at a dose of about 0.3 mg. In another embodiment, the active ingredient is administered at a dose of about 0.6 mg. In another embodiment, the active ingredient is administered at a dose of about 1.2 mg. In another embodiment, the active ingredient is administered at a dose of about 2.4 mg.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, gender, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.005 and about 50 mg/kg body weight and most preferably between about 0.01 to 10 mg/kg body weight, may be appropriate.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and/or at least one salt thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The compound in accordance with Formula (I) can be administered by any means suitable for the condition to be treated, which can depend on the need for site-specific treatment or quantity of Formula (I) compound to be delivered. The compounds and compositions of the present invention may, for example, be administered orally, mucosally, or parentally including intravascularly, intraperitoneally, subcutaneously, intramuscularly, and intrasternally. In one embodiment, the compounds and compositions of the present invention are administered intravenously.

Methods of Use

In one embodiment, the present invention provides the use of the described compounds or compositions for treating, suppressing or inhibiting a proliferative disease in a subject.

In another embodiment, the present invention provides a method of treating, suppressing or inhibiting a proliferative disease in a subject, comprising the step of administering to said subject a composition comprising one or more compounds of Formula (I) and/or at least one salt thereof,

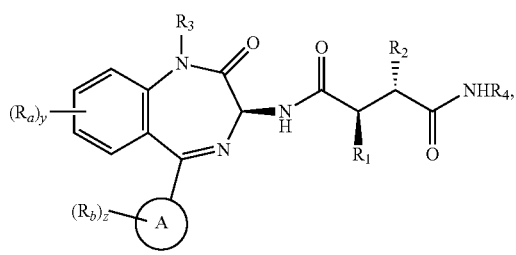

(I)

wherein:
$R_1$ is —$CH_2CF_3$ or —$CH_2CH_2CF_3$;
$R_2$ is —$CH_2CF_3$, —$CH_2CH_2CF_3$, or —$CH_2CH_2CH_2CF_3$;
$R_3$ is H, —$CH_3$ or $R_x$;
$R_4$ is H or $R_y$;
$R_x$ is: —$CH_2OC(O)CH(CH_3)NH_2$, —$CH_2OC(O)CH(NH_2)CH(CH_3)_2$, —$CH_2OC(O)CH((CH(CH_3)_2)NHC(O)CH(NH_2)CH(CH_3)_2$,

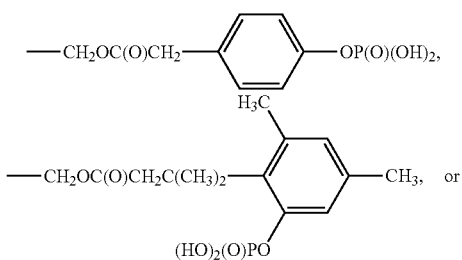

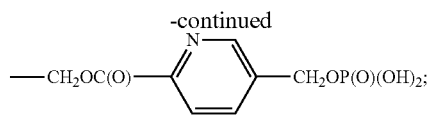

$R_y$ is: —$SCH_2CH(NH_2)C(O)OH$, —$SCH_2CH(NH_2)C(O)OCH_3$, or —$SCH_2CH(NH_2)C(O)OC(CH_3)_3$;
Ring A is phenyl or pyridinyl;
each $R_a$ is independently F, Cl, —CN, —$OCH_3$, $C_{1-3}$ alkyl, —$CH_2OH$, —$CF_3$, cyclopropyl, —$OCH_3$, —O(cyclopropyl) and/or —$NHCH_2CH_2OCH_3$;
each $R_b$ is independently F, Cl, —$CH_3$, —$CH_2OH$, —$CF_3$, cyclopropyl, and/or —$OCH_3$;
y is zero, 1 or 2; and
z is zero, 1, or 2.

In another embodiment, the present invention provides a method of treating, suppressing or inhibiting a proliferative disease in a subject, comprising the step of administering to said subject a composition comprising one or more compounds of Formula (III):

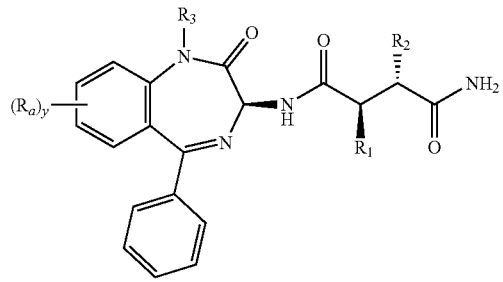

wherein:
$R_1$ is —$CH_2CF_3$ or —$CH_2CH_2CF_3$;
$R_2$ is —$CH_2CF_3$, —$CH_2CH_2CF_3$, or —$CH_2CH_2CH_2CF_3$;
$R_3$ is H or —$CH_3$;
each $R_a$ is independently F, Cl, —CN, —$OCH_3$, and/or —$NHCH_2CH_2OCH_3$; and
y is zero, 1, or 2.

In one embodiment, the compound is administered at a dose of approximately 0.3, 0.6, 1.2, 2.4, 4, 6, or 8.4 mg. In one embodiment, the compound is administered intravenously at a dose of approximately 0.3, 0.6, 1.2, 2.4, 4, 6, or 8.4 mg. In another embodiment, the compound is administered weekly at a dose of approximately 0.3, 0.6, 1.2, 2.4, 4, 6, or 8.4 mg.

In another embodiment, the present invention provides a method of treating, suppressing or inhibiting a proliferative disease in a subject comprising the step of administering to said subject a composition comprising one or more compounds represented by the structure of Formula (I) as described hereinabove, wherein said compound is administered at a dose of about 4 mg. In one embodiment, the compound is administered intravenously at a dose of approximately 4 mg. In another embodiment, the compound is administered weekly at a dose of approximately 4 mg.

In another embodiment, the present invention provides a method of treating, suppressing or inhibiting a proliferative disease in a subject comprising the step of administering to said subject a composition consisting essentially of one or more compounds represented by the structure of Formula (I) as described hereinabove. In another embodiment, the present invention provides a method of treating, suppressing or inhibiting a proliferative disease in a subject comprising the step of administering to said subject a composition consisting of one or more compounds represented by the structure of Formula (I) as described hereinabove.

In one embodiment, the present invention provides the use of a therapeutically acceptable amount of one or more compounds or compositions as described herein for treating, suppressing or inhibiting a proliferative disease in a subject. In another embodiment, the present invention provides the use of a therapeutically effective amount of one or more compounds or compositions as described herein for treating, suppressing or inhibiting a proliferative disease in a subject. In another embodiment, the present invention provides the use of a synergistically effective amount of one or more compounds or compositions as described herein for treating, suppressing or inhibiting a proliferative disease in a subject. In another embodiment, the present invention provides the use of a synergistically therapeutically effective amount of one or more compounds or compositions as described herein for treating, suppressing or inhibiting a proliferative disease in a subject.

In one embodiment, the proliferative disease comprises a Desmoid tumor.

In one embodiment, the proliferative disease comprises a pre-cancerous condition or a benign proliferative disorder.

In one embodiment, the term "pre-cancerous" or, alternatively, "pre-malignant" as used herein interchangeably refers to diseases, syndromes or other conditions associated with an increased risk of cancer. Pre-cancerous conditions in the context of the present invention include, but are not limited to: breast calcifications, vaginal intra-epithelial neoplasia, Barrett's esophagus, atrophic gastritis, dyskeratosis congenital, sideropenic dysphagia, lichen planus, oral submucous fibrosis, actinic keratosis, solar elastosis, cervical dysplasia, leukoplakia and erythroplakia.

In one embodiment, the term "benign hyperproliferative disorder" as used herein refers to a condition in which there is an abnormal growth and differentiation of cells and an increase in the amount of organic tissue that results from cell proliferation. The benign hyperproliferative disorder may be attributed to lack of response or inappropriate response to regulating factors, or alternatively to dysfunctional regulating factors. Non-limiting examples of benign hyperproliferative disorder are psoriasis and benign prostatic hyperplasia (BPH).

In another embodiment, the proliferative disease comprises a cancer.

In one embodiment, the cancer comprises a solid tumor. In another embodiment, the cancer comprises a hematological malignancy.

In one embodiment, a subject as described herein has cancer. In one embodiment, the term "cancer" in the context of the present invention includes all types of neoplasm whether in the form of solid or non-solid tumors and includes both malignant and premalignant conditions as well as their metastasis.

In one embodiment, the cancer is a carcinoma, sarcoma, myeloma, leukemia, or lymphoma. In another embodiment, the cancer is a mixed type.

In one embodiment, mixed type cancers comprise several types of cells. The type components may be within one category or from different categories. Some examples are: adenosquamous carcinoma; mixed mesodermal tumor; carcinosarcoma; teratocarcinoma In another embodiment, the carcinoma comprises Adenoid Cystic Carcinoma (ACC).

In another embodiment, the carcinoma comprises Gastro-esophageal junction carcinoma.

In one embodiment, the carcinoma is an adenocarcinoma. In another embodiment, the carcinoma is a squamous cell carcinoma.

In one embodiment, the sarcoma comprises osteosarcoma or osteogenic sarcoma (bone); Chondrosarcoma (cartilage); Leiomyosarcoma (smooth muscle); Rhabdomyosarcoma (skeletal muscle); Mesothelial sarcoma or mesothelioma (membranous lining of body cavities); Fibrosarcoma (fibrous tissue); Angiosarcoma or hemangioendothelioma (blood vessels); Liposarcoma (adipose tissue); Glioma or astrocytoma (neurogenic connective tissue found in the brain); Myxosarcoma (primitive embryonic connective tissue); and Mesenchymous or mixed mesodermal tumor (mixed connective tissue types).

In one embodiment, the cancer comprises myeloma, which, in one embodiment, is cancer that originates in the plasma cells of bone marrow. The plasma cells produce some of the proteins found in blood. In one embodiment, the cancer comprises multiple myeloma.

In another embodiment, the cancer comprises leukemia ("non-solid tumor" or "blood cancer"), which in one embodiment, is a cancer of the bone marrow (the site of blood cell production). In one embodiment, leukemia comprises myelogenous or granulocytic leukemia (malignancy of the myeloid and granulocytic white blood cell series); Lymphatic, lymphocytic, or lymphoblastic leukemia (malignancy of the lymphoid and lymphocytic blood cell series); and Polycythemia vera or erythremia (malignancy of various blood cell products, but with red cells predominating).

In another embodiment, the cancer comprises T-cell acute lymphoblastic leukemia (T-ALL). In another embodiment, the cancer comprises T-lymphoblastic leukemia/lymphoma (TLL). In another embodiment, the cancer comprises Chronic Lymphocytic Leukemia (CLL).

In another embodiment, the cancer comprises a lymphoma. In one embodiment, the lymphoma comprises an extranodal lymphoma. In one embodiment, the lymphoma comprises a Hodgkin lymphoma. In another embodiment, the lymphoma comprises a Non-Hodgkin lymphoma. In one embodiment, the lymphoma comprises a marginal zone B cell lymphoma, a diffuse large B cell lymphoma, or a mantle cell lymphoma.

In another embodiment, the cancer is dependent upon Notch activation. In another embodiment, the cancer comprises a Notch-activating mutation. In another embodiment, the cancer is not dependent upon Notch activation.

In one embodiment, the present invention provides a method of treating cancer, wherein said cancer comprises one or more Notch-activating genetic alterations, comprising the step of administering to said subject a composition comprising one or more compounds represented by the structure of Formula (I) and/or at least one salt thereof,

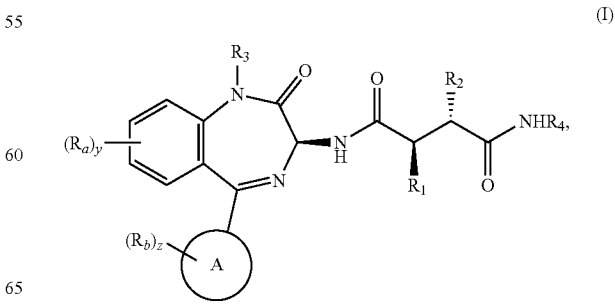

(I)

wherein:
R₁ is —CH₂CF₃ or —CH₂CH₂CF₃;
R₂ is —CH₂CF₃, —CH₂CH₂CF₃, or —CH₂CH₂CH₂CF₃;
R₃ is H, —CH₃ or R$_x$;
R₄ is H or R$_y$;
R$_x$ is: —CH₂OC(O)CH(CH₃)NH₂, —CH₂OC(O)CH(NH₂)CH(CH₃)₂, —CH₂OC(O)CH((CH(CH₃)₂)NHC(O)CH(NH₂)CH(CH₃)₂,

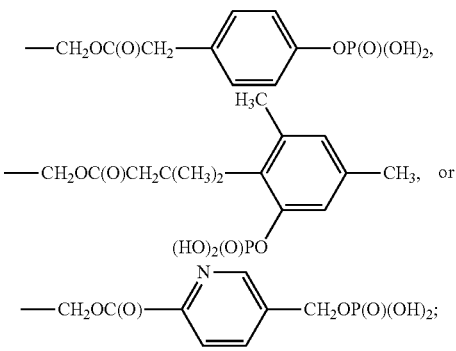

R$_y$ is: —SCH₂CH(NH₂)C(O)OH, —SCH₂CH(NH₂)C(O)OCH₃, or —SCH₂CH(NH₂)C(O)OC(CH₃)₃;
Ring A is phenyl or pyridinyl;
each R$_a$ is independently F, Cl, —CN, —OCH₃, C$_{1-3}$ alkyl, —CH₂OH, —CF₃, cyclopropyl, —OCH₃, —O(cyclopropyl) and/or —NHCH₂CH₂OCH₃;
each R$_b$ is independently F, Cl, —CH₃, —CH₂OH, —CF₃, cyclopropyl, and/or —OCH₃;
y is zero, 1 or 2; and
z is zero, 1, or 2.

In another embodiment, the present invention provides a method of treating cancer, wherein said cancer comprises one or more Notch-activating genetic alterations, comprising the step of administering to said subject a composition comprising one or more compounds represented by the structure of Formula (III):

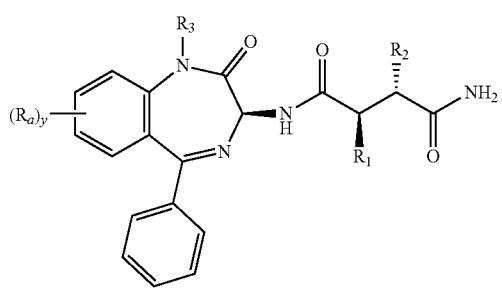

or prodrugs or salts thereof; wherein:
R₁ is —CH₂CF₃ or —CH₂CH₂CF₃;
R₂ is —CH₂CF₃, —CH₂CH₂CF₃, or —CH₂CH₂CH₂CF₃;
R₃ is H or —CH₃;
each R$_a$ is independently F, Cl, —CN, —OCH₃, and/or —NHCH₂CH₂OCH₃; and
y is zero, 1, or 2.

In another embodiment, the present invention provides a method of treating cancer, wherein said cancer comprises one or more Notch-activating genetic alterations, comprising the step of administering to said subject a composition comprising:

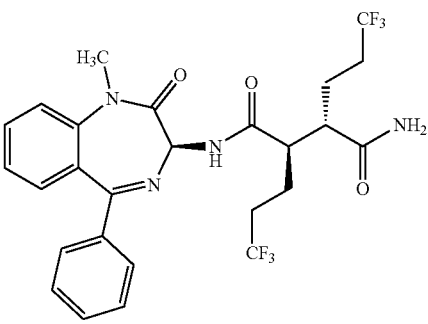 [SMILES: CN1C(=O)[C@@H](NC(=O)[C@H](CCC(F)(F)F)[C@H](CCC(F)(F)F)C(N)=O)N=C(c2ccccc2)c2ccccc21]

In another embodiment, the present invention provides a method of treating cancer, wherein said cancer comprises one or more Notch-activating genetic alterations, comprising the step of administering to said subject a composition comprising:

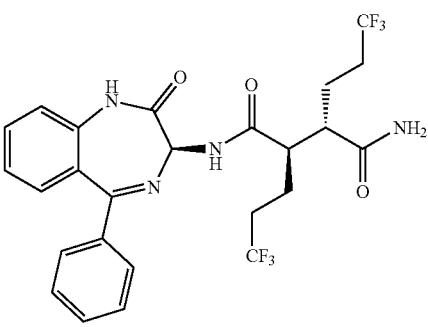 [SMILES: NC(=O)[C@@H](CCC(F)(F)F)[C@@H](CCC(F)(F)F)C(=O)N[C@H]1N=C(c2ccccc2)c2ccccc2NC1=O]

In one embodiment, the present invention provides a method of treating a carcinoma, wherein said carcinoma comprises one or more Notch-activating genetic alterations, comprising the step of administering to said subject a composition comprising one or more compounds represented by the structure of Formula (I) and/or at least one salt thereof,

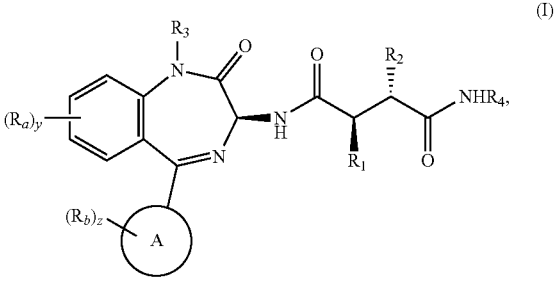

wherein:
R₁ is —CH₂CF₃ or —CH₂CH₂CF₃;
R₂ is —CH₂CF₃, —CH₂CH₂CF₃, or —CH₂CH₂CH₂CF₃;
R₃ is H, —CH₃ or R$_x$;
R₄ is H or R$_y$;
R$_x$ is: —CH₂OC(O)CH(CH₃)NH₂, —CH₂OC(O)CH(NH₂)CH(CH₃)₂, —CH₂OC(O)CH((CH(CH₃)₂)NHC(O)CH(NH₂)CH(CH₃)₂,

—CH₂OC(O)CH₂—[C₆H₄]—OP(O)(OH)₂,

—CH₂OC(O)CH₂C(CH₃)₂—[aryl with H₃C, CH₃, (HO)₂(O)PO],  or

—CH₂OC(O)—[pyridinyl]—CH₂OP(O)(OH)₂;

$R_y$ is: —SCH₂CH(NH₂)C(O)OH, —SCH₂CH(NH₂)C(O)OCH₃, or —SCH₂CH(NH₂)C(O)OC(CH₃)₃;

Ring A is phenyl or pyridinyl;

each $R_a$ is independently F, Cl, —CN, —OCH₃, $C_{1-3}$ alkyl, —CH₂OH, —CF₃, cyclopropyl, —OCH₃, —O(cyclopropyl) and/or —NHCH₂CH₂OCH₃;

each $R_b$ is independently F, Cl, —CH₃, —CH₂OH, —CF₃, cyclopropyl, and/or —OCH₃;

y is zero, 1 or 2; and z is zero, 1, or 2.

In another embodiment, the present invention provides a method of treating a carcinoma, wherein said carcinoma comprises one or more Notch-activating genetic alterations, comprising the step of administering to said subject a composition comprising one or more compounds represented by the structure of Formula (III):

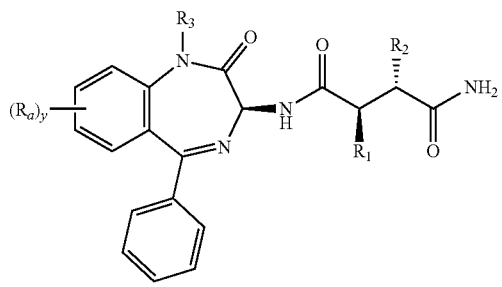

or prodrugs or salts thereof; wherein:

$R_1$ is —CH₂CF₃ or —CH₂CH₂CF₃;

$R_2$ is —CH₂CF₃, —CH₂CH₂CF₃, or —CH₂CH₂CH₂CF₃;

$R_3$ is H or —CH₃;

each $R_a$ is independently F, Cl, —CN, —OCH₃, and/or —NHCH₂CH₂OCH₃; and y is zero, 1, or 2.

In another embodiment, the present invention provides a method of treating a carcinoma, wherein said carcinoma comprises one or more Notch-activating genetic alterations, comprising the step of administering to said subject a composition comprising:

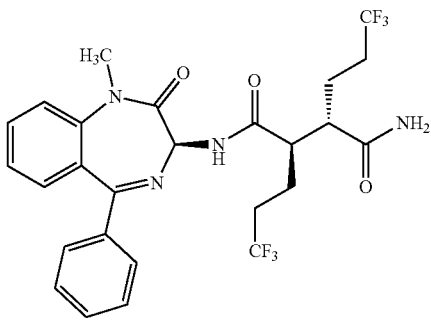 [SMILES: CN1C(=O)[C@@H](NC(=O)[C@H](CCC(F)(F)F)[C@H](CCC(F)(F)F)C(N)=O)N=C(c2ccccc2)c2ccccc21]

In another embodiment, the present invention provides a method of treating a carcinoma, wherein said carcinoma comprises one or more Notch-activating genetic alterations, comprising the step of administering to said subject a composition comprising:

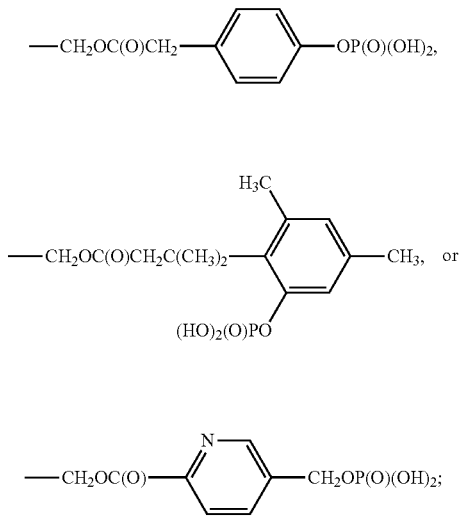

In one embodiment, the present invention provides a method of treating ACC, wherein said ACC comprises one or more Notch-activating genetic alterations, comprising the step of administering to said subject a composition comprising one or more compounds represented by the structure of Formula (I) and/or at least one salt thereof, (I)

wherein:

$R_1$ is —CH₂CF₃ or —CH₂CH₂CF₃;

$R_2$ is —CH₂CF₃, —CH₂CH₂CF₃, or —CH₂CH₂CH₂CF₃;

$R_3$ is H, —CH₃ or $R_x$;

$R_4$ is H or $R_y$;

$R_x$ is: —CH₂OC(O)CH(CH₃)NH₂, —CH₂OC(O)CH(NH₂)CH(CH₃)₂, —CH₂OC(O)CH((CH(CH₃)₂)NHC(O)CH(NH₂)CH(CH₃)₂,

—CH₂OC(O)CH₂—[C₆H₄]—OP(O)(OH)₂,

—CH₂OC(O)CH₂C(CH₃)₂—[aryl with H₃C, CH₃, (HO)₂(O)PO substituents]

—CH₂OC(O)—[pyridinyl]—CH₂OP(O)(OH)₂;

R_y is: —SCH₂CH(NH₂)C(O)OH, —SCH₂CH(NH₂)C(O)OCH₃, or —SCH₂CH(NH₂)C(O)OC(CH₃)₃;

Ring A is phenyl or pyridinyl;

each R_a is independently F, Cl, —CN, —OCH₃, C_{1-3} alkyl, —CH₂OH, —CF₃, cyclopropyl, —OCH₃, —O(cyclopropyl) and/or —NHCH₂CH₂OCH₃;

each R_b is independently F, Cl, —CH₃, —CH₂OH, —CF₃, cyclopropyl, and/or —OCH₃;

y is zero, 1 or 2; and z is zero, 1, or 2.

In another embodiment, the present invention provides a method of treating ACC, wherein said ACC comprises one or more Notch-activating genetic alterations, comprising the step of administering to said subject a composition comprising one or more compounds represented by the structure of Formula (III):

[Structure of Formula (III): benzodiazepine core with (R_a)_y substituent, R_3 on N, phenyl substituent, connected via NH to CH(R_1)-C(O)-CH(R_2)-C(O)NH₂]

or prodrugs or salts thereof; wherein:

R₁ is —CH₂CF₃ or —CH₂CH₂CF₃;

R₂ is —CH₂CF₃, —CH₂CH₂CF₃, or —CH₂CH₂CH₂CF₃;

R₃ is H or —CH₃;

each R_a is independently F, Cl, —CN, —OCH₃, and/or —NHCH₂CH₂OCH₃; and y is zero, 1, or 2.

In another embodiment, the present invention provides a method of treating ACC, wherein said ACC comprises one or more Notch-activating genetic alterations, comprising the step of administering to said subject a composition comprising:

[Structure: N-methyl benzodiazepine with phenyl, linked to CH(CH₂CH₂CF₃)-C(O)-CH(CH₂CH₂CF₃)-C(O)NH₂]

In another embodiment, the present invention provides a method of treating ACC, wherein said ACC comprises one or more Notch-activating genetic alterations, comprising the step of administering to said subject a composition comprising:

[Structure: NH benzodiazepine with phenyl, linked to CH(CH₂CH₂CF₃)-C(O)-CH(CH₂CH₂CF₃)-C(O)NH₂]

In one embodiment, the present invention provides a method of reducing tumor size in a subject having cancer, wherein said cancer comprises one or more Notch-activating genetic alterations, comprising the step of administering to said subject a composition comprising one or more compounds represented by the structure of Formula (I) and/or at least one salt thereof, as described herein.

In one embodiment, the present invention provides a method of reducing tumor size in a subject having a carcinoma, wherein said carcinoma comprises one or more Notch-activating genetic alterations, comprising the step of administering to said subject a composition comprising one or more compounds represented by the structure of Formula (I) and/or at least one salt thereof, as described herein.

In one embodiment, the present invention provides a method of reducing tumor size in a subject having ACC, wherein one or more cells of the ACC comprises one or more Notch-activating genetic alterations, comprising the step of administering to said subject a composition comprising one or more compounds represented by the structure of Formula (I) and/or at least one salt thereof,

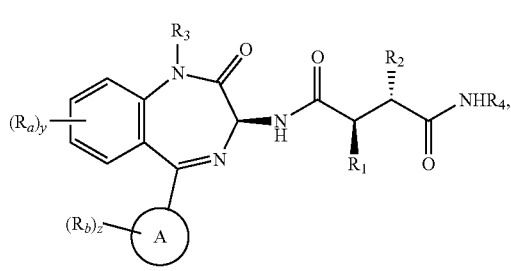

(I)

wherein:
R₁ is —CH₂CF₃ or —CH₂CH₂CF₃;
R₂ is —CH₂CF₃, —CH₂CH₂CF₃, or —CH₂CH₂CH₂CF₃;
R₃ is H, —CH₃ or R$_x$;
R₄ is H or R$_y$;
R$_x$ is: —CH₂OC(O)CH(CH₃)NH₂, —CH₂OC(O)CH(NH₂)CH(CH₃)₂, —CH₂OC(O)CH((CH(CH₃)₂)NHC(O)CH(NH₂)CH(CH₃)₂,

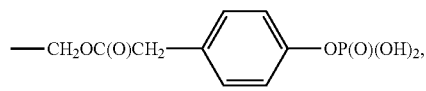

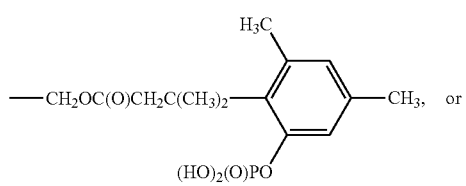

or

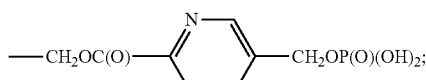

R$_y$ is: —SCH₂CH(NH₂)C(O)OH, —SCH₂CH(NH₂)C(O)OCH₃, or —SCH₂CH(NH₂)C(O)OC(CH₃)₃;
Ring A is phenyl or pyridinyl;
each R$_a$ is independently F, Cl, —CN, —OCH₃, C₁₋₃ alkyl, —CH₂OH, —CF₃, cyclopropyl, —OCH₃, —O(cyclopropyl) and/or —NHCH₂CH₂OCH₃;
each R$_b$ is independently F, Cl, —CH₃, —CH₂OH, —CF₃, cyclopropyl, and/or —OCH₃;
y is zero, 1 or 2; and
z is zero, 1, or 2.

In another embodiment, the present invention provides a method of reducing tumor size in a subject having ACC, wherein one or more cells of the ACC comprises one or more Notch-activating genetic alterations, comprising the step of administering to said subject a composition comprising one or more compounds represented by the structure of Formula (III):

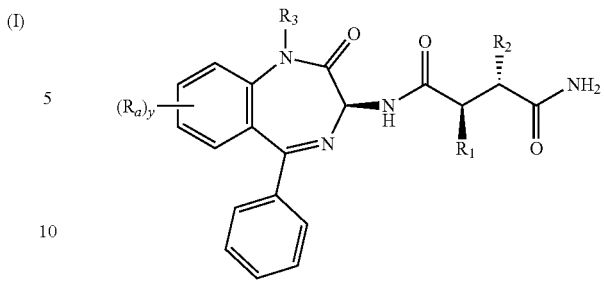

or prodrugs or salts thereof; wherein:
R₁ is —CH₂CF₃ or —CH₂CH₂CF₃;
R₂ is —CH₂CF₃, —CH₂CH₂CF₃, or —CH₂CH₂CH₂CF₃;
R₃ is H or —CH₃;
each R$_a$ is independently F, Cl, —CN, —OCH₃, and/or —NHCH₂CH₂OCH₃; and
y is zero, 1, or 2.

In another embodiment, the present invention provides a method of reducing tumor size in a subject having ACC, wherein one or more cells of said ACC comprises one or more Notch-activating genetic alterations, comprising the step of administering to said subject a composition comprising:

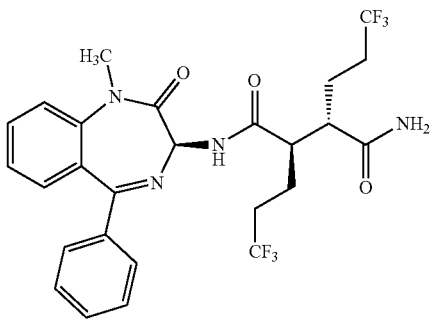 [SMILES: CN1C(=O)[C@@H](NC(=O)[C@H](CCC(F)(F)F)[C@H](CCC(F)(F)F)C(N)=O)N=C(c2ccccc2)c2ccccc21]

In another embodiment, the present invention provides a method of reducing tumor size in a subject having ACC, wherein one or more cells of said ACC comprises one or more Notch-activating genetic alterations, comprising the step of administering to said subject a composition comprising:

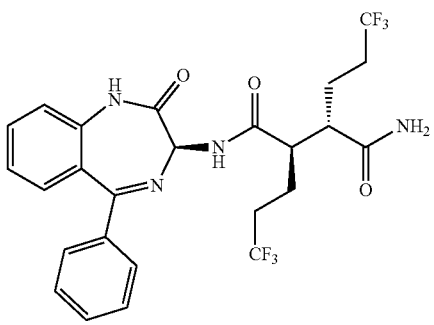 [SMILES: NC(=O)[C@@H](CCC(F)(F)F)[C@@H](CCC(F)(F)F)C(=O)N[C@H]1N=C(c2ccccc2)c2ccccc2NC1=O]

In one embodiment, reducing tumor size comprises decreasing tumor size by 25%-95%. In another embodiment, reducing tumor size comprises decreasing tumor size by 25%. In another embodiment, reducing tumor size comprises decreasing tumor size by 30%. In another embodiment, reducing tumor size comprises decreasing tumor size by 35%. In another embodiment, reducing tumor size comprises decreasing tumor size by 40%. In another embodiment, reducing tumor size comprises decreasing tumor size by 45%. In another embodiment, reducing tumor size comprises decreasing tumor size by 50%. In another embodiment, reducing tumor size comprises decreasing tumor size by 55%. In another embodiment, reducing tumor size comprises decreasing tumor size by 60%. In another embodiment, reducing tumor size comprises decreasing tumor size by 65%. In another embodiment, reducing tumor size comprises decreasing tumor size by 70%. In another embodiment, reducing tumor size comprises decreasing tumor size by 75%. In another embodiment, reducing tumor size comprises decreasing tumor size by 80%. In another embodiment, reducing tumor size comprises decreasing tumor size by 85%. In another embodiment, reducing tumor size comprises decreasing tumor size by 90%. In another embodiment, reducing tumor size comprises decreasing tumor size by 95%.

In one embodiment, the present invention provides a method of reducing tumor volume in a subject having cancer, wherein said cancer comprises one or more Notch-activating genetic alterations, comprising the step of administering to said subject a composition comprising one or more compounds represented by the structure of Formula (I) and/or at least one salt thereof, as described herein.

In one embodiment, the present invention provides a method of reducing tumor volume in a subject having a carcinoma, wherein said a carcinoma comprises one or more Notch-activating genetic alterations, comprising the step of administering to said subject a composition comprising one or more compounds represented by the structure of Formula (I) and/or at least one salt thereof, as described herein.

In one embodiment, the present invention provides a method of reducing tumor volume in a subject having ACC, wherein one or more cells of the ACC comprises one or more Notch-activating genetic alterations, comprising the step of administering to said subject a composition comprising one or more compounds represented by the structure of Formula (I) and/or at least one salt thereof,

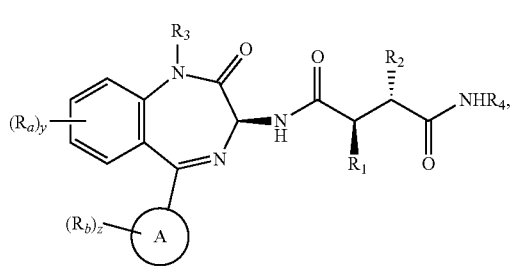

(I)

wherein:
$R_1$ is —CH$_2$CF$_3$ or —CH$_2$CH$_2$CF$_3$;
$R_2$ is —CH$_2$CF$_3$, —CH$_2$CH$_2$CF$_3$, or —CH$_2$CH$_2$CH$_2$CF$_3$;
$R_3$ is H, —CH$_3$ or $R_x$;
$R_4$ is H or $R_y$;
$R_x$ is: —CH$_2$OC(O)CH(CH$_3$)NH$_2$, —CH$_2$OC(O)CH(NH$_2$)CH(CH$_3$)$_2$, —CH$_2$OC(O)CH((CH$_3$)$_2$)NHC(O)CH(NH$_2$)CH(CH$_3$)$_2$,

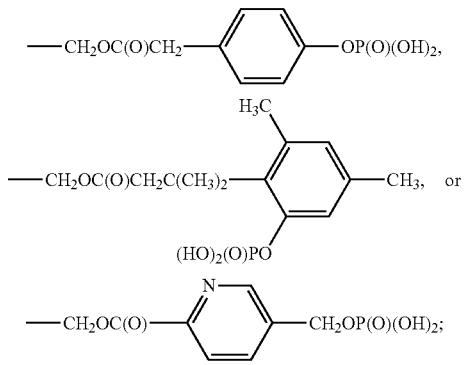

$R_y$ is: —SCH$_2$CH(NH$_2$)C(O)OH, —SCH$_2$CH(NH$_2$)C(O)OCH$_3$, or —SCH$_2$CH(NH$_2$)C(O)OC(CH$_3$)$_3$;
Ring A is phenyl or pyridinyl;
each $R_a$ is independently F, Cl, —CN, —OCH$_3$, C$_{1-3}$ alkyl, —CH$_2$OH, —CF$_3$, cyclopropyl, —OCH$_3$, —O(cyclopropyl) and/or —NHCH$_2$CH$_2$OCH$_3$;
each $R_b$ is independently F, Cl, —CH$_3$, —CH$_2$OH, —CF$_3$, cyclopropyl, and/or —OCH$_3$;
y is zero, 1 or 2; and
z is zero, 1, or 2.

In another embodiment, the present invention provides a method of reducing tumor volume in a subject having ACC, wherein one or more cells of the ACC comprises one or more Notch-activating genetic alterations, comprising the step of administering to said subject a composition comprising one or more compounds represented by the structure of Formula (III):

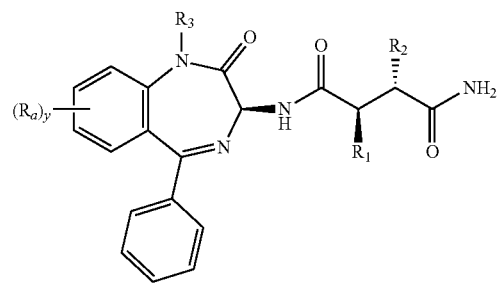

or prodrugs or salts thereof; wherein:
$R_1$ is —CH$_2$CF$_3$ or —CH$_2$CH$_2$CF$_3$;
$R_2$ is —CH$_2$CF$_3$, —CH$_2$CH$_2$CF$_3$, or —CH$_2$CH$_2$CH$_2$CF$_3$;
$R_3$ is H or —CH$_3$;
each $R_a$ is independently F, Cl, —CN, —OCH$_3$, and/or —NHCH$_2$CH$_2$OCH$_3$; and
y is zero, 1, or 2.

In another embodiment, the present invention provides a method of reducing tumor volume in a subject having ACC, wherein one or more cells of said ACC comprises one or more Notch-activating genetic alterations, comprising the step of administering to said subject a composition comprising:

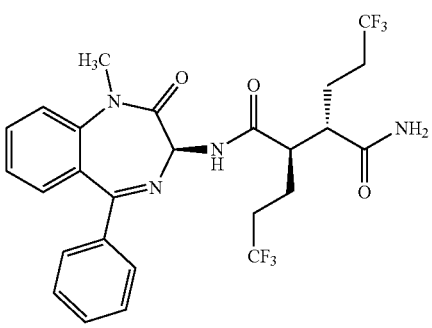 [SMILES: CN1C(=O)[C@@H](NC(=O)[C@H](CCC(F)(F)F)[C@H](CCC(F)(F)F)C(N)=O)N=C(c2ccccc2)c2ccccc21]

In another embodiment, the present invention provides a method of reducing tumor volume in a subject having ACC, wherein one or more cells of said ACC comprises one or more Notch-activating genetic alterations, comprising the step of administering to said subject a composition comprising:

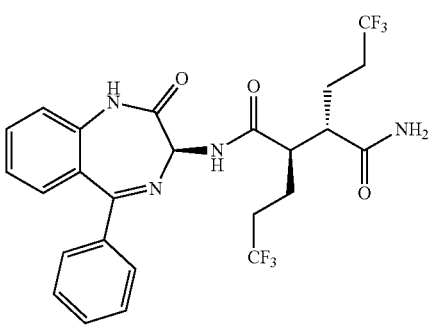 [SMILES: NC(=O)[C@@H](CCC(F)(F)F)[C@@H](CCC(F)(F)F)C(=O)N[C@H]1N=C(c2ccccc2)c2ccccc2NC1=O]

In one embodiment, reducing tumor volume comprises decreasing tumor volume by 25%-95%. In another embodiment, reducing tumor volume comprises decreasing tumor volume by 25%. In another embodiment, reducing tumor volume comprises decreasing tumor volume by 30%. In another embodiment, reducing tumor volume comprises decreasing tumor volume by 35%. In another embodiment, reducing tumor volume comprises decreasing tumor volume by 40%. In another embodiment, reducing tumor volume comprises decreasing tumor volume by 45%. In another embodiment, reducing tumor volume comprises decreasing tumor volume by 50%. In another embodiment, reducing tumor volume comprises decreasing tumor volume by 55%. In another embodiment, reducing tumor volume comprises decreasing tumor volume by 60%. In another embodiment, reducing tumor volume comprises decreasing tumor volume by 65%. In another embodiment, reducing tumor volume comprises decreasing tumor volume by 70%. In another embodiment, reducing tumor volume comprises decreasing tumor volume by 75%. In another embodiment, reducing tumor volume comprises decreasing tumor volume by 80%. In another embodiment, reducing tumor volume comprises decreasing tumor volume by 85%. In another embodiment, reducing tumor volume comprises decreasing tumor volume by 90%. In another embodiment, reducing tumor volume comprises decreasing tumor volume by 95%.

In one embodiment, the present invention provides a method of suppressing tumor growth in a subject having a tumor, wherein one or more cells of said tumor comprises one or more Notch-activating genetic alterations, comprising the step of administering to said subject a composition comprising one or more compounds represented by the structure of Formula (I) and/or at least one salt thereof, as described herein.

In one embodiment, the present invention provides a method of suppressing tumor growth in a subject having a carcinoma, wherein one or more cells of said carcinoma comprises one or more Notch-activating genetic alterations, comprising the step of administering to said subject a composition comprising one or more compounds represented by the structure of Formula (I) and/or at least one salt thereof, as described herein.

In one embodiment, the present invention provides a method of suppressing tumor growth in a subject having ACC, wherein one or more cells of said ACC comprises one or more Notch-activating genetic alterations, comprising the step of administering to said subject a composition comprising one or more compounds represented by the structure of Formula (I) and/or at least one salt thereof, as described herein.

In another embodiment, the present invention provides a method of suppressing tumor growth in a subject having ACC, wherein one or more cells of the ACC comprises one or more Notch-activating genetic alterations, comprising the step of administering to said subject a composition comprising one or more compounds represented by the structure of Formula (III):

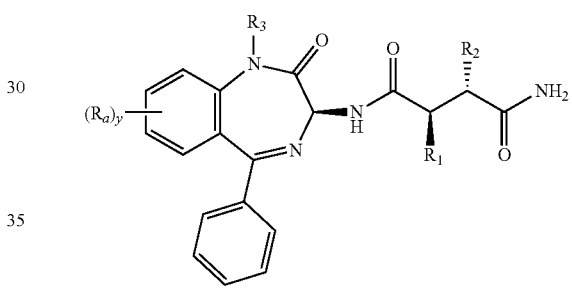

or prodrugs or salts thereof; wherein:
$R_1$ is —$CH_2CF_3$ or —$CH_2CH_2CF_3$;
$R_2$ is —$CH_2CF_3$, —$CH_2CH_2CF_3$, or —$CH_2CH_2CH_2CF_3$;
$R_3$ is H or —$CH_3$;
each $R_a$ is independently F, Cl, —CN, —$OCH_3$, and/or —$NHCH_2CH_2OCH_3$; and
y is zero, 1, or 2.

In another embodiment, the present invention provides a method of suppressing tumor growth in a subject having ACC, wherein one or more cells of the ACC comprises one or more Notch-activating genetic alterations, comprising the step of administering to said subject a composition comprising:

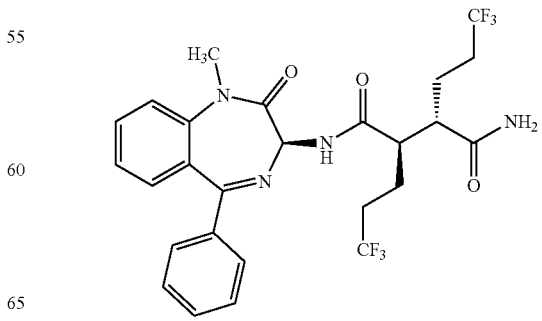

In another embodiment, the present invention provides a method of suppressing tumor growth in a subject having ACC, wherein one or more cells of the ACC comprises one or more Notch-activating genetic alterations, comprising the step of administering to said subject a composition comprising:

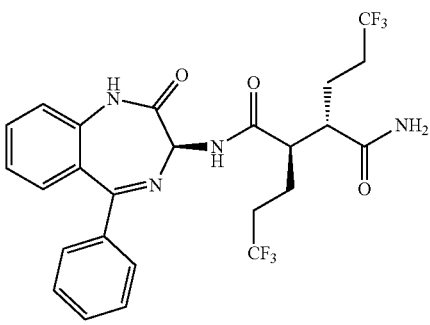 [SMILES: NC(=O)[C@@H](CCC(F)(F)F)[C@@H](CCC(F)(F)F)C(=O)N[C@H]1N=C(c2ccccc2)c2ccccc2NC1=O]

In one embodiment, administration of a composition as described herein suppresses tumor growth by 20-99% compared to untreated tumors, or compared to tumors treated with another anti-cancer therapy. In another embodiment, tumor growth is suppressed by 20-35%. In another embodiment, tumor growth is suppressed by 35-50%. In another embodiment, tumor growth is suppressed by 50-75%. In another embodiment, tumor growth is suppressed by 75-90%. In another embodiment, tumor growth is suppressed by 90-99%.

In another embodiment, tumor growth is suppressed by 20%. In another embodiment, tumor growth is suppressed by 25%. In another embodiment, tumor growth is suppressed by 30%. In another embodiment, tumor growth is suppressed by 35%. In another embodiment, tumor growth is suppressed by 40%. In another embodiment, tumor growth is suppressed by 45%. In another embodiment, tumor growth is suppressed by 50%. In another embodiment, tumor growth is suppressed by 55%. In another embodiment, tumor growth is suppressed by 60%. In another embodiment, tumor growth is suppressed by 65%. In another embodiment, tumor growth is suppressed by 70%. In another embodiment, tumor growth is suppressed by 75%. In another embodiment, tumor growth is suppressed by 80%. In another embodiment, tumor growth is suppressed by 85%. In another embodiment, tumor growth is suppressed by 90%. In another embodiment, tumor growth is suppressed by 95%. In another embodiment, tumor growth is suppressed by 99%.

In one embodiment, the present invention provides a method of inhibiting tumor growth in a subject having a tumor, wherein one or more cells of said tumor comprises one or more Notch-activating genetic alterations, comprising the step of administering to said subject a composition comprising one or more compounds represented by the structure of Formula (I) and/or at least one salt thereof, as described herein.

In one embodiment, the present invention provides a method of inhibiting tumor growth in a subject having a carcinoma, wherein one or more cells of said carcinoma comprises one or more Notch-activating genetic alterations, comprising the step of administering to said subject a composition comprising one or more compounds represented by the structure of Formula (I) and/or at least one salt thereof, as described herein.

In one embodiment, the present invention provides a method of inhibiting tumor growth in a subject having ACC, wherein one or more cells of the ACC comprises one or more Notch-activating genetic alterations, comprising the step of administering to said subject a composition comprising one or more compounds represented by the structure of Formula (I) and/or at least one salt thereof, as described herein.

In one embodiment, the present invention provides a method of inhibiting tumor growth in a subject having ACC, wherein one or more cells of the ACC comprises one or more Notch-activating genetic alterations, comprising the step of administering to said subject a composition comprising one or more compounds represented by the structure of Formula (III):

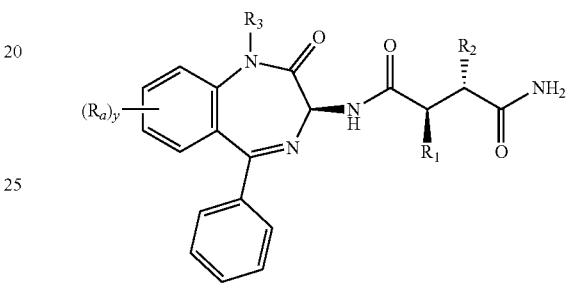

or prodrugs or salts thereof; wherein:

$R_1$ is —$CH_2CF_3$ or —$CH_2CH_2CF_3$;

$R_2$ is —$CH_2CF_3$, —$CH_2CH_2CF_3$, or —$CH_2CH_2CH_2CF_3$;

$R_3$ is H or —$CH_3$;

each $R_a$ is independently F, Cl, —CN, —$OCH_3$, and/or —$NHCH_2CH_2OCH_3$; and y is zero, 1, or 2.

In one embodiment, the present invention provides a method of inhibiting tumor growth in a subject having ACC, wherein one or more cells of the ACC comprises one or more Notch-activating genetic alterations, comprising the step of administering to said subject a composition comprising:

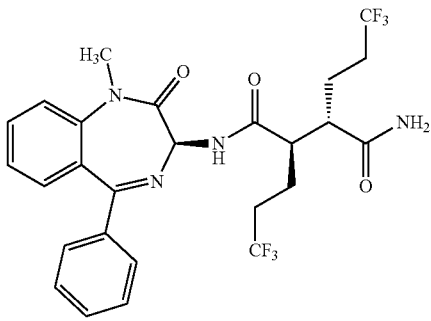 [SMILES: CN1C(=O)[C@@H](NC(=O)[C@H](CCC(F)(F)F)[C@H](CCC(F)(F)F)C(N)=O)N=C(c2ccccc2)c2ccccc21]

In one embodiment, the present invention provides a method of inhibiting tumor growth in a subject having ACC, wherein one or more cells of the ACC comprises one or more Notch-activating genetic alterations, comprising the step of administering to said subject a composition comprising:

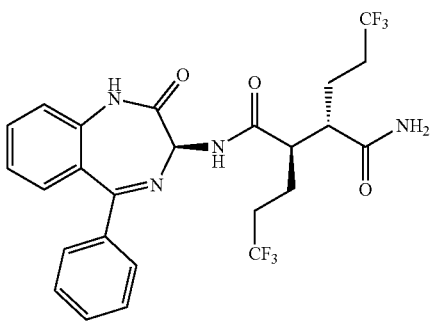 [SMILES: NC(=O)[C@@H](CCC(F)(F)F)[C@@H](CCC(F)(F)F)C(=O)N[C@H]1N=C(c2ccccc2)c2ccccc2NC1=O]

In one embodiment, inhibiting tumor growth comprises decreasing the growth of the tumor in comparison to control by 100%.

In one embodiment, the present invention provides a method of prolonging progression-free survival or overall survival in a subject having a tumor, wherein one or more cells of said tumor comprises one or more Notch-activating genetic alterations, comprising the step of administering to said subject a composition comprising one or more compounds represented by the structure of Formula (I) and/or at least one salt thereof, as described herein.

In one embodiment, the present invention provides a method of prolonging progression-free survival or overall survival in a subject having a carcinoma, wherein one or more cells of said carcinoma comprises one or more Notch-activating genetic alterations, comprising the step of administering to said subject a composition comprising one or more compounds represented by the structure of Formula (I) and/or at least one salt thereof, as described herein.

In one embodiment, the present invention provides a method of prolonging progression-free survival or overall survival in a subject having ACC, wherein one or more cells of the ACC comprises one or more Notch-activating genetic alterations, comprising the step of administering to said subject a composition comprising one or more compounds represented by the structure of Formula (I) and/or at least one salt thereof,

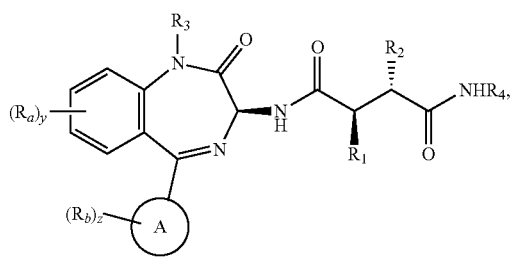

(I)

wherein:
$R_1$ is —CH$_2$CF$_3$ or —CH$_2$CH$_2$CF$_3$;
$R_2$ is —CH$_2$CF$_3$, —CH$_2$CH$_2$CF$_3$, or —CH$_2$CH$_2$CH$_2$CF$_3$;
$R_3$ is H, —CH$_3$ or $R_x$;
$R_4$ is H or $R_y$;
$R_x$ is: —CH$_2$OC(O)CH(CH$_3$)NH$_2$, —CH$_2$OC(O)CH(NH$_2$)CH(CH$_3$)$_2$, —CH$_2$OC(O)CH((CH$_3$)$_2$)NHC(O)CH(NH$_2$)CH(CH$_3$)$_2$,

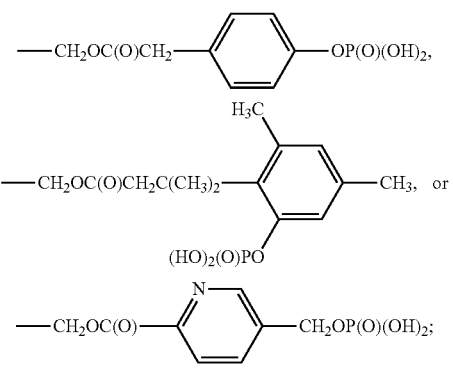

$R_y$ is: —SCH$_2$CH(NH$_2$)C(O)OH, —SCH$_2$CH(NH$_2$)C(O)OCH$_3$, or —SCH$_2$CH(NH$_2$)C(O)OC(CH$_3$)$_3$;
Ring A is phenyl or pyridinyl;
each $R_a$ is independently F, Cl, —CN, —OCH$_3$, C$_{1-3}$ alkyl, —CH$_2$OH, —CF$_3$, cyclopropyl, —OCH$_3$, —O(cyclopropyl) and/or —NHCH$_2$CH$_2$OCH$_3$;
each $R_b$ is independently F, Cl, —CH$_3$, —CH$_2$OH, —CF$_3$, cyclopropyl, and/or —OCH$_3$;
y is zero, 1 or 2; and
z is zero, 1, or 2.

In one embodiment, the present invention provides a method of prolonging progression-free survival or overall survival in a subject having ACC, wherein one or more cells of the ACC comprises one or more Notch-activating genetic alterations, comprising the step of administering to said subject a composition comprising one or more compounds represented by the structure of Formula (III):

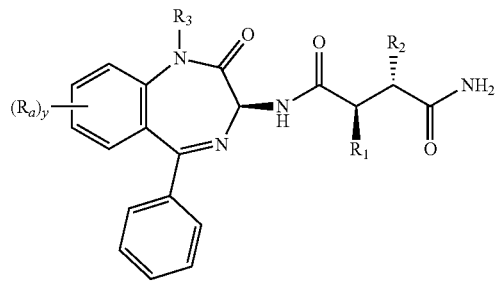

or prodrugs or salts thereof; wherein:
$R_1$ is —CH$_2$CF$_3$ or —CH$_2$CH$_2$CF$_3$;
$R_2$ is —CH$_2$CF$_3$, —CH$_2$CH$_2$CF$_3$, or —CH$_2$CH$_2$CH$_2$CF$_3$;
$R_3$ is H or —CH$_3$;
each $R_a$ is independently F, Cl, —CN, —OCH$_3$, and/or —NHCH$_2$CH$_2$OCH$_3$; and
y is zero, 1, or 2.

In one embodiment, the present invention provides a method of prolonging progression-free survival or overall survival in a subject having ACC, wherein one or more cells of the ACC comprises one or more Notch-activating genetic alterations, comprising the step of administering to said subject a composition comprising:

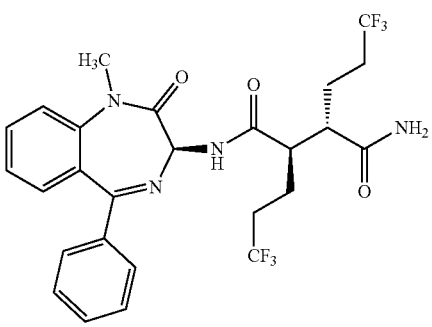 [SMILES: CN1C(=O)[C@@H](NC(=O)[C@H](CCC(F)(F)F)[C@H](CCC(F)(F)F)C(N)=O)N=C(c2ccccc2)c2ccccc21]

In one embodiment, the present invention provides a method of prolonging progression-free survival or overall survival in a subject having ACC, wherein one or more cells of the ACC comprises one or more Notch-activating genetic alterations, comprising the step of administering to said subject a composition comprising:

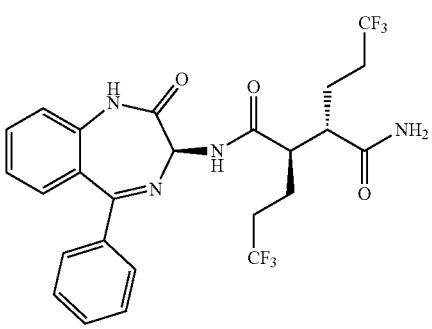 [SMILES: NC(=O)[C@@H](CCC(F)(F)F)[C@@H](CCC(F)(F)F)C(=O)N[C@H]1N=C(c2ccccc2)c2ccccc2NC1=O]

In one embodiment, the present invention provides a method of reducing tumor size or suppressing or inhibiting tumor growth in a subject having cancer, wherein said cancer lacks a Notch GOF mutation, comprising the steps of administering to said subject a first composition comprising one or more compounds represented by the structure of Formula (I) and/or at least one salt thereof, as described herein and a second composition comprising an additional anti-cancer agent.

In one embodiment, the present invention provides a method of reducing tumor size or suppressing or inhibiting tumor growth in a subject having a carcinoma, wherein said a carcinoma lacks a Notch GOF mutation, comprising the steps of administering to said subject a first composition comprising one or more compounds represented by the structure of Formula (I) and/or at least one salt thereof, as described herein and a second composition comprising an additional anti-cancer agent.

In one embodiment, the present invention provides a method of reducing tumor size or suppressing or inhibiting tumor growth in a subject having ACC, wherein one or more cells of the ACC lacks a Notch GOF mutation, comprising the steps of administering to said subject a first composition comprising one or more compounds represented by the structure of Formula (I) and/or at least one salt thereof as described herein and a second composition comprising an additional anti-cancer agent.

In another embodiment, the present invention provides a method of reducing tumor size or suppressing or inhibiting tumor growth in a subject having ACC, wherein one or more cells of the ACC lacks a Notch GOF mutation, comprising the steps of administering to said subject a first composition comprising one or more compounds represented by the structure of Formula (III) as described herein and a second composition comprising an additional anti-cancer agent.

In another embodiment, the present invention provides a method of reducing tumor size or suppressing or inhibiting tumor growth in a subject having ACC, wherein one or more cells of said ACC lacks a Notch GOF mutation, comprising the steps of administering to said subject a first composition comprising:

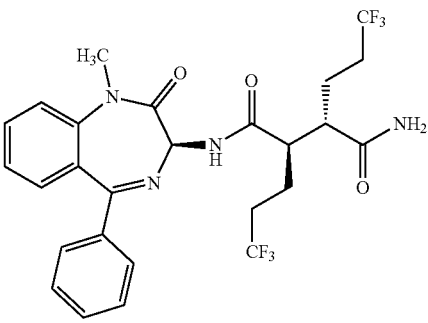 [SMILES: CN1C(=O)[C@@H](NC(=O)[C@H](CCC(F)(F)F)[C@H](CCC(F)(F)F)C(N)=O)N=C(c2ccccc2)c2ccccc21]

and a second composition comprising an additional anti-cancer agent.

In another embodiment, the present invention provides a method of reducing tumor size or suppressing or inhibiting tumor growth in a subject having ACC, wherein one or more cells of said ACC lacks a Notch GOF mutation, comprising the step of administering to said subject a first composition comprising:

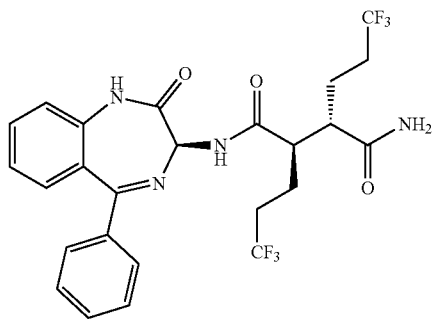 [SMILES: NC(=O)[C@@H](CCC(F)(F)F)[C@@H](CCC(F)(F)F)C(=O)N[C@H]1N=C(c2ccccc2)c2ccccc2NC1=O]

and a second composition comprising an additional anti-cancer agent.

In one embodiment, the anti-cancer agent comprises eribulin. In another embodiment, the anti-cancer agent comprises vinorelbine. In one embodiment, the combined therapy is administered to a subject wherein said Notch-activating genetic alteration does not comprise a Notch GOF mutation.

In another embodiment, the cancer comprises astrocytoma, bladder cancer, breast cancer, cholangiocarcinoma (CCA), colon cancer, colorectal cancer, colorectal carcinoma, epithelial carcinoma, epithelial ovarian cancers, fibrosarcoma, gall bladder cancer, gastric cancer, glioblastoma, glioma, head and neck cancer, hepatocellular carcinoma, kidney cancer, liver cancer, lung cancer including non-small cell lung cancer (NSCLC), malignant fibrous histiocytoma (MFH), malignant pleural mesothelioma (MPM), medulloblastoma, melanoma, mesothelioma, neuroblastoma, osteosarcoma, ovarian adenocarcinoma, ovarian cancer, pancreatic adenocarcinoma, pancreatic cancer, prostate cancer, renal cell carcinoma (RCC), rhabdomyosarcoma, seminal vesicle cancer, endometrial cancer, and thyroid cancer.

As used herein, the term "cancer" includes the above categories of carcinoma, sarcoma, myeloma, leukemia, lymphoma and mixed type tumors. In particular, the term cancer includes: lymphoproliferative disorders, breast cancer, ovarian cancer, prostate cancer, cervical cancer, endometrial cancer, lung cancer, bone cancer, liver cancer, stomach cancer, bladder cancer, colon cancer, colorectal cancer, pancreatic cancer, cancer of the thyroid, head and neck cancer, cancer of the central nervous system, brain cancer, cancer of the peripheral nervous system, skin cancer, kidney cancer, as well as metastases of all the above. More particularly, as used herein the term may refer to: hepatocellular carcinoma, hematoma, hepatoblastoma, rhabdomyosarcoma, esophageal carcinoma, thyroid carcinoma, ganglioblastoma, glioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma, Waldenstrom's Macroglobulinemia, or a combination thereof. In another embodiment, cancer comprises squamous cell carcinoma.

In another embodiment, the administration of the any of the compositions as described herein reduces growth of the cells of a solid tumor or hematological malignancy by 40%, 50%, 60%, 70%, 80%, 90% or 95% compared to growth of the cells of the solid tumor or hematological malignancy that have not been treated with the compositions. In the case of combination treatments, the administration of any of the described combinations reduces growth of the cells of a solid tumor or hematological malignancy compared to subjects treated with either one of the compositions, via a different cancer treatment, or who have not been treated.

In another embodiment, the present invention provides methods of increasing or lengthening survival of a subject having a neoplasia. As used herein, the term "neoplasia" refers to a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasias can affect a variety of cell types, tissues, or organs, including but not limited to an organ selected from the group consisting of bladder, colon, bone, brain, breast, cartilage, glia, esophagus, fallopian tube, gallbladder, heart, intestines, kidney, liver, lung, lymph node, nervous tissue, ovaries, pleura, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasias include cancers, such as sarcomas, carcinomas, or plasmacytomas (malignant tumor of the plasma cells).

In one embodiment, a subject as described herein is being treated with or has been previously treated with radiation therapy, chemotherapy, transplantation, immunotherapy, hormone therapy, or photodynamic therapy.

In another embodiment, the present invention provides a method of treating or suppressing an Adenoid Cystic Carcinoma (ACC) tumor in a subject comprising the step of administering to said subject a composition comprising one or more compounds represented by the structure of Formula (I) and/or at least one salt thereof, as described herein.

In another embodiment, the present invention provides a method of treating or suppressing an Adenoid Cystic Carcinoma (ACC) tumor in a subject comprising the step of administering to said subject a composition comprising one or more compounds represented by the structure of Formula (III):

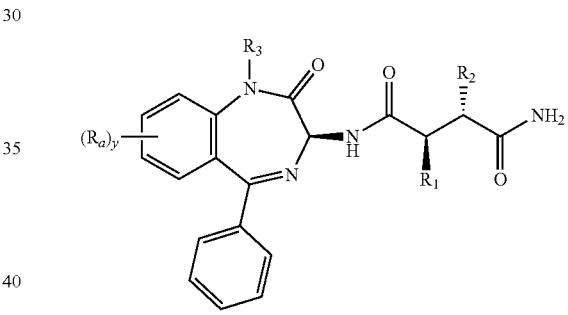

or prodrugs or salts thereof; wherein:
$R_1$ is —$CH_2CF_3$ or —$CH_2CH_2CF_3$;
$R_2$ is —$CH_2CF_3$, —$CH_2CH_2CF_3$, or —$CH_2CH_2CH_2CF_3$;
$R_3$ is H or —$CH_3$;
each $R_a$ is independently F, Cl, —CN, —$OCH_3$, and/or —$NHCH_2CH_2OCH_3$; and
y is zero, 1, or 2.

In another embodiment, the present invention also provides a method of inhibiting tumor growth in a subject with an Adenoid Cystic Carcinoma (ACC) tumor comprising the step of administering to said subject a composition comprising one or more compounds represented by the structure of Formula (I), and/or at least one salt thereof, as described herein.

In another embodiment, the present invention also provides a method of inhibiting tumor growth in a subject with an Adenoid Cystic Carcinoma (ACC) tumor comprising the step of administering to said subject a composition comprising one or more compounds represented by the structure of Formula (III):

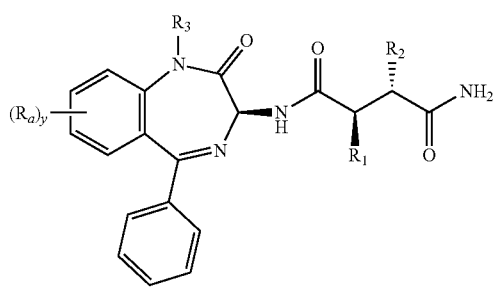

or prodrugs or salts thereof; wherein:
$R_1$ is —$CH_2CF_3$ or —$CH_2CH_2CF_3$;
$R_2$ is —$CH_2CF_3$, —$CH_2CH_2CF_3$, or —$CH_2CH_2CH_2CF_3$;
$R_3$ is H or —$CH_3$;
each $R_a$ is independently F, Cl, —CN, —$OCH_3$, and/or —$NHCH_2CH_2OCH_3$; and
y is zero, 1, or 2.

In one embodiment, the ACC tumor comprises tubular ACC, cribriform ACC, or solid ACC.

Notch-Activating Genetic Alterations

In one embodiment, a cancer as described herein comprises a Notch activating alteration. In another embodiment, a cancer as described herein comprises a Notch activating genetic alteration. In another embodiment, a cancer as described herein comprises a Notch activating mutation. In another embodiment, a cancer as described herein comprises a Notch activating genetic mutation. In another embodiment, a cancer as described herein comprises a Notch mutation. In another embodiment, a cancer as described herein comprises a Notch altering mutation.

In one embodiment, a Notch-activating genetic alteration comprises a mutation in a gene that activates the Notch signaling pathway.

In one embodiment, a Notch-activating genetic alteration comprises a sequence variant of one or more Notch-related genes. In another embodiment, a Notch-activating genetic alteration comprises a mutation in one or more Notch-related genes.

In one embodiment, the mutation in one or more Notch-related genes induces a gain of function (GOF) in Notch activity. In one embodiment, a subject whose cancer cells comprise one or more mutations leading to Notch GOF are administered monotherapy with a compound of Formula (I) as described herein. In another embodiment, a subject whose cancer cells comprise one or more mutations leading to Notch GOF are administered a combination therapy comprising a compound of Formula (I) as described herein and another anti-cancer compound.

In another embodiment, the mutation in one or more Notch-related genes induces a loss of function (LOF) in Notch activity. In one embodiment, a subject whose cancer cells comprise one or more mutations leading to Notch LOF are administered a combination therapy comprising a compound of Formula (I) as described herein and another anti-cancer therapy. In one embodiment, the anti-cancer therapy comprises a chemotherapy.

In another embodiment, it is not known if the mutation is a GOF or LOF Notch mutation. In one embodiment, the mutation comprises a variant of unknown significance (VUS).

In one embodiment, the mutation in one or more Notch-related genes comprises a negative regulatory region (NRR) mutation. In another embodiment, the mutation in one or more Notch-related genes comprises a proline, glutamic acid, serine and threonine rich domain (PEST) mutation. In another embodiment, the mutation in one or more Notch-related genes comprises NRR and PEST mutations.

In one embodiment, the Notch-activating mutation functionally inactivates the PEST domain of the Notch gene. In another embodiment, the Notch-activating mutation functionally inactivates the negative regulatory region (NRR) of the Notch gene.

In one embodiment, the Notch-activating mutation comprises a sequence variant in the NRR domain of a Notch gene. In another embodiment, the Notch-activating mutation comprises a sequence variant in the PEST domain of a Notch gene. In another embodiment, the Notch-activating mutation comprises a sequence variant in both the NRR domain and the PEST domain of one or more Notch genes. In another embodiment, the Notch-activating mutation comprises a gene rearrangement in the ectodomain of a Notch gene. In another embodiment, the gene rearrangement removes most of the ectodomain.

In another embodiment, the gene rearrangement functionally inactivates most of the NRR. In one embodiment, the gene rearrangement removes some of the NRR. In another embodiment, the gene rearrangement removes most of the NRR.

In one embodiment, the Notch-activating mutation is a gain-of-function (GOF) mutation in one or more Notch genes. In one embodiment, such GOF mutations may be associated with the Notch extracellular negative regulatory region (NRR), the Notch intracellular C-terminal PEST degron domain, or both. In one embodiment, the NRR maintains the receptor in the off state in the absence of ligand. In one embodiment, the C-terminal PEST degron domain promotes the rapid turnover of activated Notch receptors.

In one embodiment, a GOF NRR mutation comprises one or more point mutations, one or more in-frame insertions or deletions (indels), one or more gene rearrangements, or a combination thereof. In one embodiment, the mutation perturbs the structure of the NRR. In another embodiment, the mutation removes the coding sequence of the NRR. In one embodiment, the NRR mutation promotes ligand-independent Notch cleavage by ADAMs and/or gamma-secretase, and in one embodiment, generates high levels of NICD. In one embodiment the NRR mutation is in Notch1. In another embodiment, the NRR mutation is in Notch3.

In another embodiment, the GOF mutation may be associated with PEST domain mutations, which, in one embodiment, comprise nonsense mutations, out-of-frame indels, large deletions that remove the PEST domain and sustain the activity of Notch1 Intracellular Domain (NICD1), or a combination thereof.

In one embodiment, the presence of PEST mutations in cis with NRR mutations synergistically increases Notch activation. In one embodiment, the NRR and PEST domain mutations are in a single Notch allele. In another embodiment, the NRR and PEST domain mutations are in different Notch alleles.

In another embodiment, Notch GOF mutations are associated with one or more truncated forms of any one of the four Notch genes. In one embodiment, such truncations comprise rearrangements which, in one embodiment, remove the sequences encoding the ectodomain of the receptor. In one embodiment, these rearrangements produce Notch genes that drive the transcription of aberrant 5'-deleted transcripts encoding constitutively active polypeptides that lack the EGF-like ligand binding domain and/or NRR regions.

In one embodiment the Notch-activating mutation is an NRR mutation described in Weng A P, et al., Science. 2004; 306(5694):269-271 or Stoeck A, et al. Cancer Discov. 2014; 4(10):1154-1167, each of which is herein incorporated by reference in its entirety.

In one embodiment, a mutation in one or more Notch-related genes comprises a mutation in a Notch gene hotspot. In one embodiment, a Notch gene hotspot comprises an NRR domain, a PEST domain, or a combination thereof. In one embodiment, a mutation in one or more Notch-related genes comprises a mutation in an NRR. In another embodiment, a mutation in one or more Notch-related genes comprises a mutation in a PEST domain. In another embodiment, a mutation in one or more Notch-related genes comprises a mutation in an NRR and a PEST domain. In one embodiment, these mutations are GOF mutations.

In another embodiment, the mutation in one or more Notch-related genes comprises a gene rearrangement that removes most of the Notch ectodomain, including the NRR. In one embodiment, these mutations are GOF mutations.

In another embodiment, the Notch-activating genetic alteration comprises a missense mutation. In another embodiment, the Notch-activating genetic alteration comprises a nonsense mutation. In another embodiment, the Notch-activating genetic alteration comprises an insertion. In another embodiment, the Notch-activating genetic alteration comprises a deletion. In another embodiment, the Notch-activating genetic alteration comprises a duplication. In another embodiment, the Notch-activating genetic alteration comprises a frameshift mutation. In another embodiment, the Notch-activating genetic alteration comprises a repeat expansion. In another embodiment, Notch-activating genetic alteration comprises a gene fusion.

In one embodiment, the Notch-related gene comprises a Notch1-related gene. In another embodiment, the Notch-related gene comprises a Notch2-related gene. In another embodiment, the Notch-related gene comprises a Notch3-related gene. In another embodiment, the Notch-related gene comprises a Notch4-related gene.

In another embodiment, the Notch-related gene comprises Notch1. In another embodiment, the Notch-related gene comprises Notch2. In another embodiment, the Notch-related gene comprises Notch3. In another embodiment, the Notch-related gene comprises Notch4.

In one embodiment, the Notch-activating mutation comprises a Notch 1 mutation, a Notch 2 mutation, a Notch 3 mutation, a Notch 4 mutation, or a combination thereof.

Definitions

Unless specifically stated otherwise herein, references made in the singular may also include the plural. For example, "a" and "an" may refer to either one, or one or more.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

As used herein, the term "administering" refers to bringing in contact with a compound of the present invention. In one embodiment, the compositions are applied locally. In another embodiment, the compositions are applied systemically. Administration can be accomplished to cells or tissue cultures, or to living organisms, for example humans.

As used herein, the terms "administering," "administer," or "administration" refer to deliver one or more compounds or compositions to a subject parenterally, enterally, or topically. Illustrative examples of parenteral administration include, but are not limited to, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. Illustrative examples of enteral administration include, but are not limited to oral, inhalation, intranasal, sublingual, and rectal administration. Illustrative examples of topical administration include, but are not limited to, transdermal and vaginal administration. In particular embodiments, an agent or composition is administered parenterally, optionally by intravenous administration or oral administration to a subject.

In one embodiment, a composition of the present invention comprises a pharmaceutically acceptable composition. In one embodiment, the phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In one embodiment, a composition of the present invention is administered in a therapeutically effective amount. In one embodiment, a "therapeutically effective amount" is intended to include an amount of a compound of the present invention alone or an amount of the combination of compounds claimed or an amount of a compound of the present invention in combination with other active ingredients effective to act as an inhibitor to a NOTCH receptor, effective to inhibit gamma secretase, or effective to treat or prevent proliferative diseases such as cancer. In one embodiment, a "therapeutically effective amount" of a composition of the invention is that amount of composition which is sufficient to provide a beneficial effect to the subject to which the composition is administered.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

In one embodiment, "treating" refers to, in one embodiment, therapeutic treatment and, in another embodiment, prophylactic or preventative measures. In one embodiment, the goal of treating is to prevent or lessen the targeted pathologic condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, the term "decreasing the size of the tumor" as used herein is assessed using the "Response Evaluation Criteria In Solid Tumors" (RECIST). In one embodiment, RECIST measures reduction in tumor size by measuring the longest dimension of a target lesion. In one embodiment, the target lesion is selected on the basis of its size (lesion with the longest diameter) and its suitability for accurate repeated measurements (either by imaging techniques or clinically). In one embodiment, all other lesions (or sites of disease) are identified as non-target lesions and are also recorded at baseline. Measurements of these lesions are not required, but the presence or absence of each is noted throughout follow-up.

In one embodiment, the term "decreasing the volume of the tumor" as used herein is assessed using the radiological tumor response evaluation criteria. In one embodiment, the maximum diameter (width) of the tumor is measured in two dimensions in the translation plane and its largest perpendicular diameter on the same image (thickness), according to the World Health Organization (WHO).

According to any of the methods of the present invention and in one embodiment, a subject as described herein is human. In another embodiment, the subject is a mammal. In another embodiment, the subject is a primate, which in one embodiment, is a non-human primate. In another embodiment, the subject is murine, which in one embodiment is a mouse, and, in another embodiment is a rat. In another embodiment, the subject is canine, feline, bovine, equine, caprine, ovine, porcine, simian, ursine, vulpine, or lupine. In one embodiment, the subject is a chicken or fish.

In one embodiment, the compositions as described herein comprise the components of the composition (i.e., one or more compounds of Formula (I)) as described herein. In another embodiment, the compositions as described herein consist of the components of the composition (i.e., one or more compounds of Formula (I)) as described herein). In another embodiment, the compositions as described herein consist essentially of the components of the composition (i.e., one or more compounds of Formula (I)) as described herein.

It is to be understood that the compositions and methods of the present invention comprising the elements or steps as described herein may, in another embodiment, consist of those elements or steps, or in another embodiment, consist essentially of those elements or steps. In some embodiments, the term "comprise" refers to the inclusion of the indicated active agents, such as the gamma secretase inhibitor, as well as inclusion of other active agents, and pharmaceutically or physiologically acceptable carriers, excipients, emollients, stabilizers, etc., as are known in the pharmaceutical industry. In some embodiments, the term "consisting essentially of" refers to a composition, whose only active ingredients are the indicated active ingredients. However, other compounds may be included which are for stabilizing, preserving, etc. the formulation, but are not involved directly in the therapeutic effect of the indicated active ingredients. In some embodiments, the term "consisting essentially of" may refer to components which facilitate the release of the active ingredient. In some embodiments, the term "consisting" refers to a composition, which contains the active ingredients and a pharmaceutically acceptable carrier or excipient.

Timing and Site of Administration

In one embodiment, in the methods of the present invention, the administration of one or more anti-cancer agents occurs prior to the administration of the compound of Formula (I). In another embodiment, in the methods of the present invention, the administration of one or more anti-cancer agents occurs concurrent with the administration of the compound of Formula (I). In another embodiment, in the methods of the present invention, the administration of one or more anti-cancer agents occurs following the administration of the compound of Formula (I). In one embodiment, concurrent administration comprises administering a single composition comprising the anti-cancer agent and compound of Formula (I). In another embodiment, concurrent administration comprises administering separate compositions.

In one embodiment, the administration of the anti-cancer agents occurs at the same site as the administration of the compound of Formula (I).

In one embodiment, the compound of Formula (I) is administered several days before and after the administration of the anti-cancer agent. In one embodiment, the compound of Formula (I) is administered 1, 2, 3, 4, or 5 days prior to the administration of the anti-cancer agent. In one embodiment, the compound of Formula (I) is administered 1, 2, 3, 4, or 5 days subsequent to the administration of the anti-cancer agent. In another embodiment, the compound of Formula (I) is administered one day before and up to 9 days following anti-cancer agent administration. In another embodiment, the compound of Formula (I) is administered one day before and on days 1, 8, and 9 following anti-cancer agent administration. In another embodiment, the compound of Formula (I) is administered one day before and 9 days following anti-cancer agent administration. In another embodiment, the compound of Formula (I) is administered one day before and daily for 9 days following anti-cancer agent administration. In another embodiment, the compound of Formula (I) is administered one day before and on day 9 following anti-cancer agent administration.

In some embodiments, one or more compositions of the present invention are administered at least once during a treatment cycle. In some embodiments, the compositions of the present invention are administered to the subject on the same days. In some embodiments, the compositions of the present invention are administered to the subject on the different days. In some embodiments, one or more compositions of the present invention are administered to the subject on the same days and on different days according to treatment schedules.

In particular embodiments, one or more compositions of the present invention are administered to the subject over one or more treatment cycles. A treatment cycle can be at least two, at least three, at least four, at least five, at least six, at least seven, at least 14, at least 21, at least 28, at least 48, or at least 96 days or more. In one embodiment, a treatment cycle is 28 days. In certain embodiments, the compositions are administered over the same treatment cycle or concurrently over different treatment cycles assigned for each composition. In various embodiments, the treatment cycle is determined by a health care professional based on conditions and needs of the subject.

In some embodiments, a composition is administered on at least one day, at least two days, at least three days, at least four days, at least five days, at least six days, at least seven days, at least eight days, at least nine days, at least ten days, at least eleven days, at least twelve days, at least 13 days, at least 14 days, at least 21 days, or all 28 days of a 28 day treatment cycle. In particular embodiments, a composition is administered to a subject once a day. In other particular embodiments, a composition is administered twice a day.

In one embodiment, one or more of the compositions as described herein are administered in one to four doses per day. In one embodiment, one or more of the compositions as described herein are administered once per day. In another embodiment, one or more of the compositions as described herein are administered twice per day. In another embodiment, one or more of the compositions as described herein are administered three times per day. In another embodiment, one or more of the compositions as described herein are administered four times per day. In another embodiment, one or more of the compositions as described herein are administered once every two days, once every three days, twice a week, once a week, once every 2 weeks, once every 3 weeks.

In one embodiment, one or more of the compositions as described herein are administered for 7 days to 28 days. In another embodiment, one or more of the compositions as described herein are administered for 7 days to 8 weeks. In another embodiment, one or more of the compositions as described herein are administered for 7 days to 50 days. In another embodiment, one or more of the compositions as described herein are administered for 7 days to six months. In another embodiment, one or more of the compositions as described herein are administered for 7 days to one and half years. In another embodiment, one or more of the compositions as described herein are administered for 14 days to 12 months. In another embodiment, one or more of the compositions as described herein are administered for 14 days to 3 years. In another embodiment, one or more of the compositions as described herein are administered for several years. In another embodiment, one or more of the compositions as described herein are administered for one month to six months.

In one embodiment, one or more of the compositions as described herein are administered for 7 days. In another embodiment, one or more of the compositions as described herein are administered for 14 days. In another embodiment, one or more of the compositions as described herein are administered for 21 days. In another embodiment, one or more of the compositions as described herein are administered for 28 days. In another embodiment, one or more of the compositions as described herein are administered for 50 days. In another embodiment, one or more of the compositions as described herein are administered for 56 days. In another embodiment, one or more of the compositions as described herein are administered for 84 days. In another embodiment, one or more of the compositions as described herein are administered for 90 days. In another embodiment, one or more of the compositions as described herein are administered for 120 days.

The number of times a composition is administered to a subject in need thereof depends on the discretion of a medical professional, the disorder, the severity of the disorder, and the subject's response to the formulation. In some embodiments, a composition disclosed herein is administered once to a subject in need thereof with a mild acute condition. In some embodiments, a composition disclosed herein is administered more than once to a subject in need thereof with a moderate or severe acute condition. In the case wherein the subject's condition does not improve, upon the doctor's discretion the composition may be administered chronically, that is, for an extended period of time, including throughout the duration of the subject's life in order to ameliorate or otherwise control or limit the symptoms of the subject's disease or condition.

In the case wherein the subject's status does improve, upon the doctor's discretion the composition may administered continuously; or, the dose of drug being administered may be temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Kits

The present invention further comprises combinations of the compositions of the present invention and, optionally, one or more additional agents in kit form, e.g., where they are packaged together or placed in separate packages to be sold together as a kit, or where they are packaged to be formulated together.

In certain embodiments, the kit comprises a therapeutic or prophylactic composition containing an effective amount of the compound of Formula (I) or Formula (III) or Compound (1), as described herein, which in one embodiment, comprises 4 mg of the compound of Formula (I). In certain embodiments, the kit comprises a sterile container which contains therapeutic or prophylactic agents; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired, the composition(s) are provided together with instructions for administering the composition(s) to a subject having or at risk of developing an ACC tumor. The instructions will generally include information about the use of the composition for the treatment or prevention of an ACC tumor. In other embodiments, the instructions include at least one of the following: description of the therapeutic agent; dosage schedule and administration for treatment or prevention of an ACC tumor or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

Example 1

PK/PD Analyses of ACC Patients in a Phase 1 Study of Intravenous (IV) Administration of Compound (1) in Patients with Advanced or Metastatic Solid Tumors A Phase I, ascending multiple-dose study of intravenous (IV) administration of Compound (1) in patients with advanced or metastatic solid tumors was conducted. In a Phase 1 solid tumor study, two ACC patients were treated with Compound (1), an investigational gamma secretase inhibitor (El-Khoueiry A B, et al. J Clin Oncol. 2018; 36. Abstract 2515, incorporated herein by reference). One patient with an NRR (Negative Regulatory Region) activating mutation had a prolonged partial response, the 2nd patient with a PEST mutation had stable disease.

ACC is a rare salivary gland malignancy with no standard of care. Chemotherapy resistance limits treatment to surgery/radiation and ~60% of patients will recur. Between 11% to 22% of ACC patients have Notch activating mutations which are associated with high NICD nuclear stain, aggressive disease and poor prognosis. The median overall survival of ACC patients with a Notch1 mutation (n=14) was 29.6 months in comparison with a median overall survival of 121.9 months (n=88) of ACC patients having wild-type Notch1 (FIG. 1).

One of the secondary objectives of this study was to assess the pharmacokinetics (PK) of Compound (1). Another secondary objective was to assess pharmacodynamic (PD) changes in the expression of Notch pathway-related genes, such as Hairy and Enhancer of Split-1 (Hes1) and Deltex-1 (DTX1), in surrogate tissues (peripheral blood cells).

Method: Two ACC patients were administered 4 mg Compound (1) intravenously [IV], once a week [qw or qwk].

PK plasma samples were analyzed for Compound (1) and its metabolite by a validated liquid chromatography-mass spectrometry/mass spectrometry assay.

PD assessments of changes in Hes1 and DTX1 were determined using quantitative real time polymerase chain reaction.

Figure 2A:
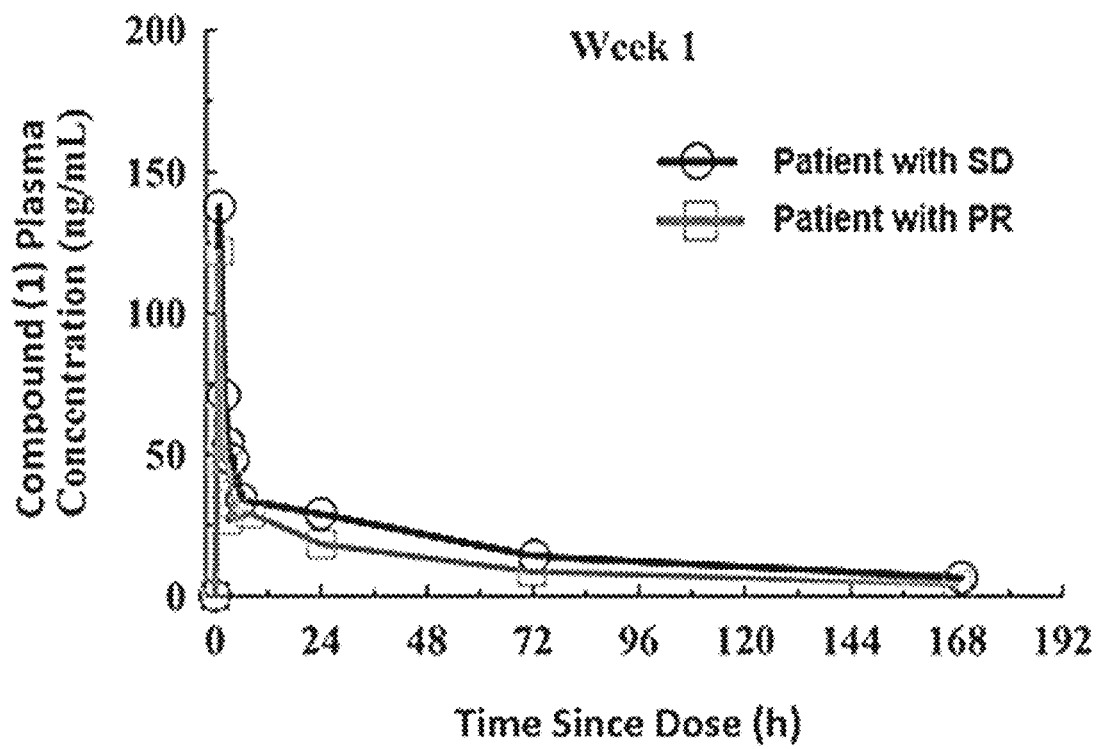
FIG. 2A. Compound (1) plasma concentration profile after administration of 4 mg of Compound (1)—Week 1. Patients were administered 4 mg Compound (1) once per week. Plasma concentration of Compound (1) is presented for one patient with a partial response ("Patient with PR") and one patient with stable disease ("Patient with SD") from 0 to 168 hours after the first treatment with Compound (1). Plasma concentration of Compound (1) was determined via a validated liquid chromatography-mass spectrometry/mass spectrometry assay.
Figure 2B:
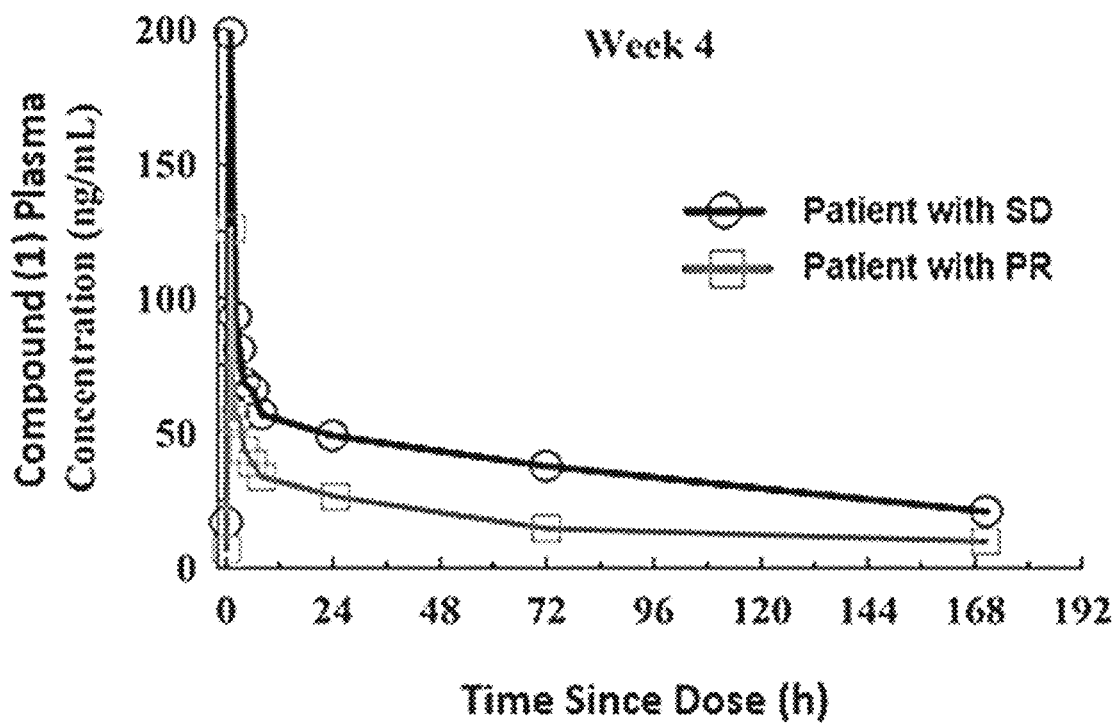
FIG. 2B. Compound (1) plasma concentration profile after administration of 4 mg of Compound (1)—Week 4. Patients were administered 4 mg Compound (1) once per week. Plasma concentration of Compound (1) is presented for one patient with a partial response ("Patient with PR") and one patient with stable disease ("Patient with SD") from 0 to 168 hours after the fourth week of treatment with Compound (1). Plasma concentration of Compound (1) was determined via a validated liquid chromatography-mass spectrometry/mass spectrometry assay.

Results: Both ACC patients maintained detectable Compound (1) plasma concentration for more than 72 hours after the first administration (FIG. 2A) and more than 168 hours after the fourth administration (FIG. 2B).

Figure 2C:
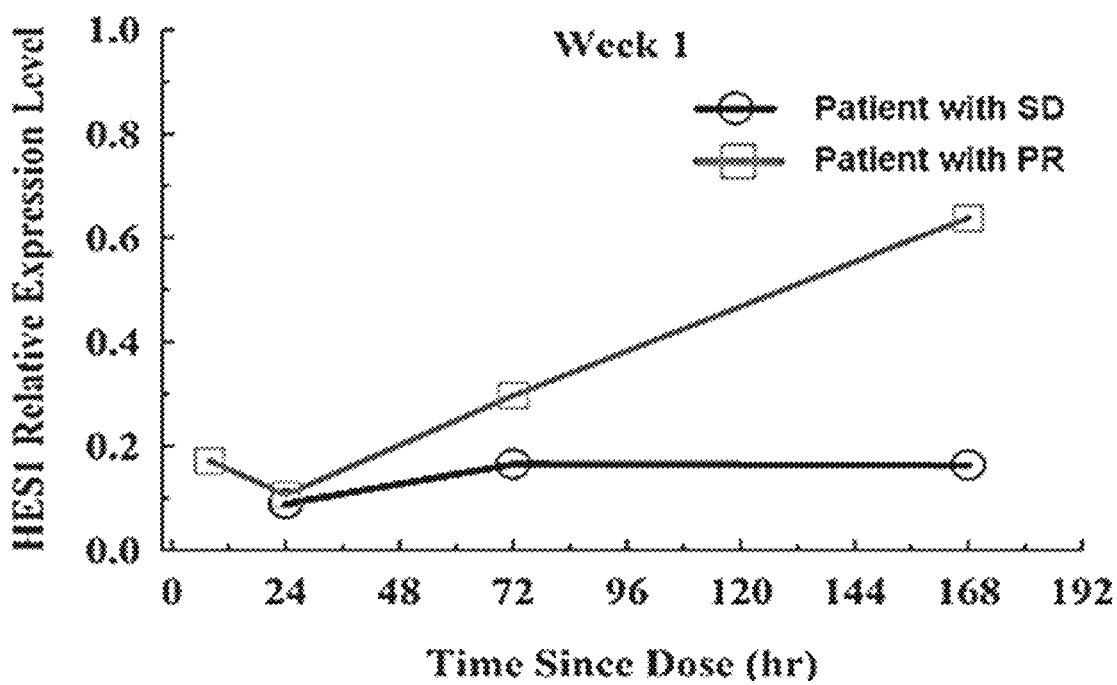
FIG. 2C. Pharmacodynamic effect of Compound (1) administration on expression of Hes1—Week 1. Hes1 expression in peripheral blood was determined in patients after administration of 4 mg Compound (1) once per week using quantitative real time polymerase chain reaction. Data are presented for one patient with a partial response ("Patient with PR") and one patient with stable disease ("Patient with SD") for up to 168 hours after the first week of treatment with Compound (1).
Figure 2D:
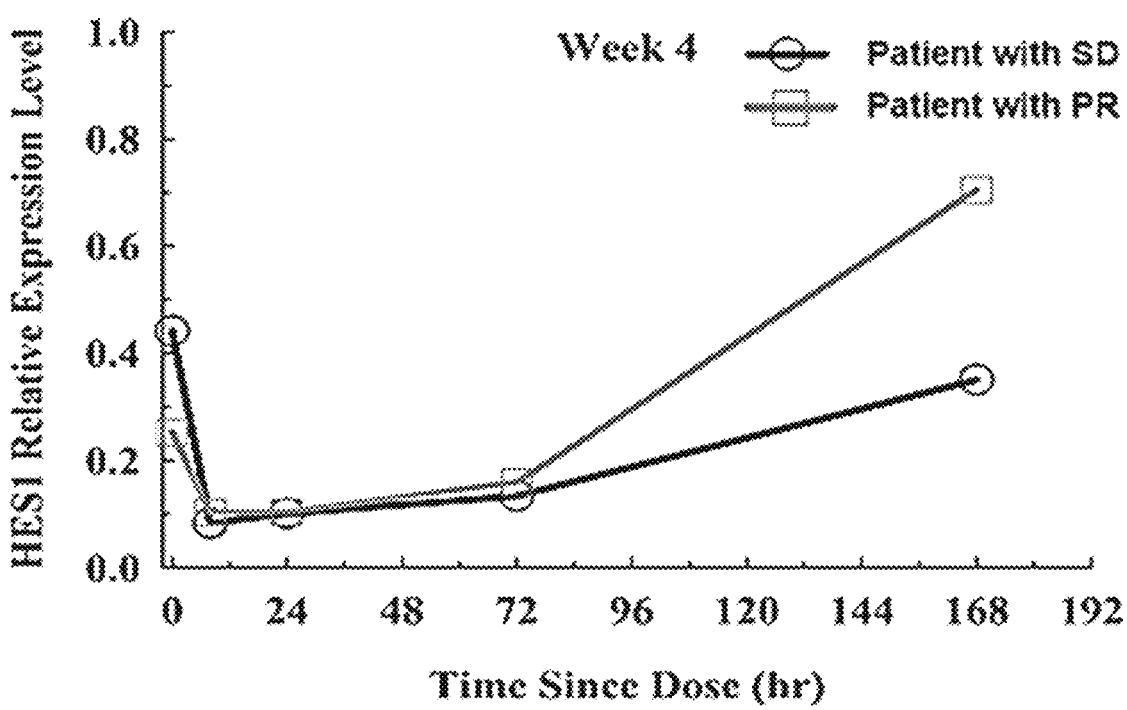
FIG. 2D. Pharmacodynamic effect of Compound (1) administration on expression of Hes1—Week 4. Hes1 expression in peripheral blood was determined in patients after administration of 4 mg Compound (1) once per week using quantitative real time polymerase chain reaction. Data are presented for one patient with a partial response ("Patient with PR") and one patient with stable disease ("Patient with SD") for up to 168 hours after the fourth week of treatment with Compound (1).

Both patients' PK profiles were characterized by sufficient exposure of Compound (1) to result in a sustained PD response. Specifically, there was a >50% reduction in the expression of the Notch target gene HES1 in peripheral blood for at least 120 hours after dosing (FIGS. 2C, 2D).

Figure 2E:
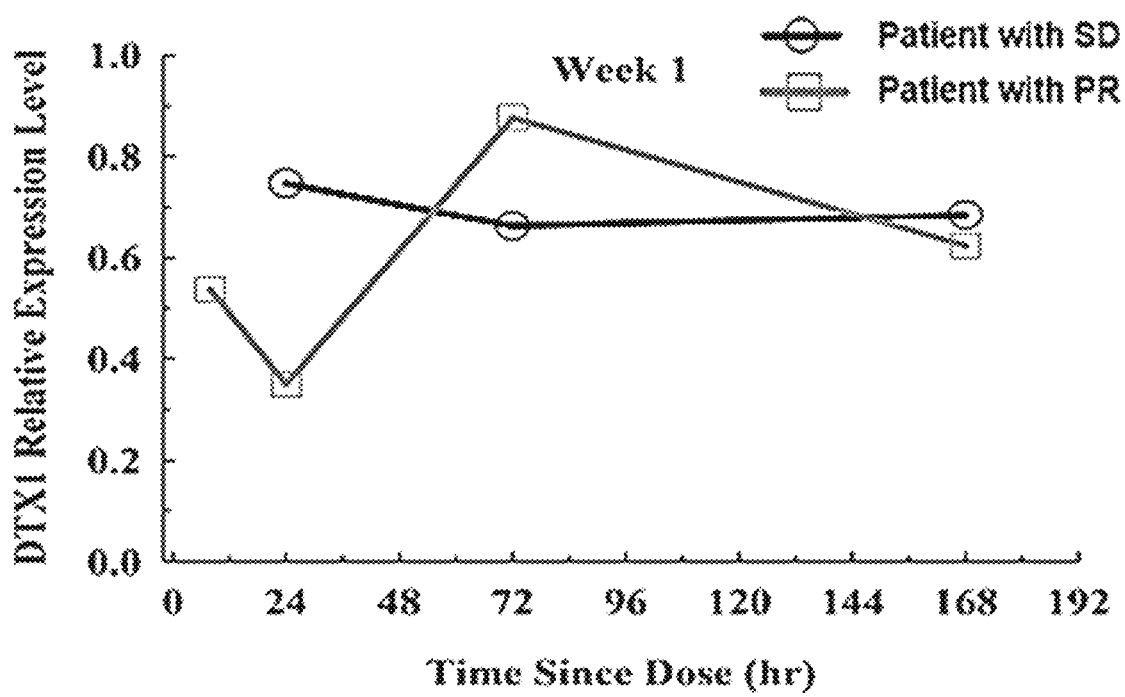
FIG. 2E. Pharmacodynamic effect of Compound (1) administration on expression of DTX1—Week 1. DTX1 expression in peripheral blood was determined in patients after administration of 4 mg Compound (1) once per week using quantitative real time polymerase chain reaction. Data are presented for one patient with a partial response ("Patient with PR") and one patient with stable disease ("Patient with SD") for up to 168 hours after the first week of treatment with Compound (1).
Figure 2F:
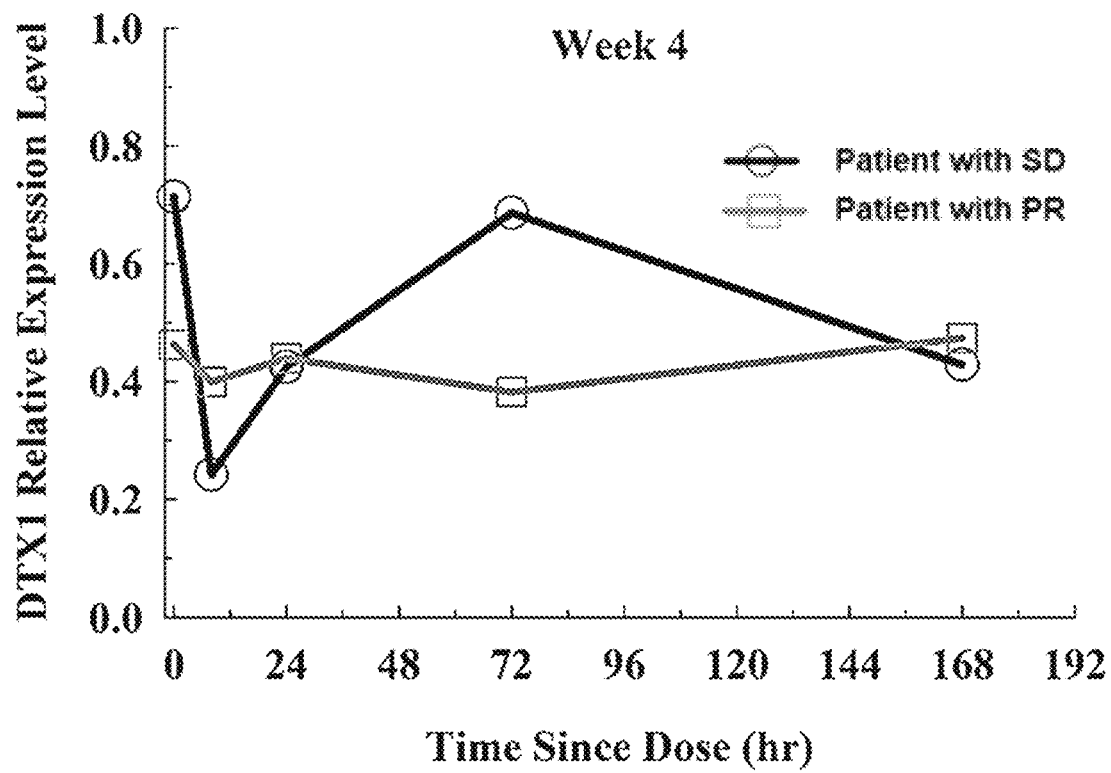
FIG. 2F. Pharmacodynamic effect of Compound (1) administration on expression of DTX1—Week 4. DTX1 expression in peripheral blood was determined in patients after administration of 4 mg Compound (1) once per week using quantitative real time polymerase chain reaction. Data are presented for one patient with a partial response ("Patient with PR") and one patient with stable disease ("Patient with SD") for up to 168 hours after the fourth week of treatment with Compound (1).

Additionally, Compound (1) treatment of both ACC patients reduced the relative expression of the Notch target gene DTX1 in peripheral blood at Week 1 (FIG. 2E) and Week 4 (FIG. 2F). After the fourth treatment with Compound (1), there was a >50% reduction in the expression of the DTX1 in peripheral blood of the patient with PR, which lasted more than 168 hours (FIG. 2F). In the SD patient, the >50% reduction in the expression of the DTX1 in peripheral blood lasted at least 24 hours (FIG. 2F).

Figure 2G:
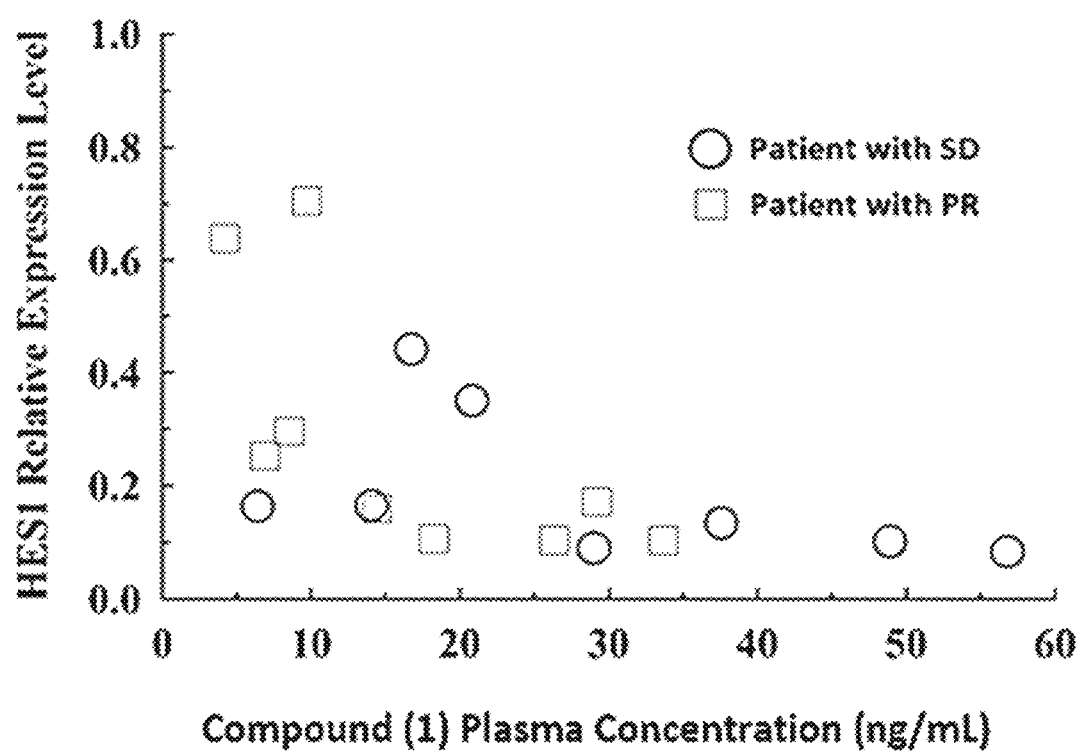
FIG. 2G. Pharmacokinetic/Pharmacodynamic effect of Compound (1) according to expression of Hes1 relative to baseline. Patients were administered 4 mg Compound (1) once per week, and plasma concentration of Compound (1) and Hes1 expression in patients was plotted. Plasma concentration of Compound (1) was determined via a validated liquid chromatography-mass spectrometry/mass spectrometry assay. Hes1 expression was determined using quantitative real time polymerase chain reaction. Data are presented for one patient with a partial response ("Patient with PR") and one patient with stable disease ("Patient with SD").

Both patients had an extended PK profile with a sustained pharmacodynamic response (>50% inhibition of HES1 in peripheral blood). Additionally, both showed inhibition of HES1 expression that was dependent on the concentration of Compound (1) in plasma (FIG. 2G).

Example 2

Compound (1)—Mediated Tumor Inhibition in Notch Mutated ACC PDX Models

Goal: To evaluate Notch inhibitor monotherapy and combination (combo) therapy in Adenoid Cystic Carcinoma (ACC) Patient Derived Xenograft (PDX) models with and without activating Notch mutations (mt).

Methods: Four ACC PDX models were evaluated: ACCx9 (Notch1 mt: NRR activating mutation 11680N), ACCx11 (Notch1 mt, 3' tandem duplication), ACCx6 (Notch1 wt), ACCx5M1 (Notch1 VUS, not predicted to be activating). Activated Notch1 (nuclear immunohistochemistry (IHC) stain) was confined to the Notch mt models (ACCx9 and ACCx11). Tumors (~70 mg) were subcutaneously implanted into 6-12 week-old athymic nude female mice. Upon reaching 150-300 $mm^3$ tumor volume, mice were randomized to treatment (n=5), or vehicle (n=10) arms. Compound (1) was dosed at 7.5 mg/kg orally (4 days on/3 days off) as a single agent or at 3 or 5 mg/kg in combination with cisplatin (3 mg/kg intraperitoneally; once a week (qwk)) or everolimus (10 mg/kg; orally; once a day (qd)) (see dosing schedule in Table 1). In addition, cisplatin and everolimus were given to separate treatment groups as monotherapy. Tumor volumes and animal weight were collected twice a week.

TABLE 1

Dosing Schedules for Compound (1), Cisplatin, and Everolimus

| Treatment | Dosing Schedule |
|---|---|
| Compound (1) | 7.5 mg/kg PO, 4 days on/3 days off |
| Cisplatin | 3 mg/kg, IP, qwk |
| Everolimus | 10 mg/kg, PO, qd |
| Compound (1) + cisplatin | Compound (1): 5 mg/kg, PO, 4 days on/3 days off |
| | Cisplatin: 3 mg/kg, IP, qwk |
| Compound (1) + everolimus | Compound (1): 3 mg/kg, PO, 4 days on/3 days off |
| | Everolimus: 10 mg/kg, PO, qd |

IP = intraperitoneally;
PO = orally;
qd = once a day;
qwk = once a week

Figure 3A:
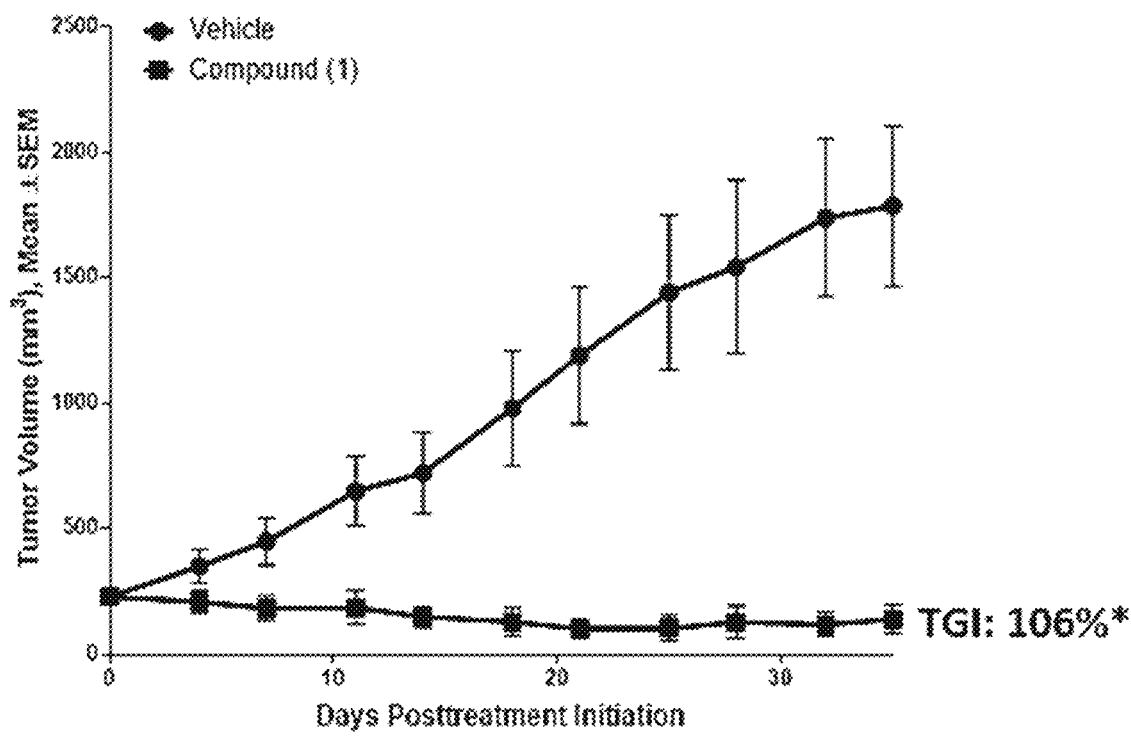
FIG. 3A. Effect of Compound (1) treatment on tumor volume in ACCx9-Notch1 mutant tumors. Tumor volume in mice bearing an ACCx9-Notch1 mutant tumor was measured over a 35-day period in mice administered either vehicle or 7.5 mg/kg Compound (1) on a treatment schedule of 4 days on/3 days off. *P<0.0001 SEM=standard error of the mean; TGI=tumor growth inhibition.
Figure 3B:
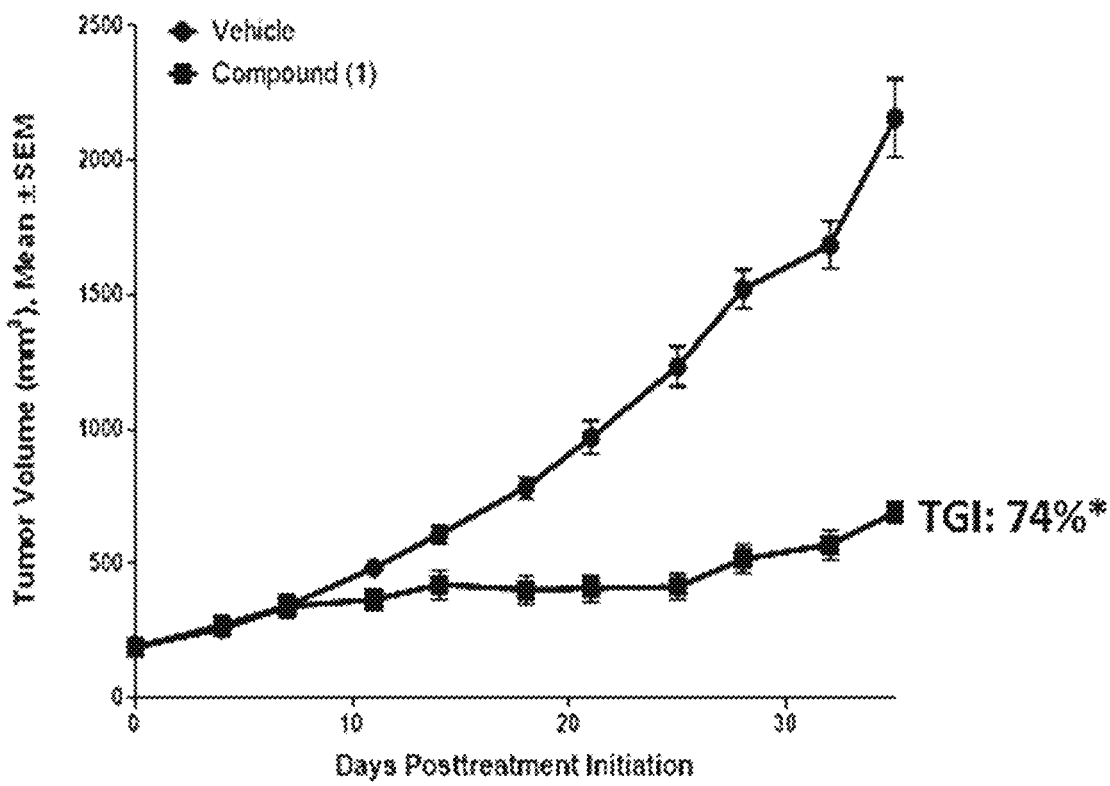
FIG. 3B. Effect of Compound (1) treatment on tumor volume in ACCx11-Notch1 mutant tumors. Tumor volume in mice bearing an ACCx11-Notch1 was measured over a 35-day period in mice administered either vehicle or 7.5 mg/kg Compound (1) on a treatment schedule of 4 days on/3 days off. *P<0.0001 SEM=standard error of the mean; TGI=tumor growth inhibition.
Figure 3C:
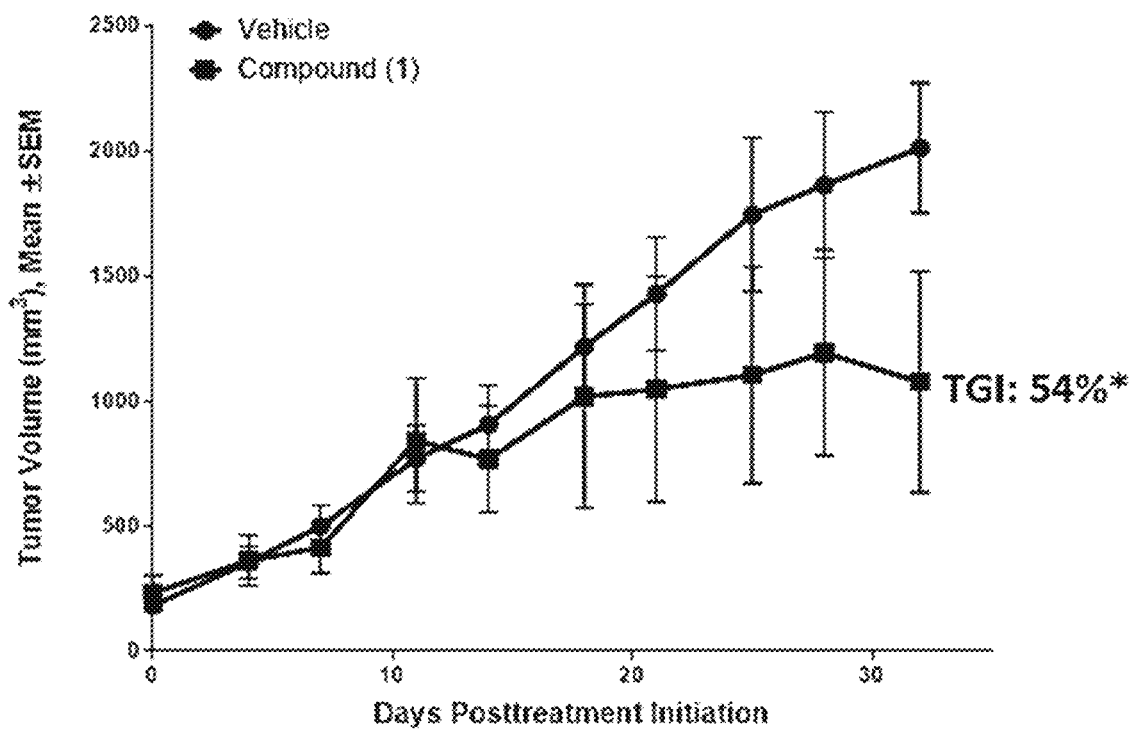
FIG. 3C. Effect of Compound (1) treatment on tumor volume in ACCx6 model tumors. Tumor volume in mice bearing an ACCx6 was measured over a 35-day period in mice administered either vehicle or 7.5 mg/kg Compound (1) on a treatment schedule of 4 days on/3 days off. NS=not statistically significant; SEM=standard error of the mean; TGI=tumor growth inhibition.
Figure 3D:
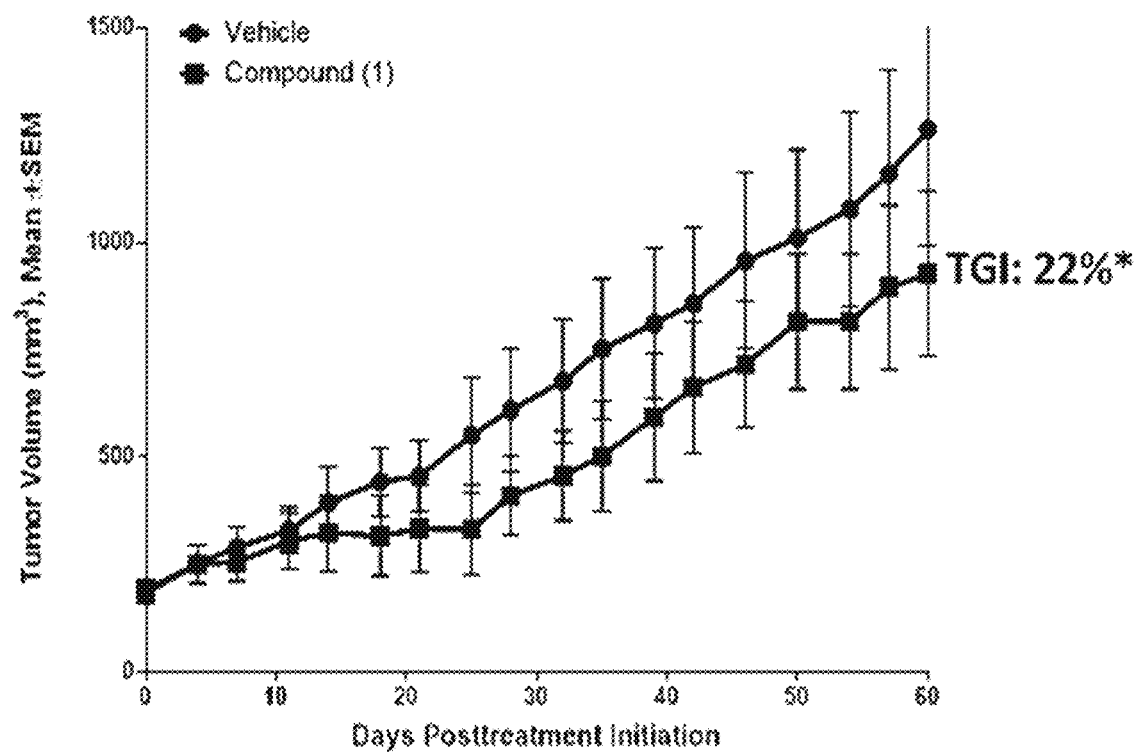
FIG. 3D. Effect of Compound (1) treatment on tumor volume in ACCx5M1 model mutant tumors. Tumor volume in mice bearing an ACCx5M1 tumor was measured over a 35-day period in mice administered either vehicle or 7.5 mg/kg Compound (1) on a treatment schedule of 4 days on/3 days off. NS=not statistically significant; SEM=standard error of the mean; TGI=tumor growth inhibition.

Results: Significant tumor growth inhibition (TGI) was seen with Compound (1) monotherapy compared to vehicle treatment in both Notch mt models (ACCx9; 106% TGI P<0.0001, and ACCx11; 74% TGI P<0.0001, FIGS. 3A, 3B, 3E, 3F). Compound (1) had no significant effect on tumors lacking Notch activating mutations (ACCx6: 54% TGI, ACCx5M1: 22% TGI, FIGS. 3C, 3D).

Figure 3E:
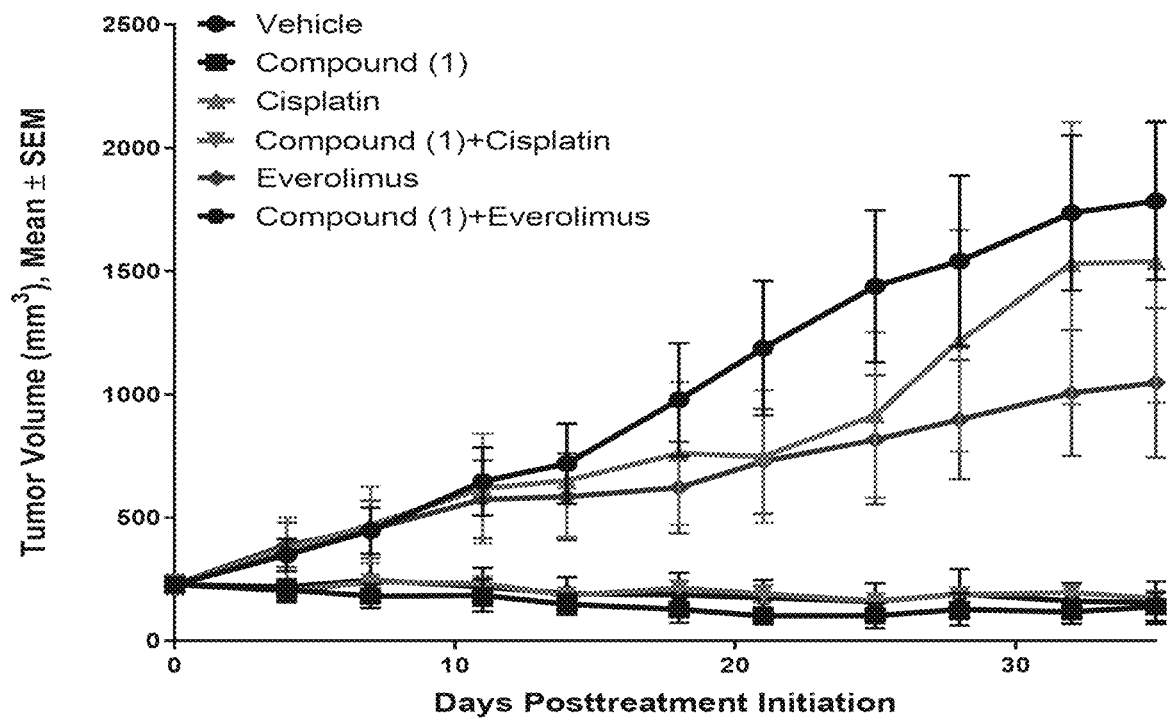
FIG. 3E. Effect of combined therapy of Compound (1) with cisplatin or everolimus on tumor volume in ACCx9-Notch1 mutant tumors. Tumor volume in mice bearing an ACCx9-Notch1 mutant tumor was measured over a 35-day period in mice administered vehicle, Compound (1) (7.5 mg/kg PO, 4 days on/3 days off), cisplatin (3 mg/kg, IP, once a week); everolimus (10 mg/kg once a day); a combination of Compound (1) (5 mg/kg, PO, 4 days on/3 days off) and cisplatin (3 mg/kg, IP, qwk); or a combination of Compound (1) (3 mg/kg, PO, 4 days on/3 days off) and everolimus (10 mg/kg, PO, qd). *P<0.0001; †P<0.05; NS=not statistically significant; SEM=standard error of the mean; TGI=tumor growth inhibition.
Figure 3F:
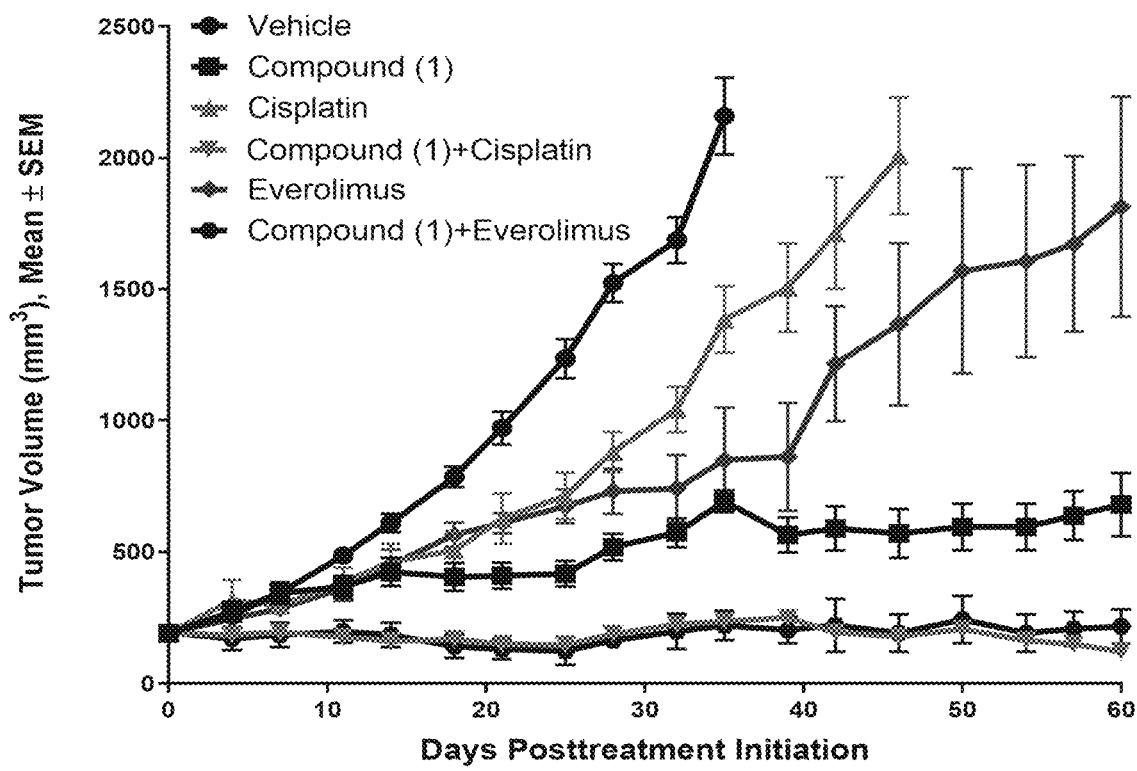
FIG. 3F. Effect of combined therapy of Compound (1) with cisplatin or everolimus on tumor volume in ACCx11-Notch1 mutant tumors. Tumor volume in mice bearing an ACCx11-Notch1 was measured over a 35-day period in mice administered vehicle, Compound (1) (7.5 mg/kg PO, 4 days on/3 days off), cisplatin (3 mg/kg, IP, once a week); everolimus (10 mg/kg once a day); a combination of Compound (1) (5 mg/kg, PO, 4 days on/3 days off) and cisplatin (3 mg/kg, IP, qwk); or a combination of Compound (1) (3 mg/kg, PO, 4 days on/3 days off) and everolimus (10 mg/kg, PO, qd). *P<0.0001; †P<0.05; NS=not statistically significant; SEM=standard error of the mean; TGI=tumor growth inhibition.

Cisplatin monotherapy (3 mg/kg once a week) had no significant effect on Notch mt models (ACCx9; 16% TGI, ACCx11; 39% TGI, FIGS. 3E, 3F). Everolimus monotherapy (10 mg/kg once a day) also had no significant effect on the ACCx9 Notch mt model, but had a small but significant decrease in tumor volume in the ACx11 Notch mt model (ACCx9; 47% TGI, ACCx11; 67% TGI †P<0.05, FIGS. 3E, 3F).

Addition of cisplatin or everolimus to Compound (1) provided no additional benefit compared to Compound (1) alone in the ACCx9 model (104% and 105% TGI respectively P<0.0001; FIG. 3E). In the ACCx11 model, combination therapies further inhibited tumor volume compared to Compound (1) alone (FIG. 3F), but the benefit did not reach statistical significance compared to Compound (1) alone (98% TGI P<0.0001 for cisplatin combo and 99% TGI P<0.0001for everolimus combo compared to vehicle). Interestingly, the ACCx6 Notch wt model was sensitive to everolimus (75% TGI P=0.027) with no significant benefit of adding Compound (1) (data not shown).

Conclusion: Compound (1) monotherapy had a significant anti-tumor effect (over 70% TGI) in ACC PDX tumors with Notch activating mutations and lacked effectiveness in tumors lacking such mutations. Cisplatin and everolimus as monotherapies did not significantly inhibit tumor growth in ACC PDX models with Notch1-activating mutations: cisplatin showed no effect and everolimus a modest effect. Cisplatin and everolimus administered in combination with Compound (1) did not add significant benefit compared with Compound (1) monotherapy in ACC PDX models with Notch1-activating mutations. These data support the clinical development of Compound (1) as a targeted monotherapy for ACCs with Notch activating mutations.

Example 3

Immunohistochemistry Staining of ACC PDX Models Treated with Compound (1)

Goal: To evaluate Notch activation and antitumor activity in ACC PDX models treated with Compound (1) by immunohistochemistry (IHC) staining. As a hallmark of Notch activation, the expression of Notch1 Intracellular Domain (NICD1) in the nucleus was evaluated by IHC. Ki67 IHC staining was used to evaluate cell proliferation and MYC, a well-known oncogene, which is a Notch target gene, was also stained. An additional marker for Notch activation that was evaluated is the expression of the Notch target HES1.

Methods: Two ACC PDX models were evaluated: ACCx11 (Notch1 mt, 3' tandem duplication), and ACCx5M1 (Notch1 VUS, not predicted to be activating) as described in Example 2. All IHC was performed on the Leica Bond III automated staining platform using the following antibodies: Antibody c-Myc (Abcam, catalogue #ab32072, clone Y69), at a 1:100 dilution; Antibody Ki-67 (Biocare, catalogue #CRM325, clone SP6) at a 1:100 dilution; Antibody Notch 1 (ICN1) (Cell Signaling Technology, catalogue #4147, clone Val1744/D3B8), at a 1:50 dilution; Antibody Caspase-3 (Cell Signaling Technology, catalogue #9664, clone Asp175/5A1E), at a 1:150 dilution using the Leica Biosystems Refine Detection Kit with citrate antigen retrieval; and Antibody HES1 (Cell Signaling Technology, catalogue #11988, clone D6P2U), at a 1:100 dilution. c-Myc, Ki-67 and Notch 1 were detected using the Leica Biosystems Refine Detection Kit with EDTA antigen retrieval, and HES1 and Caspase-3 were detected using the Leica Biosystems Refine Detection Kit with citrate antigen retrieval.

Figure 4A:
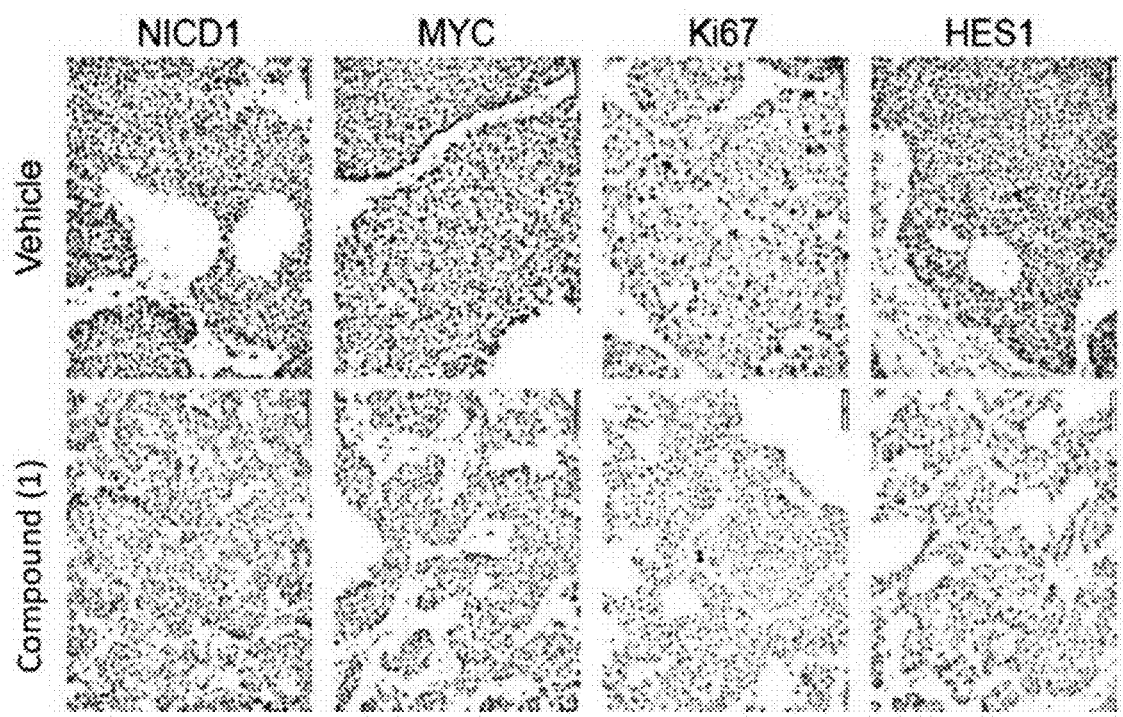
FIG. 4A. Immunohistochemical staining of ACCx11-Notch1 mutant tumors following treatment with Compound (1). ACCx11-Notch1 mutant tumor-bearing mice were administered either vehicle or 7.5 mg/kg Compound (1) on a treatment schedule of 4 days on/3 days off. Notch1 intracellular domain (NICD1), MYC, Ki67 and HES1 were evaluated in tumor tissue from the vehicle- and Compound (1)-treated mice by immunohistochemistry.
Figure 4B:
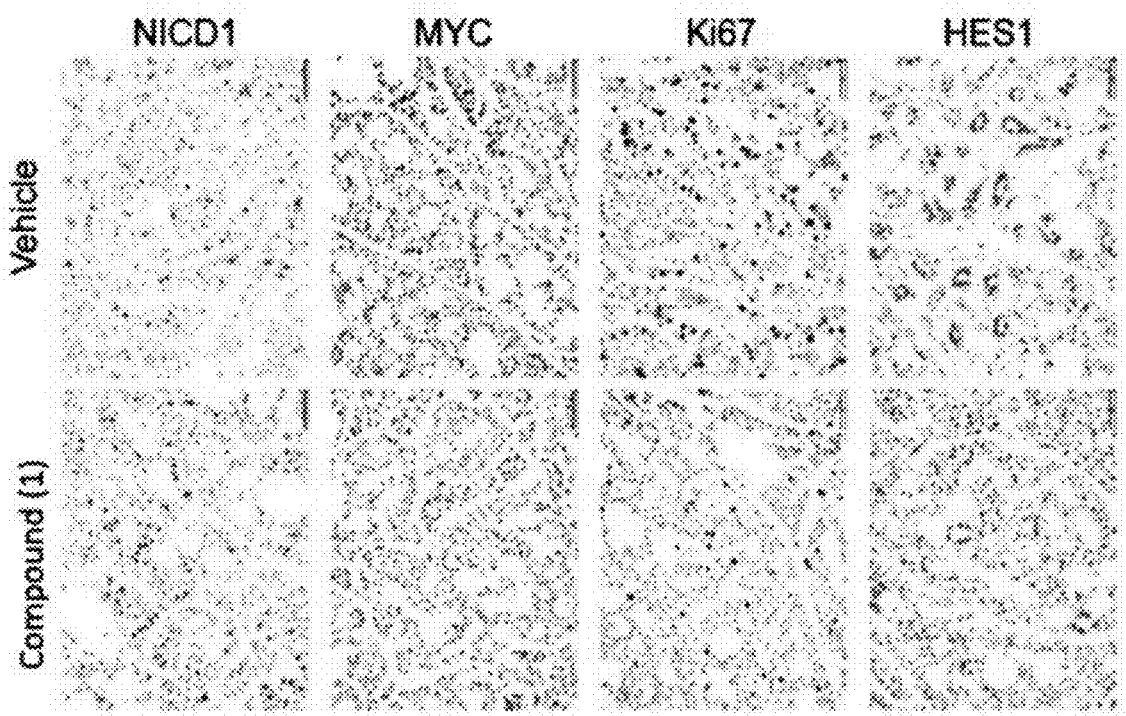
FIG. 4B. Immunohistochemical staining of ACCx5M1 model tumors following treatment with Compound (1). ACCx5M1 tumor-bearing mice were administered either vehicle or 7.5 mg/kg Compound (1) on a treatment schedule of 4 days on/3 days off. Notch1 intracellular domain (NICD1), MYC, Ki67 and HES1 were evaluated in tumor tissue from the vehicle- and Compound (1)-treated mice by immunohistochemistry.

Results: The expression of NICD1 in the nucleus was very high in the vehicle-treated ACCx11 Notch mutant model (FIG. 4A), but not in the ACCx5M1 Notch WT model (FIG. 4B). NICD1 staining was completely abolished by Compound (1) treatment in the Notch1 mutant model, confirming Notch inhibition by Compound (1) (FIG. 4A).

A pronounced reduction of cell proliferation was observed in Compound (1)-treated Notch mutant model using Ki67 staining. A pronounced reduction of the Notch target gene MYC in Compound (1)-treated Notch mutant model was also observed, further confirming Notch inhibition by Compound (1). HES1 protein expression was high in vehicle-treated tumors and was moderately affected by Compound (1) treatment (FIG. 4A).

Conclusion: Compound (1) monotherapy inhibited Notch and showed significant reduction in cell proliferation in ACC PDX tumors with Notch activating mutations and lacked effectiveness in tumors lacking such mutations.

Example 4

Comparative Antitumor Activity of Compound (1) Relative to Other Notch Inhibitors in the ACCx9 PDX Model Goal: To compare the antitumor activity of Compound (1) with the following Notch inhibitors: CB-103, a small molecule which is a protein-protein interaction inhibitor (Cellestia Biotech presentation, Basel Breast Cancer Consortium, October 2017, incorporated herein by reference), MRK-003, a small molecule which is γ-secretase inhibitor (GSI) (Stoeck A, et al. Cancer Discov. 2014; 4:1154-1167, incorporated herein by reference), and the monoclonal antibody brontictuzumab (Ferrarotto R, et al. *J Clin Oncol.* 2017; 35:352-360, incorporated herein by reference) in an ACC PDX model.

Methods: The ACC PDX model ACCx9 was evaluated using the same method described in Example 2. Compound (1) was dosed at 7.5 mg/kg orally (4 days on/3 days off). Two groups of mice received treatment with different doses of MRK-003: 150 mg/kg and 300 mg/kg once a week (qwk). Brontictuzumab was administered at 10 mg/kg twice a week (q2wk). Data for MRK-003 was adapted from Stoeck A, et al. Cancer Discov. 2014; 4:1154-1167. Data for brontictuzumab was adapted from Ferrarotto R, et al. J Clin Oncol. 2017; 35:352-360.

Figure 5A:
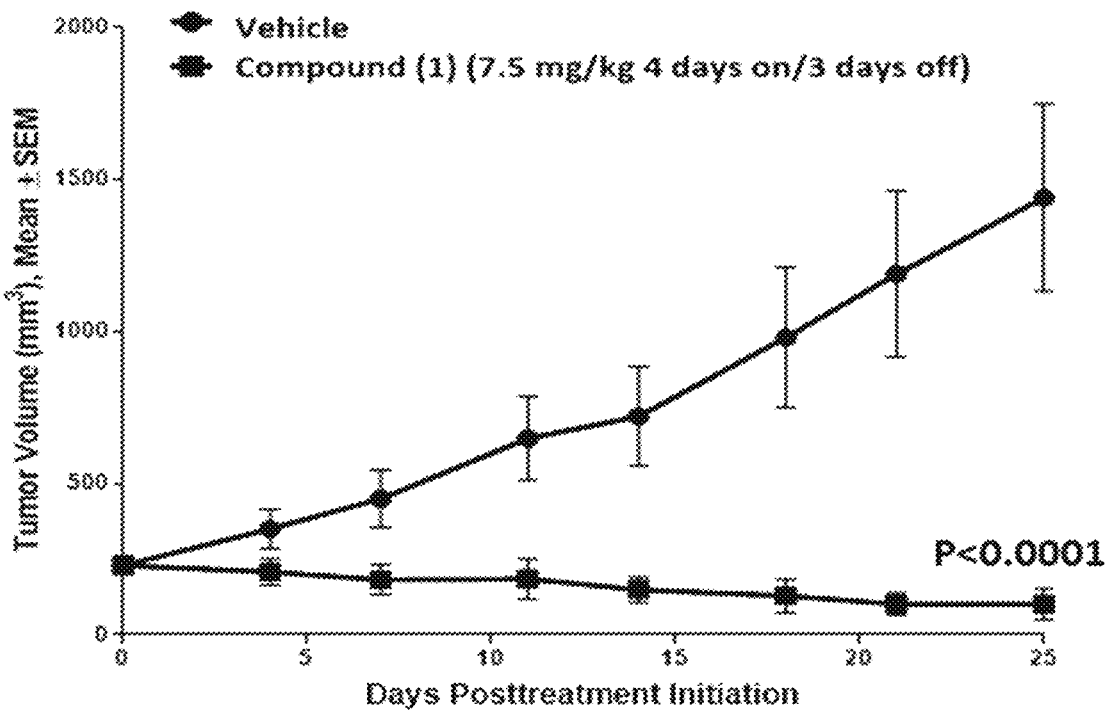
FIG. 5A. Effect of Compound (1) treatment on tumor volume in ACCx9-Notch1 mutant tumors. Tumor volume in mice bearing an ACCx9-Notch1 mutant tumor was measured over a 25-day period in mice administered either vehicle or 7.5 mg/kg Compound (1) on a treatment schedule of 4 days on/3 days off. *P<0.0001 SEM=standard error of the mean.
Figure 5B:
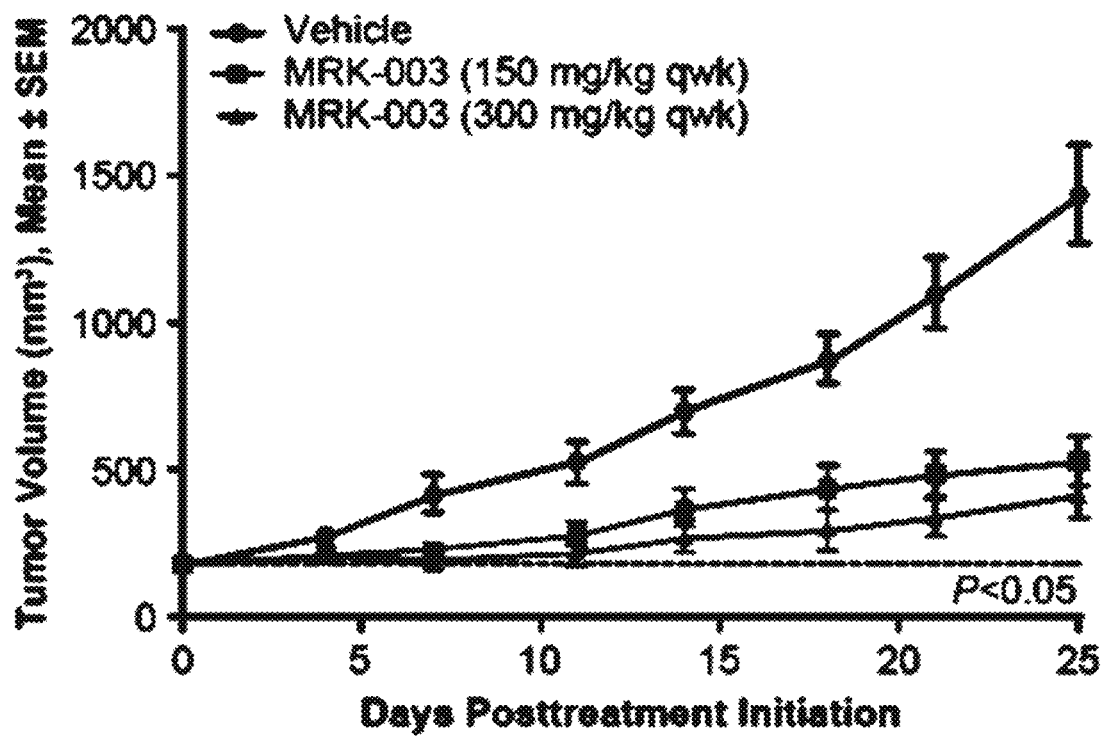
FIG. 5B. Effect of MRK-003 treatment on tumor volume in ACCx9-Notch1 mutant tumors. Tumor volume in mice bearing an ACCx9-Notch1 mutant tumor was measured over a 25-day period in mice administered either vehicle, 150 mg/kg MRK-003 once a week, or 300 mg/kg MRK-003 once a week. MRK-003 is a small molecule which is γ-secretase inhibitor (GSI) (Stoeck A, et al. Cancer Discov. 2014; 4:1154-1167, incorporated herein by reference). *P<0.05 SEM=standard error of the mean.
Figure 5C:
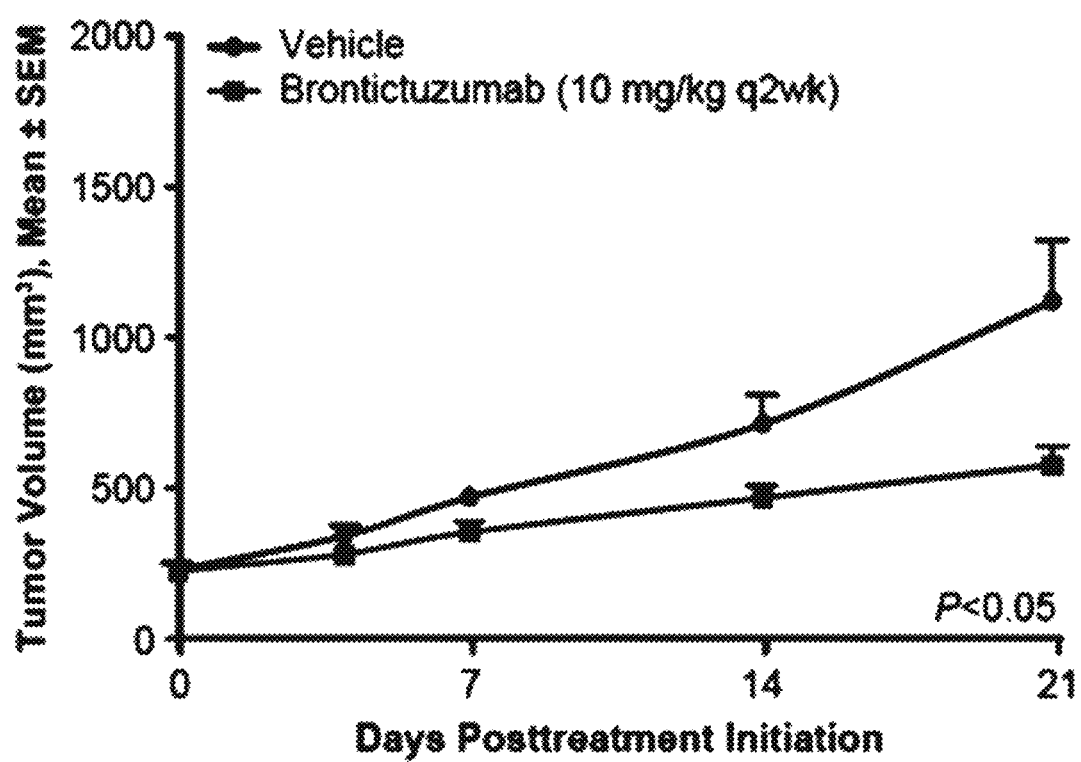
FIG. 5C. Effect of brontictuzumab treatment on tumor volume in ACCx9-Notch1 mutant tumors. Tumor volume in mice bearing an ACCx9-Notch1 mutant tumor was measured over a 21-day period in mice administered either vehicle or the monoclonal antibody brontictuzumab (Ferrarotto R, et al. J Clin Oncol. 2017; 35:352-360, incorporated herein by reference) at 10 mg/kg twice a week. *P<0.05 SEM=standard error of the mean.

Results: Compound (1) was significantly more effective than vehicle at inhibiting tumor growth in mice harbouring ACCx9 mutant tumor (FIG. 5A; P<0.0001). MRK-003 (FIG. 5B; P<0.05) and brontictuzumab (FIG. 5C; P<0.05) also significantly inhibited tumor growth in mice harbouring ACCx9 mutant tumors. CB-103 treatment did not appear to inhibit tumor growth (Cellestia Biotech presentation, Basel Breast Cancer Consortium, October 2017).

Conclusion: The antitumor activity of single-agent Compound (1) in the ACCx9 PDX model is superior to other Notch inhibitors such as CB-103, MRK-003, and brontictuzumab.

Example 5

Phase 2, Open-Label, Single-Arm, Multi-Center Study of Compound (1) in Patients with Adenoid Cystic Carcinoma (ACC) Bearing Activating Notch Mutations Study Rationale Compound (1) is a potent and selective inhibitor of gamma secretase-mediated Notch signalling that is currently under development as an antitumor/antiangiogenic agent for single use or in combination with cytotoxic agents as well as other targeted agents in the treatment of tumour growth and metastasis. A large body of experimental evidence supports a causal role of activating Notch mutations in tumorigenesis. ACC is a rare chemotherapy-refractory cancer of the secretory glands. Notch$^{act\ mut}$ are found in ~20% of ACC pts, characterized by a particularly aggressive disease and poor prognosis. In addition to Notch1 mutations, other Notch mutations (2, 3, 4) were identified in ACC. There is no proven active treatment for recurrent/metastatic (R/M) ACC. Therefore, ACC with Notch pathway activation represents a high unmet therapeutic need.

Objectives

Primary

To assess by independent review committee (IRC) the clinical activity (objective response rate (ORR)) of Compound (1) using radiographic assessments and Response Evaluation Criteria in solid tumours (RECIST) v1.1 (or modified MD Anderson bone criteria) in R/M ACC patients with activating Notch mutations.

Figure 6:
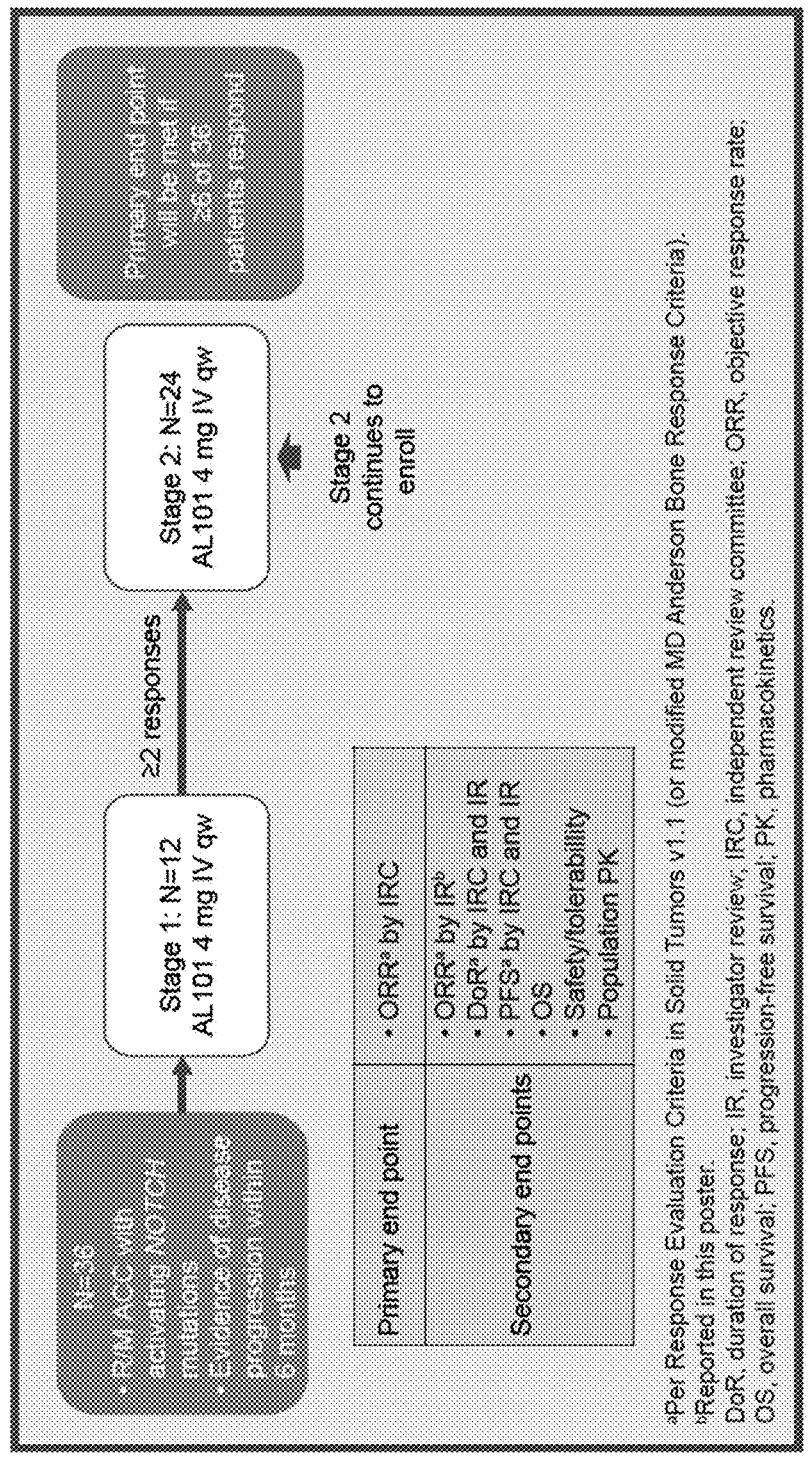
FIG. 6. Phase 2 study scheme of Compound (1) in ACC patients. ACC=adenoid cystic carcinoma; DoR=duration of response; IR=investigator review; IRC=independent review committee; IV=intravenously; ORR=objective response rate; OS=overall survival; PFS=progression-free survival; PK=pharmacokinetics; qw=once weekly; R/M-recurrent/metastatic; $^{a}$per Response Evaluation Criteria in Solid Tumors (RECIST) v1.1 (or modified MD Anderson Bone Response Criteria).

Secondary
  To confirm safety and tolerability of Compound (1) in ACC patients with activating Notch mutations.
  To obtain a set of population parameters and to identify covariates that affect systemic exposure to Compound (1) and metabolite(s).
  ORR by investigator review (IR), duration of response by IRC and IR, progression-free survival (PFS) by IRC, and overall survival (OS).
Exploratory
  To establish correlation between positive NICD stain and Notch1 mutations.
  To establish the correlation between mutations in Notch and associated genes and response or resistance to study drug.
Study Design
  The study scheme in FIG. 6 presents the Phase 2, Simon 2-Stage optimal design, non-comparative, open-label, single-arm, multicenter study of Compound (1) in patients with recurrent or metastatic (R/M) ACC (bone-exclusive disease allowed) who harbor Notch1, Notch2, Notch3, or Notch4 activating mutations (Notch1-4$^{act\ mut}$) Patients with disease progression ≤6 months of enrollment or newly diagnosed metastatic disease were allowed.
  Patients with known activating Notch mutations, per NGS test results gave their informed consent and underwent screening assessments to determine study eligibility over a 28-day screening period. Available mutation status from prior tests with any commercially available or locally developed NGS assay were acceptable. Any newly characterized mutation (such as tandem duplication, variant allele frequency etc.), was evaluated with the sponsor on a case-by-case basis.
  Starting on Cycle 1, Day 1, eligible patients enrolled in the study received Compound (1), 4 mg intravenously (IV) weekly (qwk), on Days 1, 8, 15, and 22 of each 28-day cycle until disease progression, unacceptable toxicity, or consent withdrawal. Paired tumor biopsies were collected at screening (fresh or archival within 5 years) and upon confirmation of disease progression (provided medically safe and not contraindicated). Samples were sent to a central vendor for NGS analysis. Formalin-fixed paraffin embedded (FFPE) slides were evaluated by IHC for NICDI stain.
  During the treatment period, patients underwent radiographic assessments every 8 weeks (±3 days) for review by Independent Central Review (ICR) as well as by the Investigator. Other assessments performed included safety exploratory biomarkers.
  All patients underwent end of study (EOS) visit 30 days post last treatment and were contacted by phone every 3 months thereafter to determine survival status; only in patients who discontinued study treatment due to toxicity, radiographic imaging was done every 3 months until disease progression or until the patient initiated another anti-cancer therapy.
  Data Monitoring Committee (DMC) review: Throughout the study, the independent DMC monitored safety and efficacy parameters at approximately quarterly intervals, after at least 3 patients were treated for at least one cycle.
Study Duration
  It was estimated that recruitment duration for the study would be at least 24 months (up to 12 months for Stage 1 and 12 months for Stage 2).
Study participation for each patient consisted of:
Screening period: Up to 28 days.
Treatment period: Weekly treatment until disease progression, unacceptable toxicity, or consent withdrawal.
EOS: 30 days after the last administration of study drug.
Long-term follow-up: Every 3 months.
Diagnosis and Key Inclusion Criteria
  Adult patients (age ≥18 years) with histologically confirmed adenoid cystic carcinoma (ACC) who had:
    Histologically confirmed ACC with known Notch 1, 2, 3 or 4 activating mutation(s) that is recurrent or metastatic, not amenable to potentially curative surgery or radiotherapy.
    Evidence of radiographic or clinical disease progression within six months of signing informed consent; newly diagnosed metastatic patients were allowed.
    At least one target lesion that is measurable per RECIST v1.1 for patients with nodal or visceral metastasis. Patients with bone exclusive disease were also eligible if bone lesions are evaluable by CT or MRI as per modified MD Anderson (MDA) Criteria.
Key Exclusion Criteria
  Patients were excluded from the study if they met one of the following criteria:
    Diagnosis of another malignancy in the past 2 years.
    Current or recent (within 2 months) gastrointestinal disease such as diarrhea or disorders that increase the risk of diarrhea.
    Evidence of uncontrolled, active infection.
    Symptomatic central nervous system metastases.
    Completed palliative RT<7 days prior to initiating study drug.
    Eastern Cooperative Oncology Group performance status ≥2.
    Life expectancy <3 months.
Investigational Product Route and Dosage Form
  Compound (1) is a potent and selective inhibitor of gamma secretase-mediated Notch signaling. Compound (1) was administered IV at the dose of 4 mg every 7 days (1 day; QW) over 28-day cycles until disease progression, unacceptable toxicity, or consent withdrawal. Compound (1) injection was developed as a single-use sterile solution (1.2 mg/mL; 4 mg) for IV administration in clinical studies; each vial contained 5 mL (equivalent of 6 mg per vial). It was formulated as a sterile concentrate containing Cremophor and ethanol and was diluted with 0.9% Sodium Chloride injection, USP (normal saline) or 5% Dextrose Injection, USP (D5W) to concentrations between 0.01 mg/mL and 0.06 mg/mL. In order to reduce the risk of infusion reactions caused by Cremophor, premedication with H1- and H2-blockers (diphenhydramine and ranitidine or equivalents) or dexamethasone (8-10 mg) were administered.
Statistical Methods
Null Hypothesis
  A response rate of 8% or less was considered not clinically significant.
Sample Size
  The study was conducted using Simon's 2-stage optimal design (FIG. 6). In Stage 1, twelve patients were evaluated for tumor response. Since more than two patients responded, the study proceeded to Stage 2 with 38 enrolled patients. The null hypothesis will be rejected if 6 or more responses are observed in 36 patients. This design yields a type I error rate of 0.05 and power of 0.8 when the true response rate is 25%. Only efficacy evaluable patients were used to implement the two-stage design.
Analysis Population
  Safety analysis set consisted of all enrolled patients who received at least one dose of study drug (even a partial dose).

Efficacy evaluable set included all patients who received study drug and had at least one post baseline on-study assessment of tumor response.

Per-protocol (PP) analysis set consisted of all efficacy evaluable patients without major protocol deviations, as defined by the Sponsor prior to database lock.

Safety and Tolerability Analysis

Safety was assessed on the basis of AEs, clinically significant laboratory abnormalities, concomitant medication use, vital signs, pain assessments, and physical examination data for patients in the safety analysis set. Hematology and clinical chemistry data were summarized by change from baseline and worst-case toxicity grade shift relative to baseline. Deaths were listed by primary cause and date relative to last dose of study drug.

Interim Analysis

In accordance with Simon's 2-Stage optimal design (FIG. 6), response rate data was assessed after Stage 1 to determine whether enrollment should proceed to Stage 2 per defined stopping rules. Stage 1 was assessed after all patients received study drug for at least 2 cycles (8 weeks).

Results

Patients

Of 38 patients who met eligibility criteria, 27 were treated with Compound (1) (Table 2):
- Among the 25 evaluable patients, most had received prior systemic cancer therapy (n=15), cancer surgery (n=18), and/or radiotherapy (n=23).
- Overall, 18 patients were treated with AL101 and had at least 1 predose and 1 postdose radiologic assessment
- Seven patients are undergoing treatment and have not yet had a postdose radiologic assessment.
- Two patients began treatment but discontinued before their first postdose radiologic evaluation: one due to an infusion reaction and one due to non-treatment-related AE and are thus considered nonevaluable for efficacy.

Patients were treated for a median of 3 cycles (12 weeks) (Table 2).

TABLE 2

Disposition and Baseline Characteristics of Treated Patients

| | |
|---|---|
| Screened/enrolled (signed consent), n | 38 |
| Screen failures, n | 7 |
| Current in screening period, n | 4 |
| Treated, n | 27 |
| Nonevaluable | 2 |
| Evaluable | 25 |
| Evaluable for efficacy (baseline and 1 follow-up scan) | 18 |
| Baseline scan only | 7 |
| Median number of cycles, n | 3 |
| Sex,[a] n | |
| Male | 14 |
| Female | 11 |
| Median age[a], years | 50 |
| Race,[a] n | |
| White | 15 |
| Black | 3 |
| Not reported | 1 |
| Not available | 6 |
| ECOG PS,[a] n | |
| 0 | 16 |
| 1 | 9 |

TABLE 2-continued

Disposition and Baseline Characteristics of Treated Patients

| | |
|---|---|
| Disease status,a n | |
| With nodal or visceral metastases | 22 |
| With bone-exclusive metastases | 3 |
| Prior cancer treatment,[a] n | |
| Cancer surgery | |
| Yes/No/Missing data | 18/6/1 |
| Radiotherapy | |
| Yes/No/Missing data | 23/1/1 |
| Systemic cancer therapy | |
| Yes/No/Missing data | 15/9/1 |
| Patients who discontinued treatment,[a,b] n | 12 |
| PD | 9 |
| AEs | 1 |
| Patient decision | 2 |
| Patients still receiving treatment,[a] n | 13 |

[a]Based on patients evaluable for efficacy.
[b]Among the patients evaluable for efficacy, none discontinued due to death.
AEs = adverse events;
ECOG = Eastern Cooperative Oncology Group;
N/A = not available;
PD = progressive disease.

Efficacy

Figure 7:
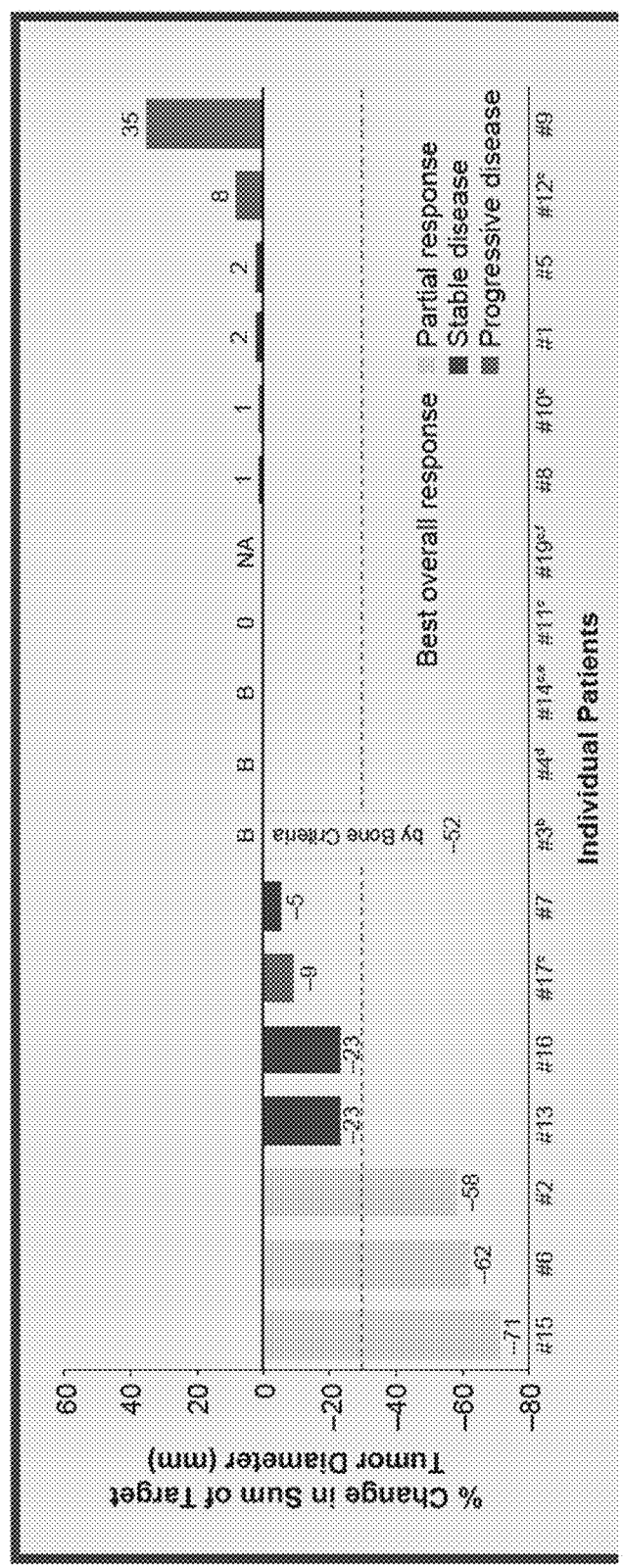
FIG. 7. Best overall responses at Week 8 for 18 ACC patients treated with Compound (1). Waterfall plot of best overall responses, as assessed by investigator per RECIST v1.1 criteria, of 18 ACC patients after 8 weeks of treatment with Compound (1) 4 mg IV qwk. $^{b}$-Patient #3 with bone-only disease, had a PR at week 24 by the investigator, per MDA Bone Response Criteria (52% disease reduction); $^{c}$-Patients with clinical PD; $^{d}$-Patient #4, with bone-only disease, had an SD at week 8, but the value of % change in tumor volume per MDA Bone Response Criteria is not available; $^{e}$-Patient #14, with bone-only disease, had PD at week 8, but the value of % change in tumor volume per MDA Bone Response Criteria is not available. $^{f}$-Patient #19 has missing data (NA) but is included as zero for completeness; B=bone-only disease; NA=not available; dotted line=30% decrease from baseline.
Figure 8:
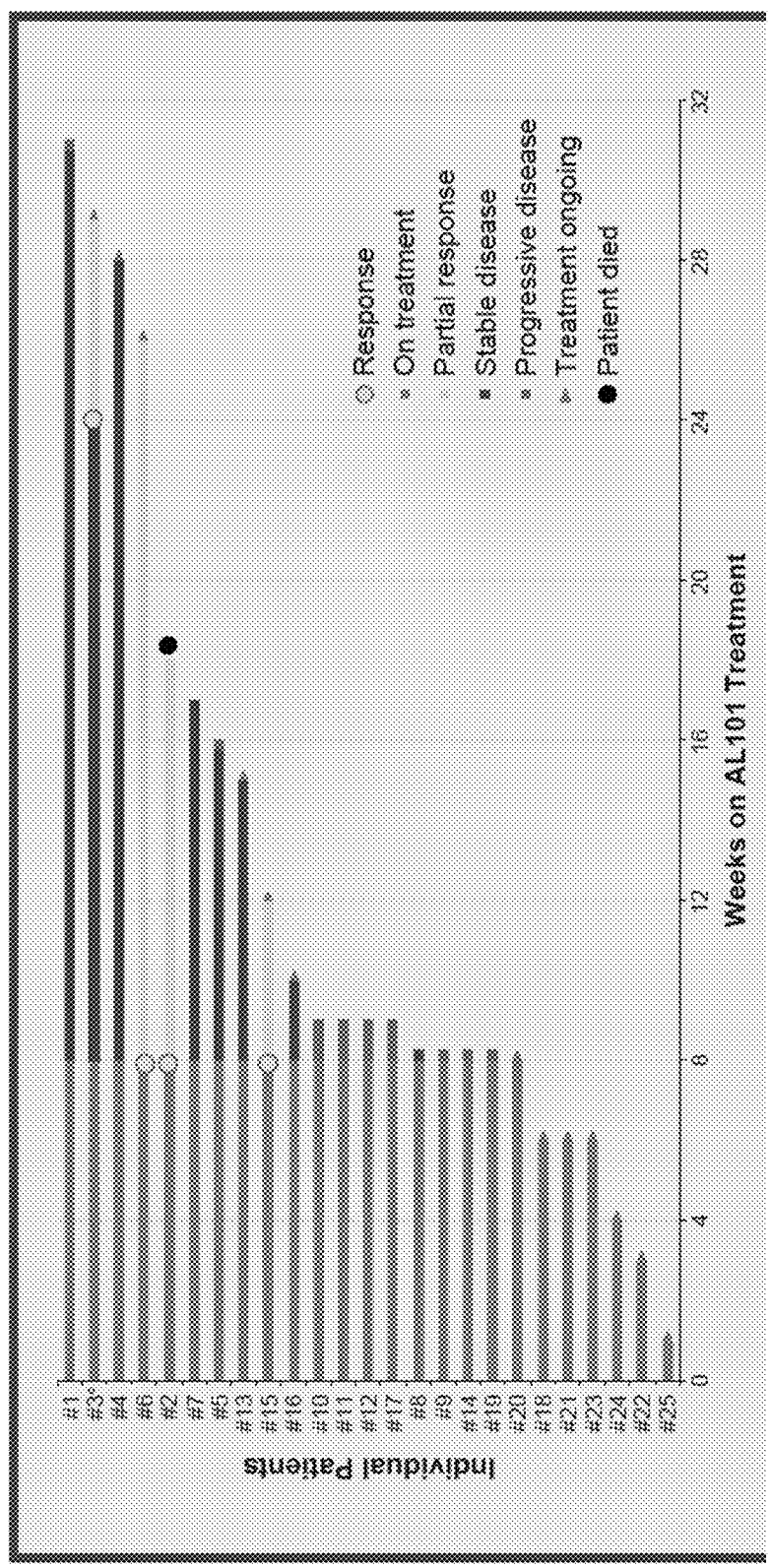
FIG. 8. Time of objective response of 25 ACC patients after Compound (1) treatment. Swimmer plot for time of objective response in relationship to duration of Compound (1) treatment and time of treatment cessation, as assessed by investigator per RECIST v1.1 criteria, of 25 ACC patients treated with Compound (1) 4 mg IV qwk. First response assessment was at week 8. The plot presents all efficacy-evaluable patients, including those who had not yet had their first post-dose follow-up radiologic evaluation. $^{c}$-Patient #3, with bone-only disease, had a PR at week 24 by the investigator, per MDA Bone Response Criteria.
Figure 9:
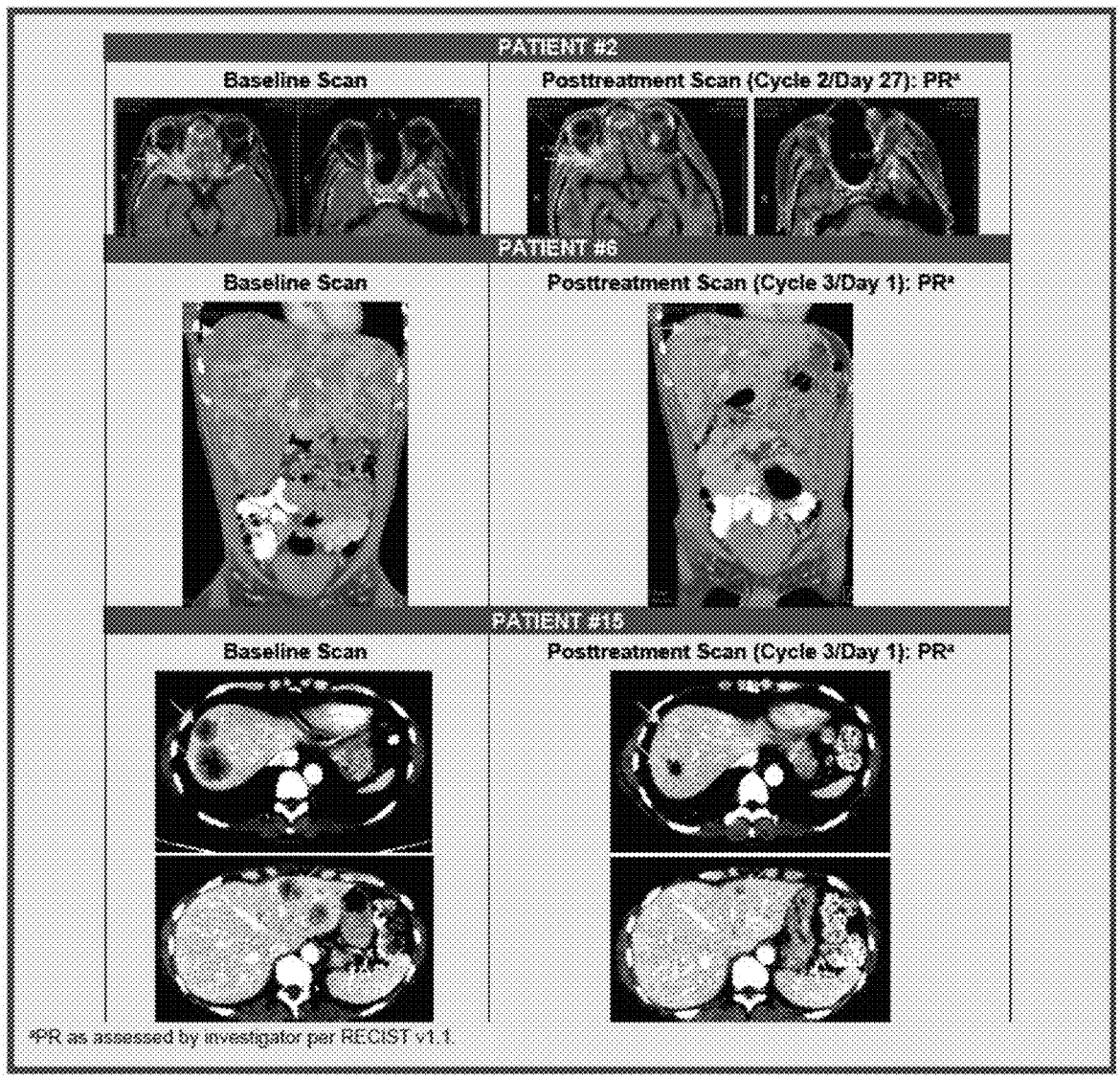
FIG. 9. Radiographic scans of three ACC patients with PR after Compound (1) treatment. ACC Patients #2, 6 and 15 were treated with Compound (1) 4 mg IV qwk and had PR, as assessed by investigator. PR=Partial Response; $^{a}$-assessed by investigator per RECIST v1.1 criteria.

According to the investigator assessment of best response based on RECIST v1.1 of the 18 patients with ACC carrying Notch activating mutations who were treated with 4 mg Compound (1) IV qwk and had at least one follow-up radiological examination, 4 patients had Partial Response (PR) (22%); 7 patients had Stable Disease (SD) (39%); and 7 patients had Progressive Disease (PD) (39%) (FIGS. 7-9), Therefore the Disease control rate (PR+SD), for 11 out of 18 patients, is 61%. The longest response duration thus far (trial is ongoing) is greater than 5 months and the longest SD is greater than 7 months (FIG. 7). Both responses are ongoing, suggesting that the responses may be durable.

Safety

Compound (1) was generally well tolerated, with most AEs mild-to-moderate in severity. There were few dose-reductions, delays, or interruptions (n=5).

There were two on-study nonrelated deaths: one from aspiration pneumonia after surgery for an inguinal hernia (patient did not have a follow-up radiologic evaluation and was considered nonevaluable for efficacy) and one due to hemorrhagic stroke after hip fracture surgery.

A total of 26 Serious Adverse Events (SAEs) occurred among 15 patients. Of these, only three were considered by the investigator to be treatment-related and AEs of special interest. There were two grade 2 infusion reaction events in one patient and one case of grade 1 keratoacanthoma. and twenty-three events were not related to Compound (1).

Only one AE lead to discontinuation (infusion reaction) of the trial for the patient (Table 2). Twenty-one of 27 treated patients experienced AEs, which were treatment-related in 20 patients (Table 3), and 12 patients had grade 3/4 AEs (Table 3), which were treatment-related in one patient (Table 3).

TABLE 3

Safety summary

| | Safety Population (N = 27) | |
|---|---|---|
| | Treatment-Emergent | Treatment-Related |
| Any AE, n (%) | 21 (78) | 20 (74) |
| Any grade 3/4 AE, n (%) | 12 (44) | 1 (4) |
| Any SAE, n (%) | 15 (56) | 2 (7) |

TABLE 3-continued

Safety summary

| | Safety Population (N = 27) | |
|---|---|---|
| | Treatment-Emergent | Treatment-Related |
| Any deaths, n (%) | 2 (7) | 0 |
| AEs leading to discontinuation, n (%) | 1 (4) | 1 (4) |

AE = adverse event;
SAE = serious adverse event.

Treatment-related diarrhea was common (n=15, 56%; Table 4), consistent with reports of Notch pathway inhibition (Purow B. Adv Exp Med Biol 2012; 727:305-319). The majority of events were grade 1/2 (n=14, 52%) and were manageable with protocol guidelines.

TABLE 4

Treatment-related adverse events reported in ≥15% of treated patients

| | Safety Population (N = 27) | |
|---|---|---|
| | Any grade, n (%) | Grade 3/4, n (%) |
| Nausea | 16 (59) | 1 (4) |
| Diarrhea | 15 (56) | 1 (4) |
| Fatigue | 13 (48) | 0 |
| Vomiting | 9 (33) | 0 |
| Cough | 6 (22) | 0 |
| Epistaxis | 6 (22) | 0 |
| Productive cough | 5 (19) | 0 |
| Dry skin | 5 (19) | 0 |
| Insomnia | 5 (19) | 0 |
| Hypophosphatemia | 5 (19) | 1 (4) |

Pharmacokinetics (PK)

The PK parameters for Compound (1) (Table 5) were determined by noncompartmental analysis (NCA) and were similar to PK data from the phase 1 study (Example 1).

TABLE 5

PK characteristics of Compound (1) ($T_{max}$, $C_{max}$, AUC, clearance), at the first dose (Week 1) and at steady state (Week 4)

| | | $T_{max}$ (h) | $C_{max}$ (ng/mL) | AUC (h * ng/mL) | CL (L/h) |
|---|---|---|---|---|---|
| Week 1 N = 10 | Geometric mean | 1.11 | 108.7 | 2786 | 1.43 |
| | CV % geometric mean | 21.5 | 35.7 | 32.9 | 33.6 |
| Week 4 (steady state) N = 12 | Geometric mean | 1.04 | 130.9 | 4196 | 0.92 |
| | CV % geometric mean | 5.6 | 42.9 | 67.9 | 57.1 |

AUC = area under the curve;
CL = clearance;
$C_{max}$ = maximum concentration;
CV % = coefficient of variation;
$T_{max}$ = time taken to reach the maximum concentration.

Figures 10A, 10B:
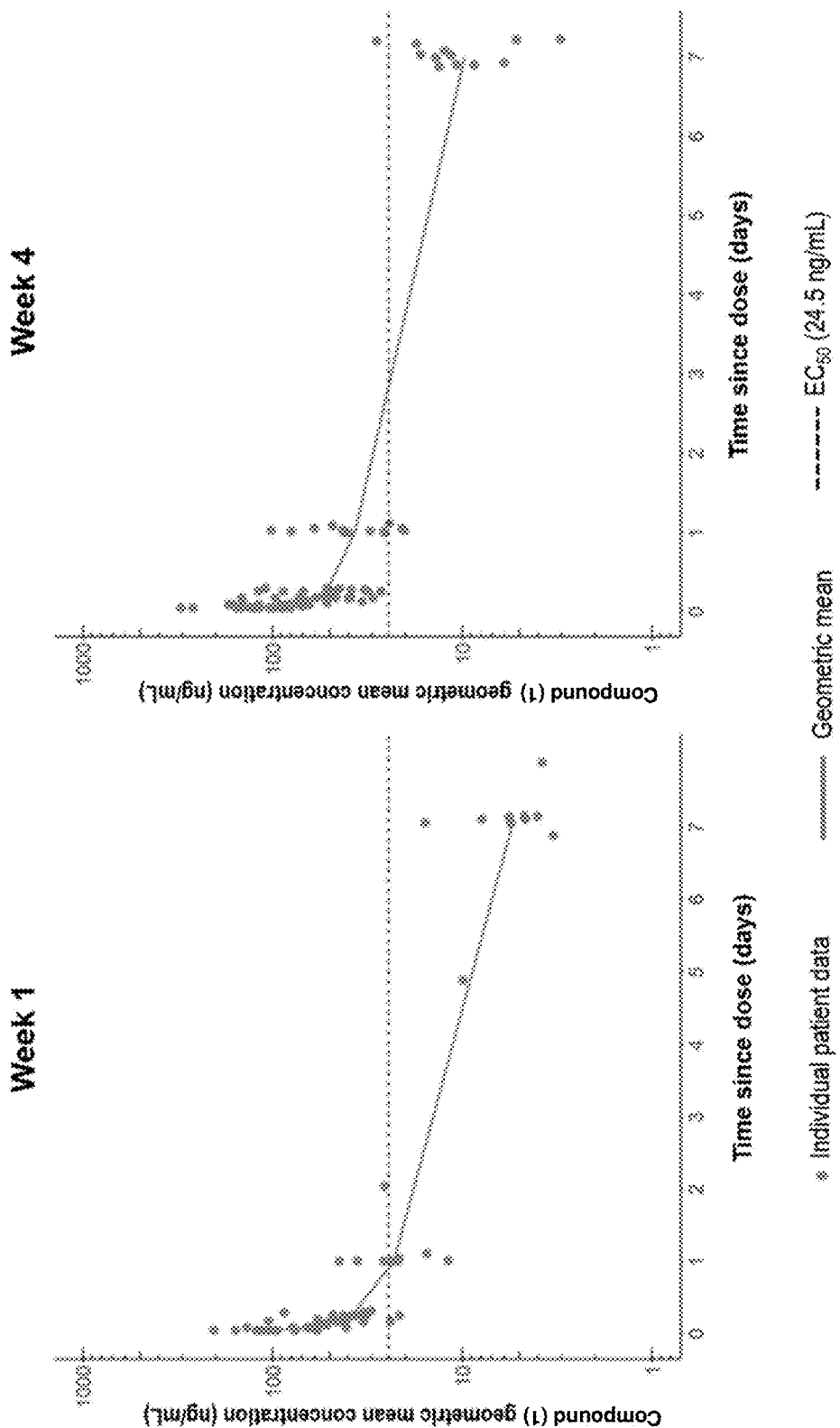
FIG. 10A. Compound (1) plasma concentration after administration of 4 mg of Compound (1)—Week 1. ACC Patients were treated with Compound (1) 4 mg IV qwk, and the geometric mean concentration in ng/mL of Compound (1) in plasma was assessed.
FIG. 10B. Compound (1) plasma concentration after administration of 4 mg of Compound (1)—Week 4. ACC Patients were treated with Compound (1) 4 mg IV qwk, and the geometric mean concentration in ng/mL of Compound (1) in plasma was assessed.

By Week 4, mean plasma concentration of Compound (1) was extrapolated to be above the half maximal effective concentration ($EC_{50}$=24.5 ng/mL) for 3 days (FIG. 10). The $EC_{50}$ was determined using concentration-response modeling of human PD data from the phase 1 study (Example 1).

Pharmacodynamics (PD)

Changes in the expression of PD biomarkers (Notch-induced genes Hes1 and Hes4) were assessed in peripheral whole blood (PWB) as a surrogate tissue. PWB was collected pre-dose and at three timepoints following the $1^{st}$ and $4^{th}$ doses. mRNA expression was determined by quantitative real-time polymerase chain reaction (qPCR).

Figures 11A, 11B:
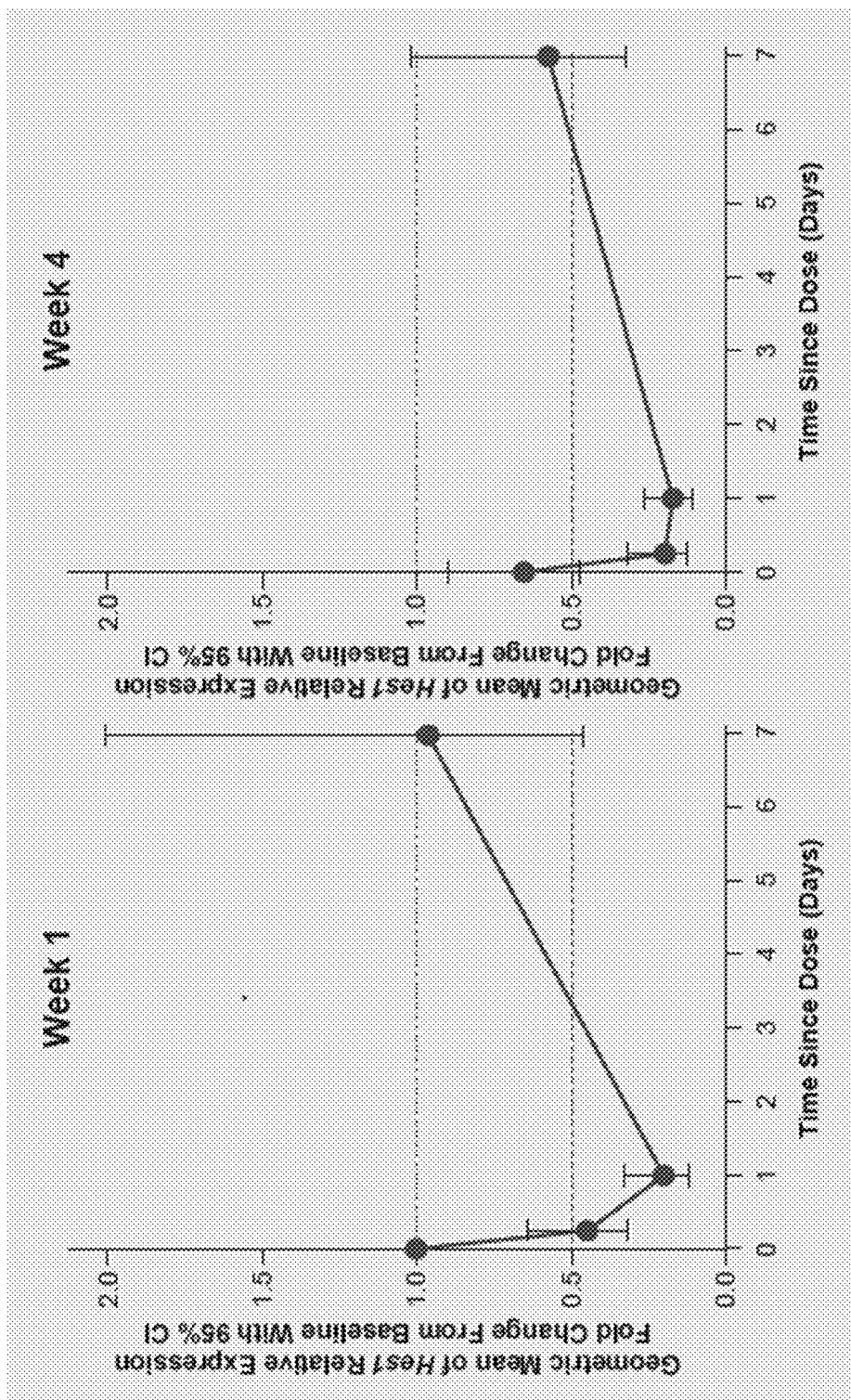
FIG. 11A. Pharmacodynamic effect of Compound (1) administration on the expression of Hes1—Week 1. Expression of the Notch-induced gene Hes1 in peripheral whole blood (PWB) of ACC Patients was determined at three timepoints following the 1$^{st}$ week of treatment with 4 mg Compound (1) IV by quantitative real time polymerase chain reaction (qPCR). CI=confidence interval.
FIG. 11B. Pharmacodynamic effect of Compound (1) administration on the expression of Hes1—Week 4. Expression of the Notch-induced gene Hes1 in PWB of ACC Patients was determined by qPCR at three timepoints following the 4$^{th}$ week of treatment with 4 mg Compound (1) IV. CI=confidence interval.
Figures 12A, 12B:
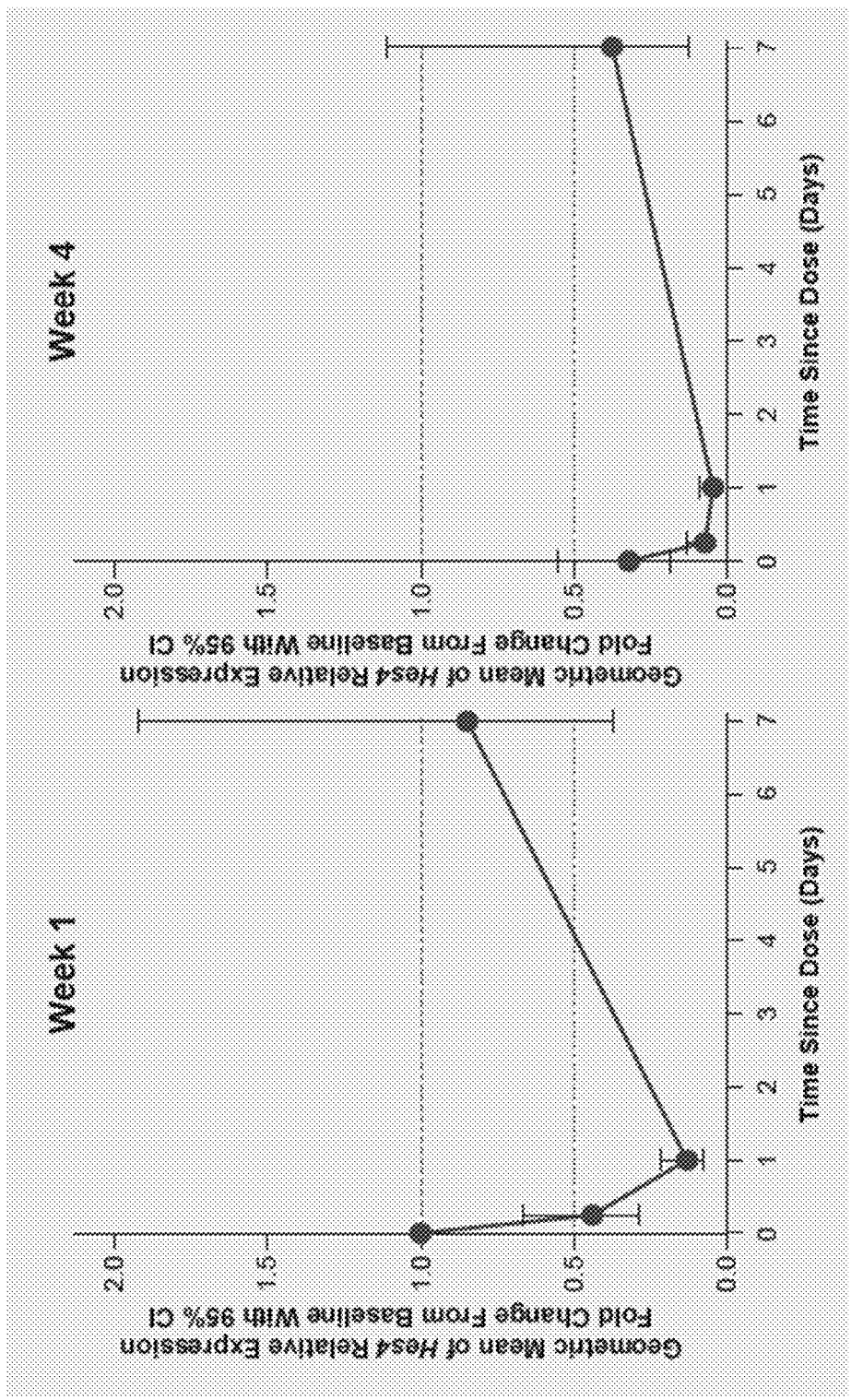
FIG. 12A. Pharmacodynamic effect of Compound (1) administration on the expression of Hes4—Week 1. Expression of the Notch-induced gene Hes4 in PWB of ACC Patients was determined by qPCR at three timepoints following the 1$^{st}$ week of treatment with Compound (1) 4 mg IV. CI=confidence interval.
FIG. 12B. Pharmacodynamic effect of Compound (1) administration on the expression of Hes4—Week 4. Expression of the Notch-induced gene Hes4 in PWB of ACC Patients was determined by qPCR at three timepoints following the 4$^{th}$ week of treatment with Compound (1) 4 mg IV. CI=confidence interval.

Reductions in expression of PD biomarkers in PWB were observed. Over 75% mean peak Hes1 and Hes4 inhibition was observed 2 days post C1D1 dose, and inhibition was sustained for 3-7 days post C1D22 dose (FIGS. 11-12).

The Hes1 change from baseline was very similar to PD data observed from 41 patients in the 4 mg cohort of the phase 1 study (Example 1).

CONCLUSIONS

Safety

Treatment with Compound (1) inpatients with ACC is well tolerated with manageable side effects. There were few dose-reductions, delays, or interruptions.

The most common AEs included nausea, diarrhea, and fatigue with most having grade 1 or 2 severity. Most SAEs were consistent with a recurrent/metastatic cancer population.

Efficacy

Disease control rate (PR plus SD) was noted in 11 of 18 patients (61%) by investigator assessment, including PR in 4 of 18 patients (22%) who had a follow-up scan.

PK and PD

PK and PD data support the current dosing schedule of 4 mg QW. Compound (1) mean plasma PK concentration was maintained above $EC_{50}$ (24.5 ng/mL) for 3 days.

Sustained Notch inhibition (>75% mean peak Hes1 and Hes4 inhibition) in PWB was observed.

What is claimed is:

1. A method of suppressing Adenoid Cystic Carcinoma (ACC) tumor growth in a subject or causing regression of an ACC tumor in a subject, wherein said tumor comprises a Notch-activating genetic alteration comprising the step of administering to said subject a composition comprising one or more compounds selected from the group consisting of:

(1)

and

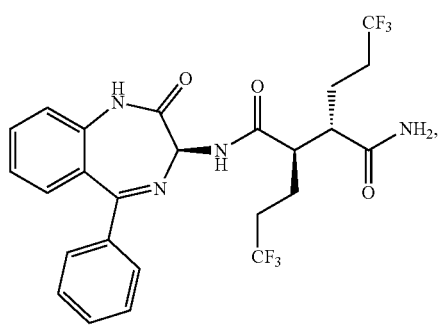

(2)

or salts thereof.

2. The method of claim 1, wherein said composition is administered at a dose of 4 mg.

3. The method of claim 1, wherein said composition is administered at a dose of 6 mg.

4. The method of claim 1, wherein said composition is administered at a dose of 0.3, 0.6, 1.2, 2.4 or 8.4 mg.

5. The method of claim 1, wherein said composition is administered once per week or once every two weeks.

6. The method of claim 1, wherein said ACC tumor comprises tubular ACC, cribriform ACC, or solid ACC.

7. The method of claim 1, wherein said Notch-activating genetic alteration comprises a Notch1 mutation, a Notch2 mutation, a Notch3 mutation, a Notch4 mutation, or a combination thereof.

8. The method of claim 1, wherein said Notch-activating genetic alteration perturbs the structure of the negative regulatory region (NRR) of the Notch gene.

9. The method of claim 1, wherein said Notch-activating genetic alteration functionally inactivates the PEST domain of the Notch gene.

10. The method of claim 1, wherein said Notch-activating genetic alteration comprises a sequence variant in the NRR domain of a Notch gene, PEST domain of a Notch gene, or combination thereof.

11. The method of claim 1, wherein said Notch-activating genetic alteration comprises a gene rearrangement in the ectodomain of a Notch gene.

12. The method of claim 11, wherein said gene rearrangement removes most of the NRR.

13. The method of claim 1, wherein said Notch-activating genetic alteration is in the negative regulatory region (NRR) of the Notch gene and/or in the PEST domain of the Notch gene.

* * * * *